US005871732A

United States Patent [19]
Burkly et al.

[11] Patent Number: 5,871,732
[45] Date of Patent: *Feb. 16, 1999

[54] ANTI-CD4 ANTIBODY HOMOLOGS USEFUL IN PROPHYLAXIS AND TREATMENT OF AIDS, ARC AND HIV INFECTION

[75] Inventors: Linda C. Burkly, West Newton; Patricia L. Chisholm, Quincy; David W. Thomas, Wellsley; Margaret D. Rosa; Joseph J. Rosa, both of Winchester, all of Mass.

[73] Assignee: Biogen, Inc., Cambridge, Mass.

[*] Notice: The terminal 10 months of this patent has been disclaimed.

[21] Appl. No.: 916,098

[22] Filed: Nov. 27, 1991

Related U.S. Application Data

[63] Continuation-in-part of Ser. No. 618,542, Nov. 27, 1990, abandoned.

[51] Int. Cl.[6] .......................... C12P 21/08; A61K 39/395; C08G 75/14
[52] U.S. Cl. ..................................... 424/133.1; 530/387.3; 530/388.75; 424/143.1; 424/154.1
[58] Field of Search ............................. 424/133.1, 143.1, 424/154.1; 530/388.75, 387.3

[56] References Cited

U.S. PATENT DOCUMENTS

| | | |
|---|---|---|
| 4,381,295 | 4/1983 | Kung et al. . |
| 4,515,895 | 5/1985 | Kung et al. . |
| 4,652,447 | 3/1987 | Kung et al. . |
| 4,653,020 | 3/1987 | Kung et al. . |
| 4,816,397 | 3/1989 | Boss et al. . |
| 4,833,092 | 5/1989 | Geysen . |
| 4,908,203 | 3/1990 | Thornton . |

FOREIGN PATENT DOCUMENTS

| | | |
|---|---|---|
| 8901940 | 3/1989 | WIPO . |
| 9109966 | 7/1991 | WIPO . |

OTHER PUBLICATIONS

Linda C. Burkly et al; "Inhibition of HIV Infection by a Novel CD4 Domain 2–Specific Monoclonal Antibody" (The Journal of Immunology—Sep. 1, 1992 pp. 1779–1787).
Wilk et al. Immunology 1990 10–15 (71).
Healy et al. J. Exp. Med. vol. 172 1990 1233–1242.
Trunch et al. Journal of Biological Chemistry. vol. 266(9) 5942, 1991.
Fahey et al. Clin. Exp. Immun. 1992 88, 1–5.
Morrison et al. PNAS. 81. 6851, 1984.
Cohen Science vol. 264 1994. p. 1072.
Jones et al. Nature vol. 321, 1986 p. 522.
Celada et al., 1990, J. Exp. Med. 172:1143–50, "Antibody Raised Against Soluble CD4–rgp 120 Complex Recognizes The CD4 Moiety And Blocks Membrane Fusion Without Inhibiting CD4–gp120 Binding".
Healey et al., 1990, J. Exp. Med. 172:1233–42, "Novel Anti–CD4 Monoclonal Antibodies Separate Human Immunodeficiency Virus Infection And Fusion Of $CD4^+$ Cells From Virus Binding".

Ibegbu et al., 1989, J. Immunol. 142:2250–56, "Structural Features of CD4 Required For Binding To HIV".
Jameson et al., 1988, Science 240:1335–41, "Location And Chemical Synthesis Of A Binding Site For HIV–1 On The CD4 Protein".
Jones et al., 1986, Nature 321:522–25, "Replacing The Complementarity–Determining Regions In A Human Antibody With Those From A Mouse".
Kieber–Emmons et al., 1989, Biochim. Biophys. Acta 989:281–300, "The gp120–CD4 Interface".
Klatzmann et al., 1984, Nature 312:767–68, "T–Lymphocyte T4 Molecule Behaves As The Receptor For Human Retrovirus LAV".
Kowalski et al., 1987, Science 237:1351–55, "Functional Regions Of The Envelope Clycoprotein Of Human Immunodeficiency Virus Type 1".
Lamarre et al., 1989, EMBO J. 8:3271–77, "Class II MHC Molecules And The HIV gp120 Envelope Protein Interact With Functionally Distinct Regions Of The CD4 Molecule".
Lamarre et al., 1989, Science 245:743–46, "The MHC–Binding And gp120–Binding Functions OF CD4 Are Separable".
Landau et al., 1988, Nature 224:159–62, "The Envelope Glycoprotein Of The Human Immunodeficiency Virus Binds To The Immunoglobulin–Like Domain of CD4".
Lasky et al., 1987, Cell 50:975–85, "Delineation Of A Region Of The Human Immunodeficiency Virus Type 1 gp120 Glycoprotein Critical For Interaction With The CD4 Receptor".
Lasky et al., 1986, Science 233:209–12, "Neutralization Of The AIDS Retrovirus By Antibodies To A Recombinant Envelope Glycoprotein".
Lifson and Engleman, 1989, Immunol. Rev. 109:93–117, "Role Of CD4 In Normal Immunity And HIV Infection".
Lifson et al., 1988, Science 241:712–15, "Synthetic CD4 Peptide Derivatives That Inhibit HIV Infection And Cytopathicity".
Lifson et al., 1986, Science 323:1123–27, AIDS Retrovirus Induced Cytopathology: Giant Cell Formation and Involvement Of CD4 Antigen.
Littmann et al., 1988, Cell 55:541, "Corrected CD4 Sequence".

(List continued on next page.)

*Primary Examiner*—Lila Feisee
*Assistant Examiner*—Geetha Bansal
*Attorney, Agent, or Firm*—Warren A. Kaplan; Biogen, Inc.

[57] ABSTRACT

Anti-CD4 antibody homologs, DNA sequences and recombinant DNA molecules encoding them, prophylactic, immunotherapeutic and diagnostic compositions comprising those antibody homologs, and methods for preventing or treating diseases in mammals, including humans, caused by infective agents whose primary targets are $CD4^+$ lymphocytes. Such diseases include acquired immune deficiency syndrome ("AIDS"), AIDS related complex, and human immunodeficiency virus infection.

21 Claims, 15 Drawing Sheets

OTHER PUBLICATIONS

Lundin et al., 1987, J. Immunol. Methods 97:93–100, "A Specific Assay Measuring Binding Of $^{125}$I–Gp120 From HIV to T4⁺/CD4⁺ Cells".

Maddon et al., 1985, Cell, 93–104, "The Isolation And Nucleotide Sequence Of A cDNA Encoding The T Cell Surface Protein T4: A New Member Of The Immunoglobulin Gene Family".

McClure et al., 1987, Nature 330:487–89, "HIV Infection Of Primate Lymphocytes And Conservation Of The CD4 Receptor".

McDougal et al., 1986, Science 231:382–85, "Binding Of HTLV–III/LAV To T4⁺T Cells By A Complex Of The 110 Viral Protein And The T4 Molecule".

McDougal et al., 1986, J. Immunol. 137:2937–44, "Binding Of The Human Retrovirus HTLV–III/LAV/ARV/HIV To The CD4 (T4) Molecule: Conformation Dependence, Epitope Mapping, Antibody Inhibition, And Potential For Idiotypic Mimicry".

Arthos, et al., 1989, Cell 57:469–81, "Identification Of The Residues In Human CD4 Critical For The Binding Of HIV".

Bach et al., 1981, J. Immunol. 127:980–82, "Unusual Phenotypes Of Human Inducer T Cells As Measured By OKT4 And Related Monoclonal Antibodies".

Bates et al., 1989, Prot. Engng. 3:13–21, "A Predicted Three–Dimensional Structure For The Human Immunodeficiency Virus Binding Domains Of CD4 Antigen".

Berger et al., 1988, Prod. Natl. Acad. Sci. USA, 85:2357–61, "A Soluble Recombinant Polypeptide Comprising The Amino–Terminal Half Of The Extracellular Region Of The CD4 Molecule Contains An Active Binding Site For Human Immunodeficiency".

Biddison et al., 1982, J. Exp. Med. 156:1065–76, "Possible Involvement Of The OKT4 Molecule In T Cell Recognition Of Class II HLA Antigens."

Camerini and Seed, 1990, Cell 60:747–54, "A CD4 Domain Important For HIV–Mediated Syncytium Formation Lies Outside The Virus Binding Site."

Chao et al., 1989, J. Biol. Chem. 264:5812–17, "A 113–Amino Acid Fragment Of CD4 Produced In *Escherichia coli* Blocks Human Immunodeficiency Virus–Induced Cell Fusion."

Clayton et al., 1989, Nature 339:548–51, "Identification Of Human CD4 Residues Affecting Class II MHC Versus HIV–1 gp120 Binding."

Clayton et al., 1988, Nature 335:363–66, "Substitution Of Murine For Human CD4 Residues Identifies Amino Acids Critical For HIV–gp120 Binding."

Dalgleish et al., Nov. 1987, Lancet 2:1047–50, "Neutralisation Of HIV Isolates By Anti–Idiothypic Antibodies Which Mimic The T4 (CD4) Epitope: A Potential AIDS Vaccine".

Dalgleish et al., 1984, Nature 312:763–67, "The CD4 (T4) Antigen Is An Essential Component Of The Receptor For The AIDS Retrovirus".

Devlin et al., 1990, Science 249:404–07, "Random Peptide Libraries: A Source Of Specific Protein Binding Molecules".

Engleman et al., 1981, J. Immunol. 127:2124–29, "Activation Of Human T Lymphocyte Subsets: Helper And Suppressor/Cytotoxic T Cells Recognize And Respond To Distinct Histocompatibility Antigens".

Fisher et al., 1988, Nature 331: 76–78, "HIV Infection Is Blocked In Vitro By Recombinant Soluble CD4".

Garlick et al., 1990, AIDS Res. Hum. Retroviruses 6:465–79, "*Escherichia coli* Expression, Purification, And Biological Activity Of A Truncated Soluble CD4".

Gay et al., 1987, Nature 328:626–29, "Functional Interaction Between Human T–Cell Protein CD4 And The Major Histocompatibility Complex HLA–DR Antigen".

Gefter et al., 1977, Somat. Cell Gent. 3:231–36, "A Simple Method For Polyethylene Glycol–Promoted Hybridization Of Mouse Myeloma Cells".

Habeshaw and Dalgleish, 1989, J. AIDS 2:457–698, "The Relevance Of HIV env/CD4 Interactions To The Pathogenesis Of Acquired Immune Deficiency Syndrome".

Hillman et al., 1990, J. Immunol. 144:2131–39, Chemically Induced CD4 Mutants Of A Human T Cell Line–Evidence for Dissociation between Binding of HIV I Envelope and Susceptibility to HIV I Infection and Synctia Formation.

Merkenschlager et al., 1990, J. Immunol. 145:2839–45, "Functional Epitope Analysis Of the Human CD4 Molecule—The MHC Class II–Dependent Activation of Resting T Cells Is Inhibited by Monoclonal Antibodies to CD4 Regardless whether or Not They Recognize Epitopes Involved in the Binding of MHC Class II or HIV gp120".

Mizukami et al., 1988, Proc. Natl. Acad. Sci. USA 85:9273–77, "Binding Region For Human Immunodeficiency Virus (HIV) And Epitopes For HIV–Blocking Mononclonal Antibodies Of The CD4 Molecule Defined By Site–Directed Mutagenesis".

Morrison, et al., 1984, Proc. Natl. Acad. Sci. USA, 81:6851–55, "Chimeric Human Antibody Molecules: Mouse Antigen–Binding Domains With Human Constant Region Domains".

Negoro and Tanigaki, 1986, Human Immunol. 15:137–49, "Serological And Functional Analysis Of The Epitope Clusters On Leu3/T4 Antigen".

Perno et al., 1990, J. Exp. Med. 171:1043–56, "Infection Of Monocytes By Human Immunodeficiency Virus Type–1 Blocked By Inhibitors Of CD4–gp120 Binding, Even In The Presence Of Enhancing Antibodies".

Peterson and Seed, 1988, Cell 54:65–72, "Genetic Analysis Of Monoclonal Antibody And HIV Binding Sites On The Human Lymphocyte Antigen CD4".

Popovic et al., 1984, Science 224:497–508, "Detection, Isolation And Continuous Production Of Cytopathic Retroviruses (HTLV–III) From Pateitns With AIDS and Pre–AIDS".

Rao et al., 1983, Cell 80:310–19, "Five Epitopes Of A Differentiation Antigen On Human Inducer T Cells Distinguished By Monoclonal Antibodies".

Ratner et al., 1985, Nature 313:277–84, "Complete Nucleotide Sequence Of The AIDS Virus, HTLV–III".

Richardson et al., 1988, Proc. Natl. Acad. Sci. USA 85:6102–06, "Binding Site For Human Immunodeficiency Virus Coat Protein gp120 Is Located In The NH$_2$–Terminal Region of T4 (CD4) and Requires The Intact Variable–Region–Like Domain".

Robert–Guroff et al., 1985, Nature 316:72–74, "HTLV–II-I–Neutralizing Antibodies In Patients With AIDS and AIDS–Related Complex".

Robey and Axel, 1990, Cell 60:697–700, "CD4 Collaborator In Immune Recognition And HIV Infection".

Sattentau et al., 1989, J. Exp. Med. 170:1319–34, "Structural Analysis Of The Human Immunodeficiency Virus–Binding Domain Of CD4".

Sattentau and Weiss, 1988, Cell 52:631–33, "The CD4 Antigen: Physiological Ligand And HIV Receptor".

Sattentau et al., 1986, Science 234:1120–23, "Epitopes Of The CD4 Antigen And HIV Infection".

Schooley et al., 1989, Ann. Int. Med. 11:247–53, "Recombinant Soluble CD4 Therapy In Patients With Aids Or AIDS–Related Complex—A Phase I/II Escalating Dose Trial".

Sleckman et al., 1987, Nature 328:351–53, "Expression And Function Of CD4 In A Murine T–Cell Hybridoma".

Sodroski et al., 1986, Nature 322:470–74, "Role Of The HTLV–III/LAV Envelope In Syncytium Formation And Cytopathicity".

Walker et al., 1984, Proc. Natl. Acad. Sci. USA 84:812—24, "Inhibition Of Human Immunodeficiency Virus Syncytium Formation And Virus Replication By Castanospermine".

Ward et al., 1989, Nature 341:544–46, "Binding Activities Of A Repertoire Of Single Immunoglobulin Variable Domains Secreted From *Escherichia coli*".

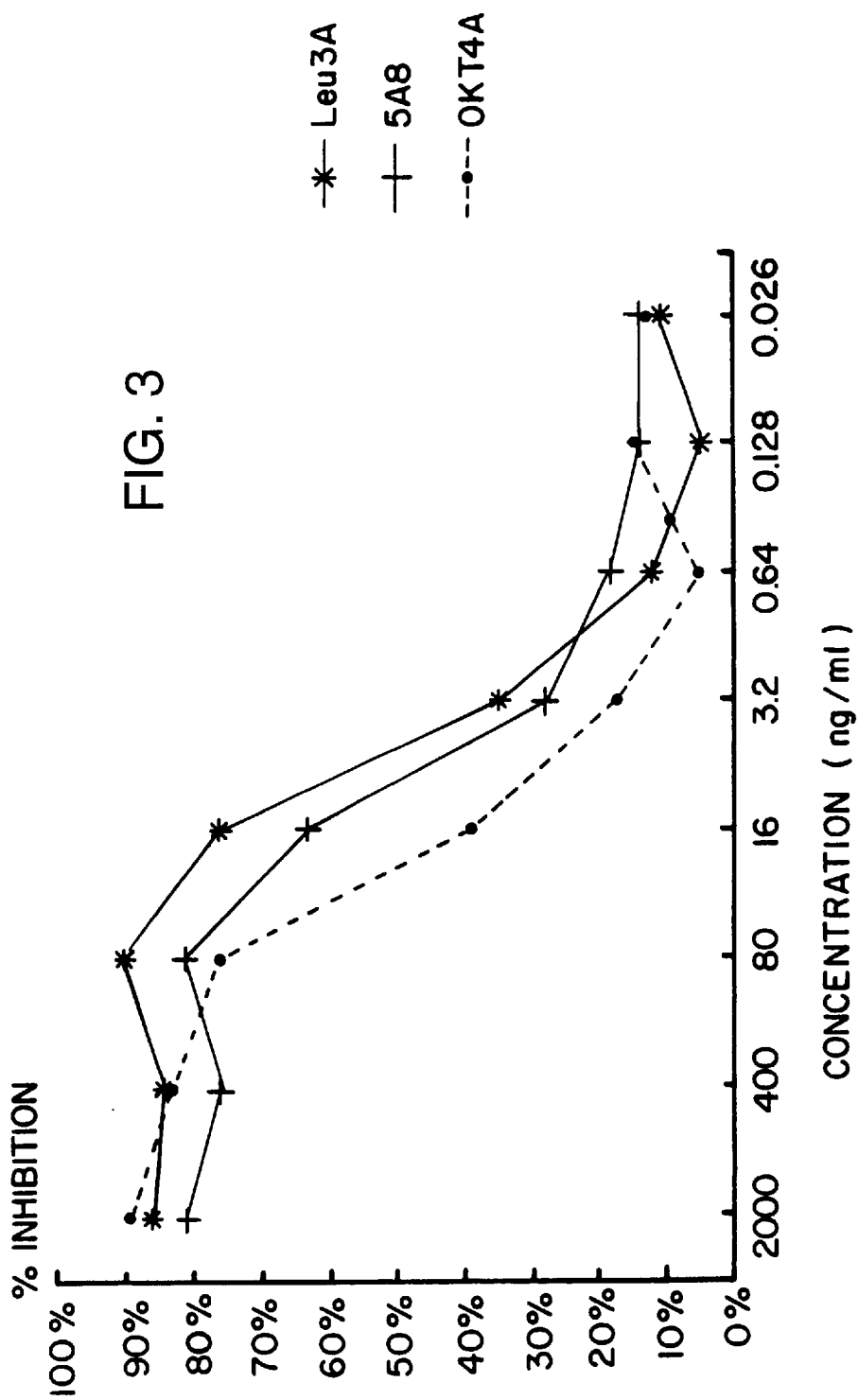

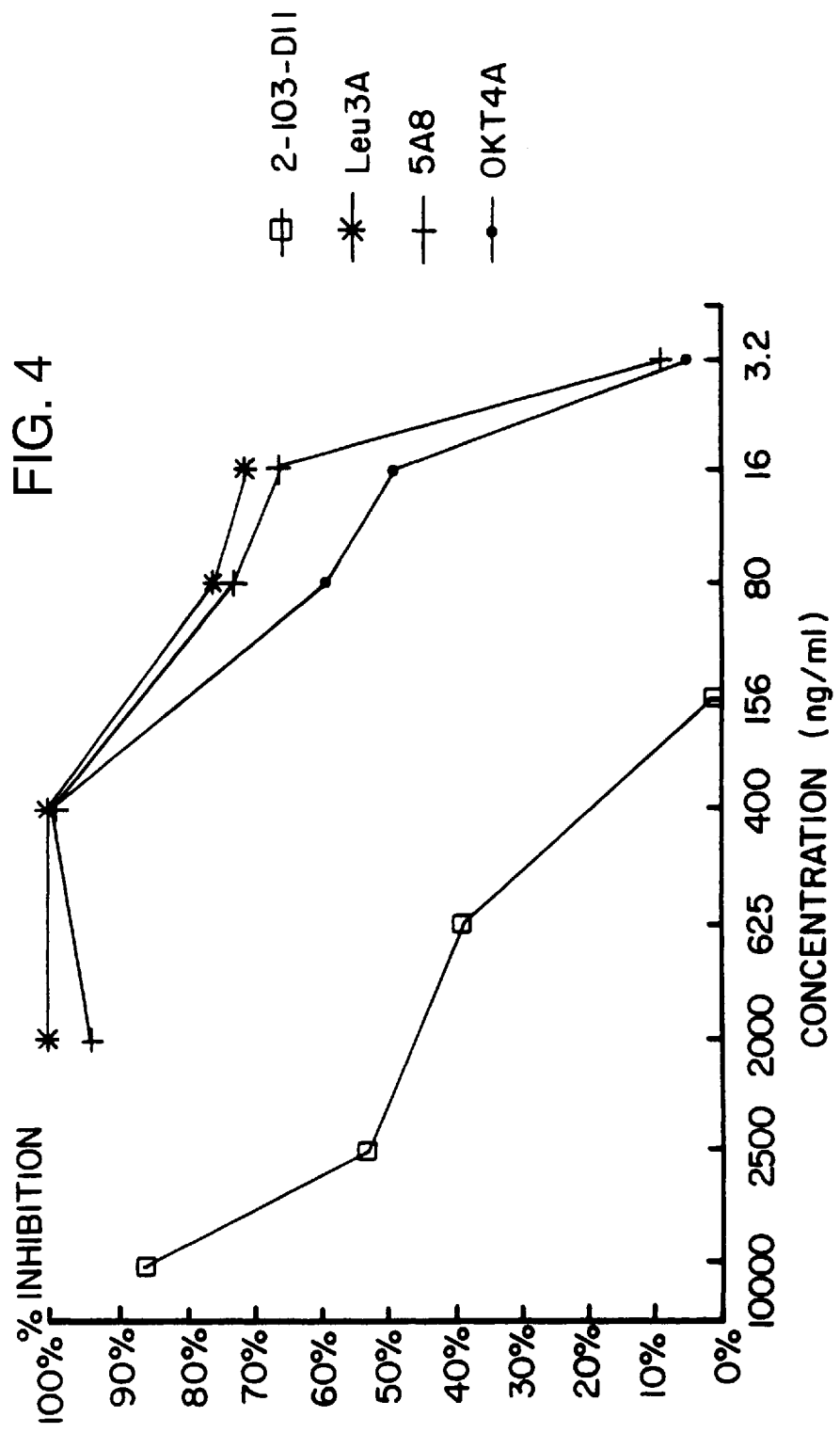

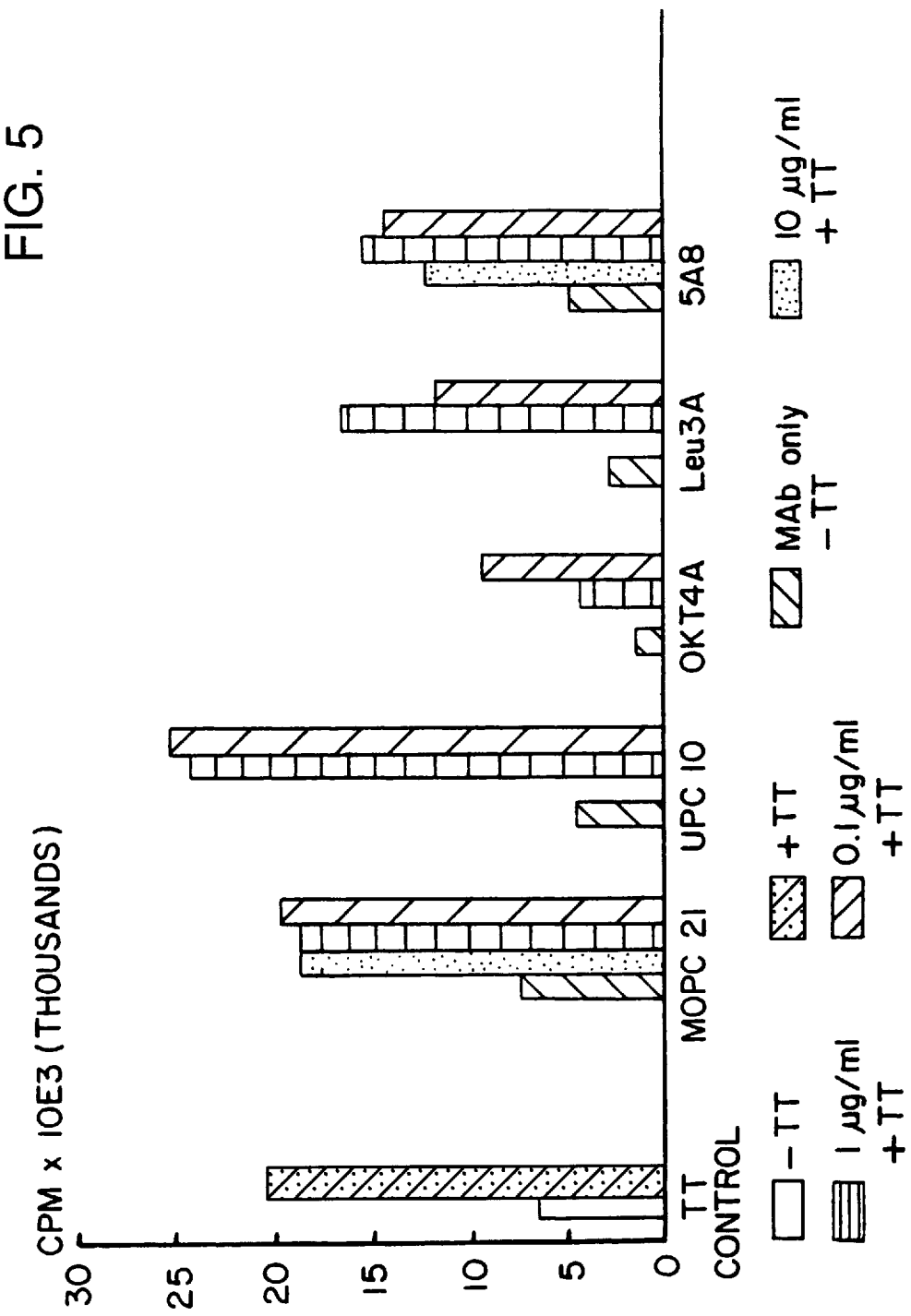

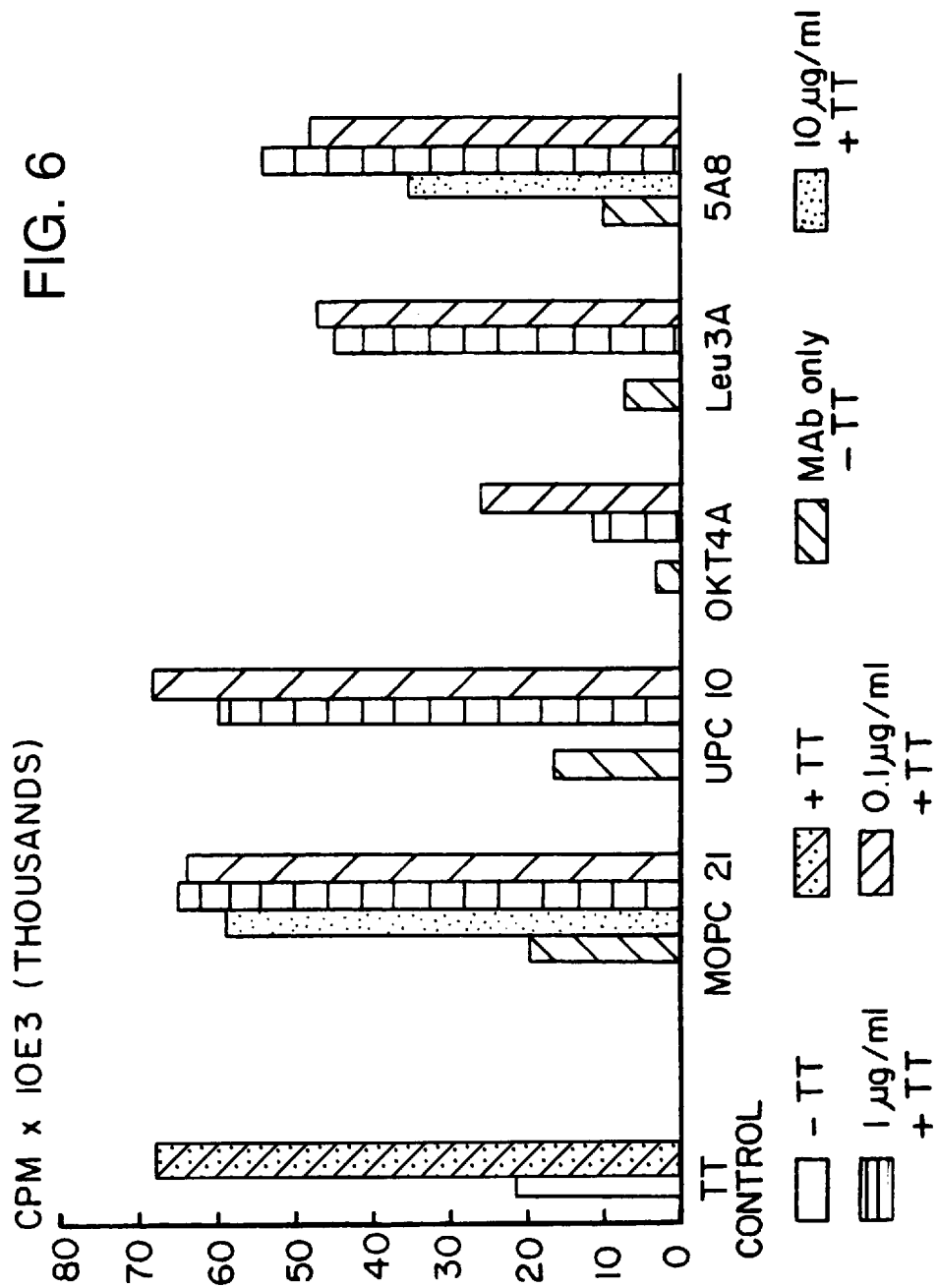

ANTI-CD4 ANTIBODY HOMOLOGS USEFUL IN PROPHYLAXIS AND TREATMENT OF AIDS, ARC AND HIV INFECTION

This application, filed as PCT international application PCT/US 91/08843 on Nov. 27, 1991, is a continuation-in-part of application Ser. No. 07/618,542, now abandoned, filed Nov. 27, 1990, the entire contents of which are incorporated herein by reference.

TECHNICAL FIELD OF INVENTION

This invention relates to anti-CD4 antibody homologs, to DNA sequences encoding those homologs, to prophylactic, immunotherapeutic and diagnostic compositions comprising those homologs, and to methods for preventing or treating diseases in mammals, including humans, caused by infective agents whose primary targets are CD4$^+$ lymphocytes. Such diseases include acquired immune deficiency syndrome ("AIDS"), AIDS related complex, and human immunodeficiency virus infection.

BACKGROUND OF THE INVENTION

CD4 is a cell surface glycoprotein of CD4$^+$ T lymphocytes (helper/inducer cells). CD4$^+$ lymphocytes are critical regulatory cells of the human immune system. They mediate T cell proliferation, lymphokine release and helper cell interactions affecting immunoglobulin release. The primary targets of certain infective agents, including the human immunodeficiency virus ("HIV"), are cells bearing the CD4 glycoprotein.*

* This application uses the generic term human immunodeficiency virus ("HIV") to refer to independent isolates from AIDS patients and to laboratory strains derived therefrom. The term HIV includes viruses elsewhere identified as human T cell lymphotrophic virus type III ("HTLV-III"), lymphadenopathy-associated virus ("LAV") and AIDS-associated retrovirus ("ARV"). The HIV terminology was adopted by the human retrovirus subcommittee of the International Committee On Taxonomy Of Viruses.

Such cells include CD4$^+$ lymphocytes, macrophages and certain brain cells.

Upon infection with HIV, CD4$^+$ lymphocytes are rendered non-functional and become depleted. This T cell depletion has been attributed both to recurrent cycles of infection resulting from lysis of infected cells and to fusion (syncytia formation) between CD4$^+$ infected and uninfected cells (J. Sodroski et al., "Role of The HTLV-III/LAV Envelope In Syncytium Formation And Cytopathicity", Nature, 322, pp. 470–74 (1986)3. The depletion of CD4$^+$ lymphocytes leads to immunosuppression, with the patient becoming susceptible to a wide range of opportunistic infections and malignancies. Such immunosuppression is seen in patients suffering from acquired immunodeficiency syndrome ("AIDS"). In some cases, AIDS is accompanied by central nervous system disorders, thought to be directly caused by HIV infection of CD4$^+$ brain cells. Complete clinical manifestation of AIDS is usually preceded by AIDS related complex ("ARC"), a syndrome characterized by symptoms such as persistent generalized lymphadenopathy, fever and weight loss. HIV is thought to be the etiological agent for AIDS and its precursor, ARC [M. G. Sangadharan et al., "Detection, Isolation And Continuous Production Of Cytopathic Retroviruses (HTLV-III) From Patients With AIDS And Pre-AIDS", Science, 224, pp. 497–508 (1984)].

The major surface (envelope) protein of HIV is produced as a precursor polypeptide (gp160) which, in mature form, is cleaved into a large heavily glycosylated exterior membrane protein having about 481 amino acids—gp120—and a smaller transmembrane protein of about 345 amino acids, which may be glycosylated—gp41 [L. Ratner et al., "Complete Nucleotide Sequence Of The AIDS Virus", HTLV-III, Nature, 313, pp. 277–84 (1985)].

It is believed that HIV gp120 selectively binds to CD4 epitope(s), thus targeting HIV to CD4$^+$ cells [A. G. Dalgleish et al., "The CD4 (T4) Antigen Is An Essential Component Of The Receptor For The AIDS Retrovirus", Nature, 312, pp. 763–67 (1984); D. Klatzmann et al., "T-Lymphocyte T4 Molecule Behaves As The Receptor For Human Retrovirus LAV", Nature, 312, pp. 767–68 (1984)]. The binding of HIV gp120 to cell surface CD4 is thought to initiate infection of the CD4$^+$ cell. It is also thought to initiate membrane fusion of infected CD4$^+$ cells with uninfected CD4$^+$ cells (i.e., syncytia formation), which contributes to cell-to-cell transmission of the virus and to its cytopathic effects [J. A. Habeshaw and A. G. Dalgleish, "The Relevance Of HIV env/CD4 Interactions To The Pathogenesis Of Acquired Immune Deficiency Syndrome", J. AIDS, 2, pp. 457–68 (1989); J. D. Lifson and E. G. Engleman, "Role Of CD4 In Normal Immunity And HIV Infection", Immunol. Rev., 109, pp. 93–117 (1989)].

Mature CD4 (also known as T4) is a 433 amino acid glycoprotein displaying a molecular mass of 55,000 to 62,000 daltons, having an extracellular domain (approximately $AA_1$–$AA_{375}$), a membrane spanning domain (approximately $AA_{376}$–$AA_{395}$) and a cytoplasmic tail (approximately $AA_{396}$–$AA_{433}$). CD4 is synthesized as a pre-protein with a 25 amino acid signal sequence. The nucleotide sequence and deduced amino acid sequence for cDNA encoding full length human CD4 have been reported [P. J. Maddon et al., "The Isolation And Nucleotide Sequence Of A cDNA Encoding The T cell Surface Protein T4: A New Member Of The Immunoglobulin Gene Family", Cell, 42, pp. 93–104 (1985); D. R. Littman et al., "Corrected CD4 Sequence", Cell, 55, p. 541 (1988)]. The CD4 extracellular domain consists of four tandem regions having homology to immunoglobulin V regions—V1 (spanning approximately $AA_1$–$AA_{100}$), V2 (spanning approximately $AA_{101}$–$AA_{180}$), V3 (spanning approximately $AA_{181}$–$AA_{290}$) and V4 (spanning approximately $AA_{291}$–$AA_{375}$ [see Maddon et al., Cell, supra; J. Wang et al., "Atomic Structure Of A Fragment Of Human CD4 Containing Two Immunoglobulin-Like Domains", Nature, 348, pp. 411–18 (1990)].

The CD4 V1 region has been identified as the binding site of HIV gp120 [J. Arthos et al., "Identification Of The Residues In Human CD4 Critical For The Binding Of HIV", Cell, 57, pp. 469–81 (1989); T. Mizukami et al., "Binding Region For Human Immunodeficiency Virus (HIV) And Epitopes For HIV-Blocking Monoclonal Antibodies Of The CD4 Molecule Defined By Site-Directed Mutagenesis", Proc. Natl. Acad. Sci. USA, 85, pp. 9273–77 (1988); A. Peterson and B. Seed, "Genetic Analysis Of Monoclonal Antibody And HIV Binding Sites On The Human Lymphocyte Antigen CD4", Cell, 54, pp. 65–72 (1988); N. R. Landau et al., "The Envelope Glycoprotein Of The Human Immunodeficiency Virus Binds To The Immunoglobulin-Like Domain Of CD4", Nature, 334, pp. 159–62 (1988); L. K. Clayton et al., "Substitution Of Murine For Human CD4 Residues Identifies Amino Acids Critical For HIV-gp120 Binding", Nature, 335, pp. 363–66 (1988)].

The possible ability of anti-CD4 antibodies to prevent or treat HIV infection by blocking HIV gp120 binding to CD4 has led a number of workers to explore the ability of certain anti-CD4 antibodies to block HIV-induced syncytia formation between CD4$^+$ cells, as well to study the immunosuppressiveness of some of those antibodies.

For example, the CD4 V1-specific antibodies Leu3A and OKT4A have been reported to be effective blockers of HIV-induced syncytia formation [Q. J. Sattentau, "Epitopes Of The CD4 Antigen And HIV Infection", Science, 234, pp. 1120–23 (1986); B. A. Jameson et al., "Location And Chemical Synthesis Of A Binding Site For HIV-1 On The CD4 Protein", Science, 240, pp. 1335–39 (1988); Peterson and Seed, Cell, supra]. However, these antibodies have serious drawbacks for use as a pharmaceutical for treatment of HIV infection. For example, they can not bind to or act on a CD4 molecule which is already bound to HIV gp120, because OKT4A and Leu3A recognize CD4 epitopes that overlap with the gp120 binding site [see, e.g., P. A. Bates et al., "A Predicted Three-Dimensional Structure For The Human Immunodeficiency Virus Binding Domains Of CD4 Antigen", Prot. Engng., 3, pp. 13–21 (1989); J. S. McDougal et al., "Binding Of The Human Retrovirus HTLV-III/LAV/ARV/HIV To The CD4 (T4) Molecule: Conformation Dependence, Epitope Mapping, Antibody Inhibition, And Potential For Idiotypic Mimicry", J. Immunol., 137, pp. 2937–44 (1986); Landau et al., Nature, supra; A. G. Dalgleish et al., "Neutralisation Of HIV Isolates By Anti-Idiotypic Antibodies Which Mimic The T4 (CD4) Epitope: A Potential AIDS Vaccine", Lancet, 2, pp. 1047–50 (1987)].

Also, OKT4A has been reported to be quite immunosuppressive, which is not a desirable characteristic for a putative AIDS therapeutic [D. Lamarre et al., "Class II MHC Molecules And The HIV gp120 Envelope Protein Interact With Functionally Distinct Regions Of The CD4 Molecule", EMBO J., 8, pp. 3271–77 (1989); W. E. Biddison et al., "Possible Involvement Of The OKT4 Molecule In T Cell Recognition Of Class II HLA Antigens", J. Exp. Med., 156, pp. 1065–76 (1982)].

Anti-CD4 monoclonal antibodies that are specific for other CD4 epitopes or domains have been studied, but the published reports on these antibodies also evidence drawbacks for use as AIDS therapeutics.

One such antibody is OKT4B, which has been reported to be specific for the V2 domain of CD4 [T. Kieber-Emmons et al., "The gp120-CD4 Interface: Structural, Immunological And Pathological Considerations", Biochim. Biophys. Acta, 989, pp. 281–300 (1989)]. There have been conflicting reports as to whether OKT4B significantly interferes with HIV gp120 binding to CD4 [McDougal et al., J. Immunol., supra; K. Lundin et al., "A Specific Assay Measuring Binding Of $^{125}$I-GP120 From HIV To T4$^+$/CD4$^+$ Cells", J. Immunol. Methods, 97, pp. 93–100 (1987); Lamarre et al., EMBO J., supra]. And, OKT4B has been reported to be significantly more immunosuppressive than OKT4A [Lamarre et al., EMBO J., supra]. Moreover, OKT4B is a relatively weak blocker of HIV-induced syncytia formation, as compared to OKT4A [Sattentau et al., Science, supra].

Other anti-CD4 antibodies that have been reported to have some effect on HIV-induced syncytia formation, and also have been reported to bind to CD4 epitopes distinct from the epitopes bound by OKT4A and Leu3A, include MT151, VIT4 and MT321 [Sattentau et al., Science, supra]. However, several more recent independent studies indicate that these closely related antibodies recognize conformational-dependent CD4 epitopes that overlap with the CD4 epitope involved in gp120 binding [Q. J. Sattentau et al., "Structural Analysis Of The Human Immunodeficiency Virus-Binding Domain Of CD4", J. Exp. Med., 170, pp. 1319–34 (1989); Bates et al., Prot. Engng., supra; Landau et al., Nature, supra, M. Merkenschlager et al., "Functional Epitope Analysis Of The Human CD4 Molecule", J. Immunol., 9, pp. 2839–45 (1990)].

Another anti-CD4 antibody that has been studied is OKT4, which is specific for the V3V4 domain of CD4 [E. A. Berger et al., "A Soluble Recombinant Polypeptide Comprising The Amino-Terminal Half Of The Extracellular Region Of The CD4 Molecule Contains An Active Binding Site For Human Immunodeficiency Virus", Proc. Natl. Acad. Sci. USA, 85, pp. 2357–61 (1988)]. OKT4 has even greater drawbacks as a therapeutic agent for HIV infection than OKT4A, Leu3A, OKT4B and other known anti-CD4 antibodies. For example, OKT4 has been reported to be a "nonblocker" of HIV-induced syncytia formation [Sattentau, Science, supra].

Before our invention, no anti-CD4 antibody had been reported to be capable of both not significantly blocking the binding of HIV gp120 to human CD4 and effectively blocking HIV-induced syncytia formation. Such an antibody would clearly offer advantages for therapeutic intervention in AIDS, ARC and HIV infection, as it could be used to intervene after HIV binding to CD4, or in combination with agents that do block the HIV gp120-CD4 binding event. Thus, the need exists for anti-CD4 antibodies having such a highly desirable combination of properties, for use in the treatment and prevention of AIDS, ARC and HIV infection.

SUMMARY OF THE INVENTION

The present invention generally solves many of the problems referred to above by providing, for the first time, antibody homologs, preferably monoclonal antibodies, that bind to human CD4 without significantly blocking binding of HIV gp120 to human CD4 and that display one of the following sets of properties: (1) block HIV-induced syncytia formation between CD4$^+$ cells at least about as well as OKT4A (a commercially available CD4 V1-specific anti-CD4 monoclonal antibody); (2) block HIV-induced syncytia formation between CD4$^+$ cells better than OKT4 (a commercially available CD4 V3V4-specific anti-CD4 monoclonal antibody) and are less immunosuppressive than OKT4A in an in vitro tetanus toxoid-specific proliferation assay; or (3) block HIV-induced syncytia formation between CD4$^+$ cells at least about as well as OKT4A and are less immunosuppressive than OKT4A in an in vitro tetanus toxoid-specific proliferation assay.

Certain of the anti-CD4 antibody homologs of this invention will bind to a human CD4 fragment consisting of CD4 $AA_1$–$AA_{180}$ (i.e., they are V1V2-specific), but will not bind to a human CD4 fragment consisting of CD4 $AA_1$–$A_{113}$ (i.e., they are not solely V1-specific). Similarly, certain antibody homologs of this invention do not significantly inhibit the binding of CD4 V1-specific antibodies to human CD4. The preferred anti-CD4 antibody homologs of this invention also inhibit infection of CD4$^+$ cells by HIV.

Other preferred antibody homologs of this invention display one or more characteristics selected from causing no significant (a) decrease in the number of circulating CD4$^+$ cells in vivo, (b) modulation of CD4 from the surface of CD4$^+$ cells in vivo, (c) decrease in peripheral white blood cell counts in vivo, and (d) decrease in the antibody titer elicited in response to foreign antigens in vivo.

The present invention provides anti-CD4 antibody homologs of many types. These include monoclonal antibodies, recombinant antibodies, recombinant chimeric antibodies and recombinant humanized antibodies. The provided antibody homologs preferably are intact immunoglobulin molecules having two each of heavy and light chains, but may consist of one or more light chains, one or more heavy chains or combinations thereof. In addition, the anti-CD4 antibody homologs of this invention may be in the form of Fab fragments, Fab' fragments, F(ab)$_2$ fragments, F(v) fragments or any other immunoglobulin fragment having the above-described properties.

Provided as preferred anti-CD4 antibody homologs of this invention are the mouse monoclonal antibodies designated 5A8, 1F8 and 5F2. 5A8 is most preferred.

This invention provides DNA sequences encoding the 5A8 heavy chain variable region and the 5A8 light chain variable region. Also provided are DNA sequences encoding 5A8-chimeric and 5A8-humanized recombinant antibodies utilizing those DNA sequences, or portions thereof, as well as the polypeptides encoded by those DNA sequences. Recombinant DNA molecules comprising those DNA sequences and expression control sequences operatively linked thereto are also provided.

This invention provides 5A8-mimetic agents, which are peptides, semi-peptidic compounds or non-peptidic compounds that significantly block binding of monoclonal antibody 5A8 to human CD4. 5A8-mimetic agents of this invention inhibit HIV-induced syncytia formation between $CD4^+$ cells, inhibit infection of $CD4^+$ cells by HIV, or both. Preferably, a 5A8-mimetic agent displays the properties of an antibody homolog of this invention.

The present invention also provides anti-CD4 antibody homologs that are linked to one or more substances selected from antibody homologs and 5A8-mimetic agents of this invention, detectable agents, cytotoxic agents and pharmaceutical agents.

Also provided are cells that produce the antibody homologs of this invention, a process for producing the antibody homologs by culturing those cells, and a process for producing hybridoma cells of this invention by immunizing a non-human mammal with $CD4^+$ cells expressing CD4 on their surface which are produced by transforming $CD4^-$ tissue culture cells with DNA encoding full-length human CD4.

The properties of the anti-CD4 homologs and 5A8-mimetic agents of the present invention make them especially useful in the detection, prophylaxis and treatment in humans of diseases caused by infective agents whose primary targets are $CD4^+$ cells, for example, the HIV-related diseases ARC and AIDS. Accordingly, the present invention provides diagnostic, prophylactic and therapeutic compositions comprising the above-described anti-CD4 antibody homologs and 5A8-mimetic agents, useful for detecting, preventing and treating in humans diseases caused by infective agents whose primary targets are $CD4^+$ cells, for example, the HIV-related diseases ARC and AIDS, as well as methods using these compositions.

BRIEF DESCRIPTION OF THE DRAWINGS

FIG. 3 depicts percent inhibition of syncytia formation (quantified as $^{51}Cr$ release) as a function of antibody concentration (0.026–2,000 ng/ml) for a monoclonal antibody of this invention (5A8) and two CD4 V1-specific monoclonal antibodies (Leu3A and OKT4A).

FIG. 4 depicts percent inhibition of syncytia formation (quantified as $^{51}Cr$ release) as a function of antibody concentration (3.2–10,000 ng/ml) for a monoclonal antibody of this invention (5A8), two CD4 V1-specific monoclonal antibodies (Leu3A and OKT4A) and an "OKT4-like" monoclonal antibody specific for CD4 V3V4 (2~103-D11).

FIGS. 5–6 depict the inhibition of tetanus toxoid ("TT")-induced proliferation of human peripheral blood lymphocytes (quantified as $^3H$-thymidine incorporation and identified as "cpm×10E3 (Thousands)") caused by an antibody homolog of this invention (monoclonal antibody 5A8) and various control antibodies (the CD4 V1-specific antibodies OKT4A and Leu3A and the isotype-matched control antibodies MOPC 21 and UPC 10) on days four (FIG. 5) and five (FIG. 6) of the assay. The bars labelled "TT Control" show the baseline growth of the cells without TT stimulation (open bar) and the TT response without any antibody (solid bar). The effect on proliferation of antibody only, without TT stimulation, is indicated by the bars with large spots. FIGS. 5-6 also show the effect on proliferation after TT stimulation (i.e., inhibition of TT response) caused by the various antibodies at concentrations of 10 µg/ml (bars with dots) (MOPC 21 and 5A8 only), 1 µg/ml (bars with diagonal stripes) (every antibody) and 0.1 µg/ml (bars with crosshatching) (every antibody).

DETAILED DESCRIPTION OF THE INVENTION

Definitions

Figure 1A:
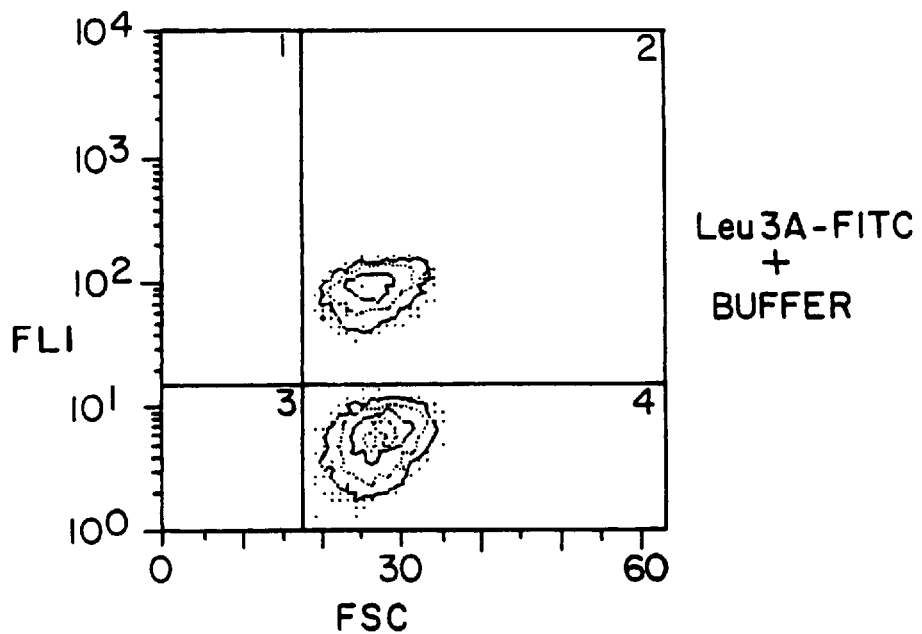
FIGS. 1(A–E) depicts fluorescence activated cell sorter ("FACS"). profiles of human peripheral blood lymphocytes stained with the CD4 V1-specific monoclonal antibody Leu3A labelled with fluorescein isothiocyanate ("Leu3A-FITC") in the presence of buffer (FIG. 1A), unlabelled Leu3A (FIG. 1B), the CD4 V1-specific monoclonal antibody OKT4A (FIG. 1C), the CD4 V3V4-specific monoclonal antibody OKT4 (FIG. 1D) or monoclonal antibody 5A8 of this invention (FIG. 1E). Data are plotted as log fluorescence intensity (y-axis) as a function of forward scatter (x-axis).
Figure 1B:
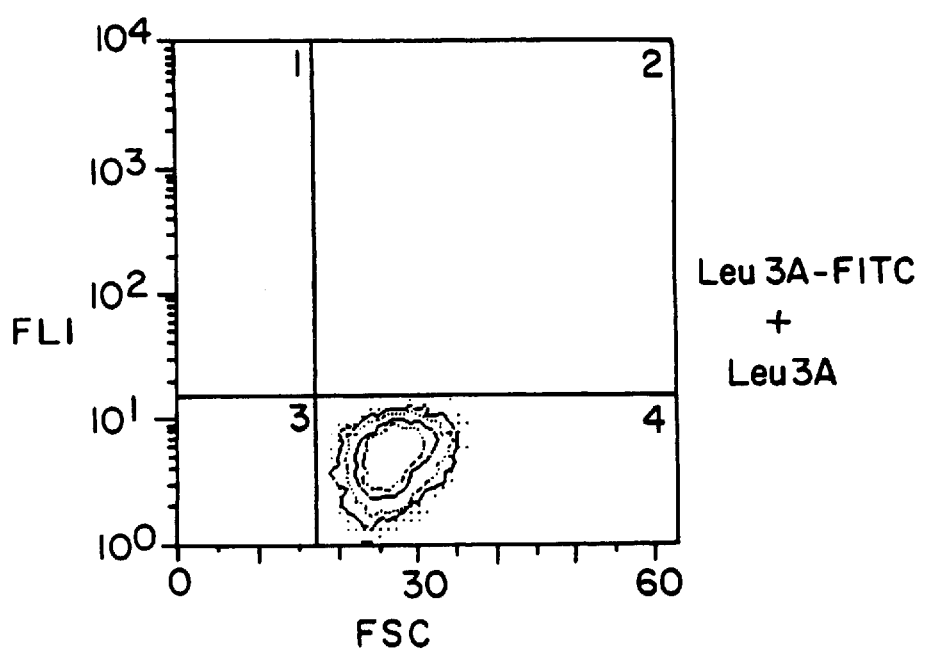
Figure 1C:
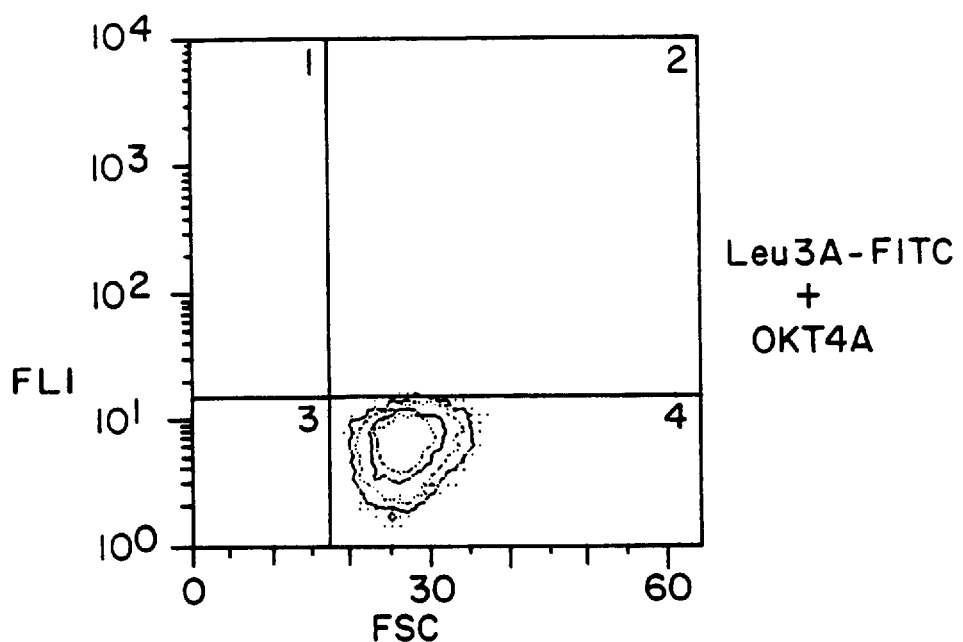
Figure 1D:
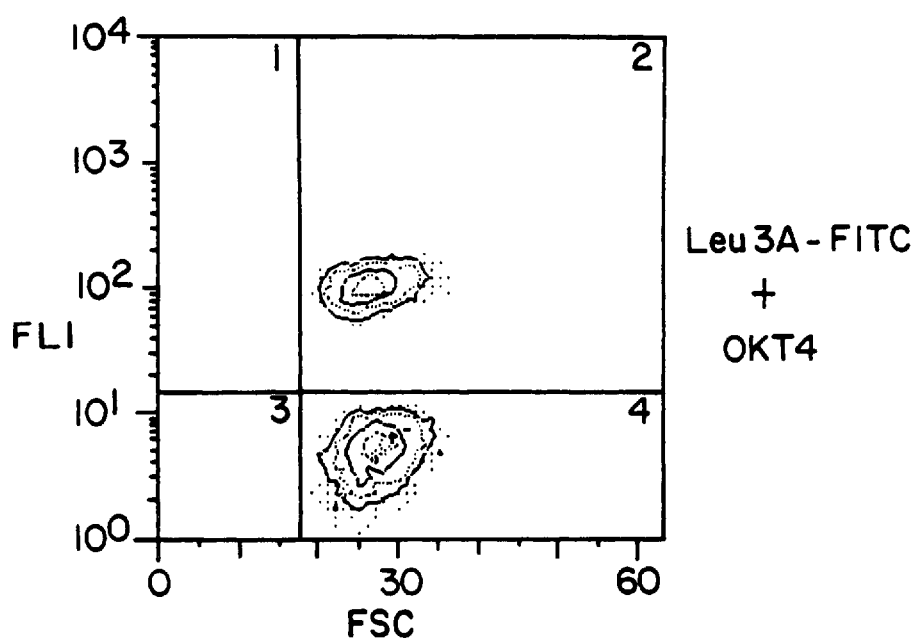
Figure 1E:
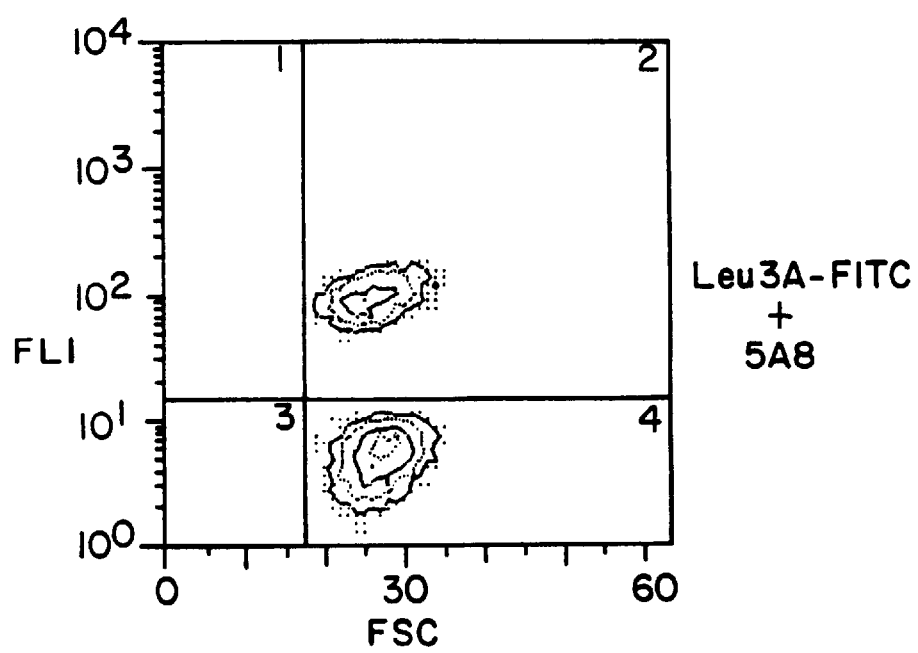
Figure 2A:
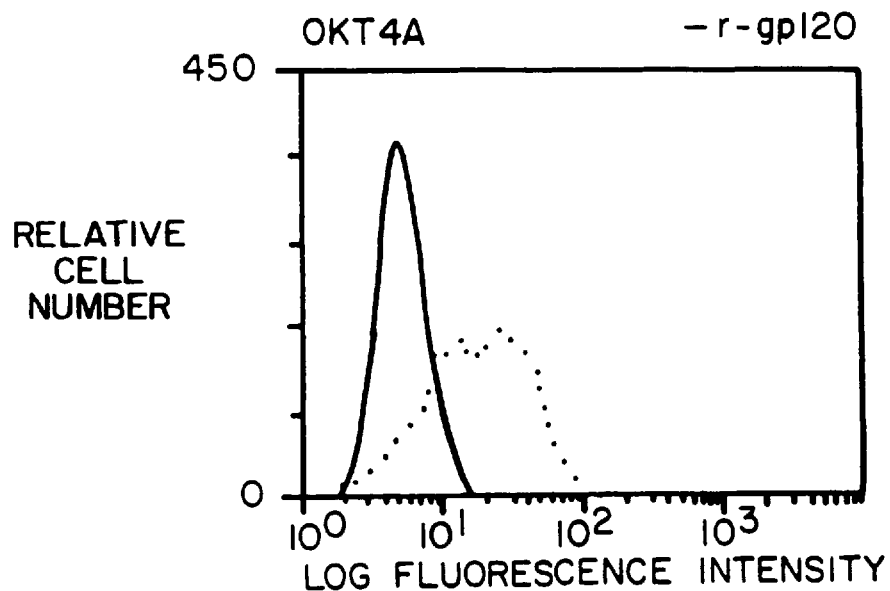
FIGS. 2(A–H) depicts immunofluorescent staining of the human $CD4^+$ cell line H9 with an antibody homolog of this invention 5A8(2E and 2F) and the anti-CD4 monoclonal antibodies Leu3A(2C and 2D), OKT4A(2A and 2B) and OKT4(2G and 2H), with and without preincubation with excess HIV gp120 . The dotted lines signify staining with an anti-CD4 monoclonal antibody and the solid lines signify staining with irrelevant negative control mouse antibodies in the absence (2A, 2C, 2E, 2G) or presence (2B, 2D, 2F, 2H) of excess HIV gp120.
Figure 2B:
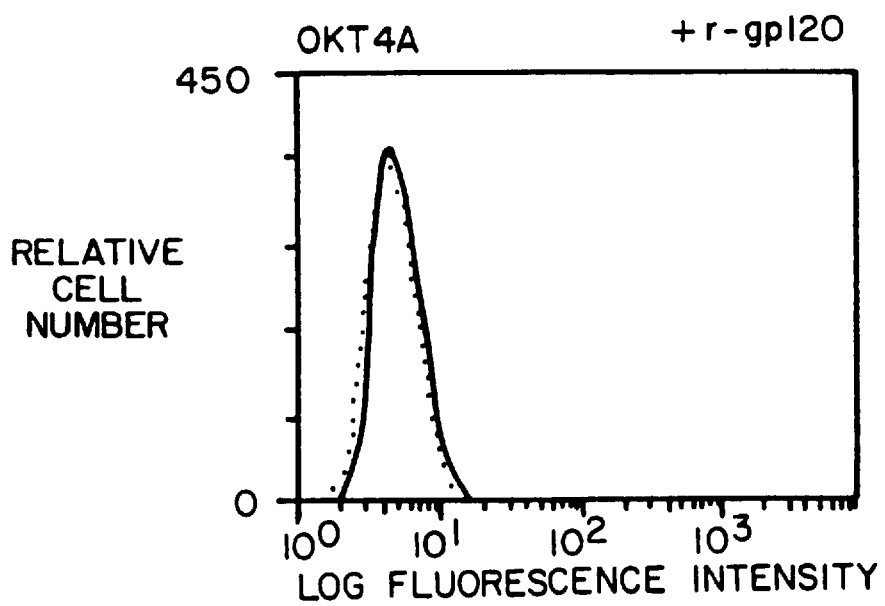
Figure 2C:
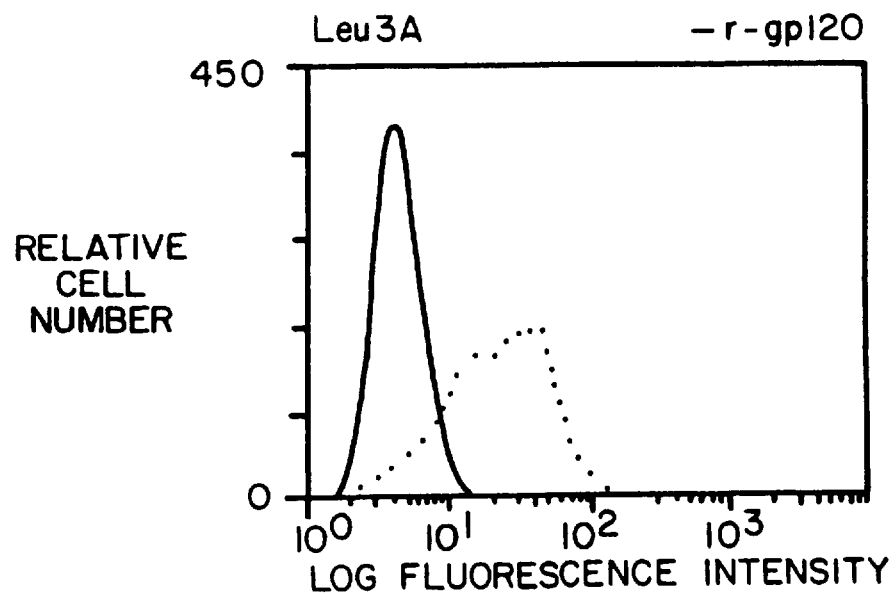
Figure 2D:
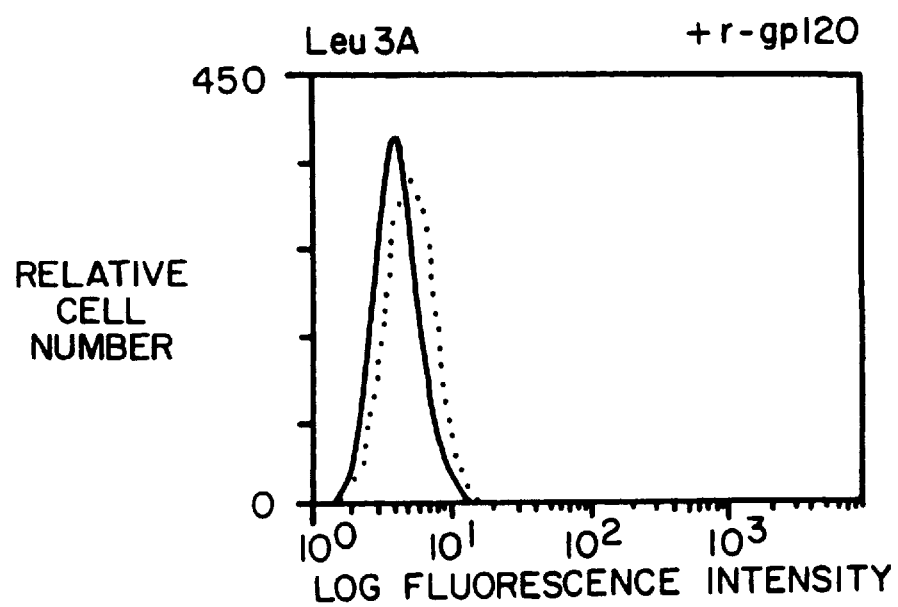
Figure 2E:
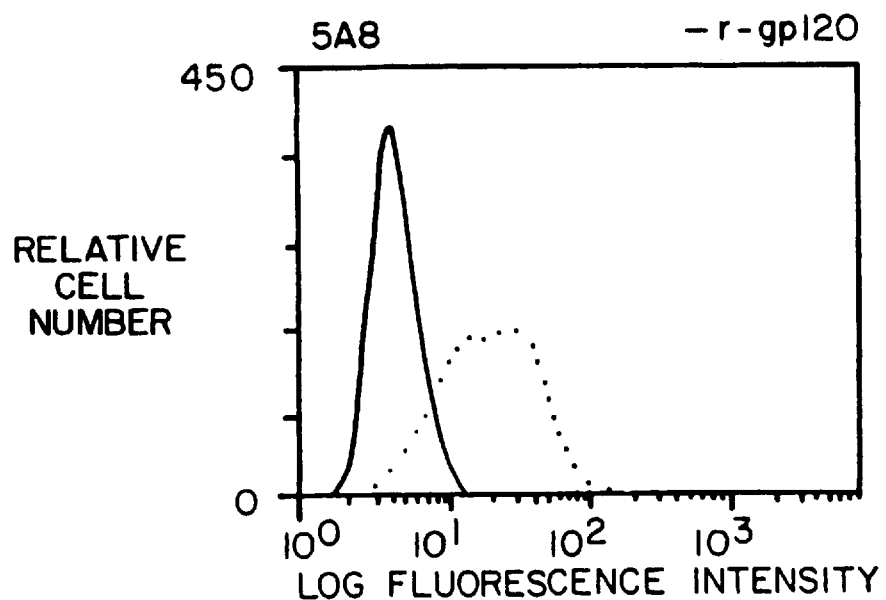
Figure 2F:
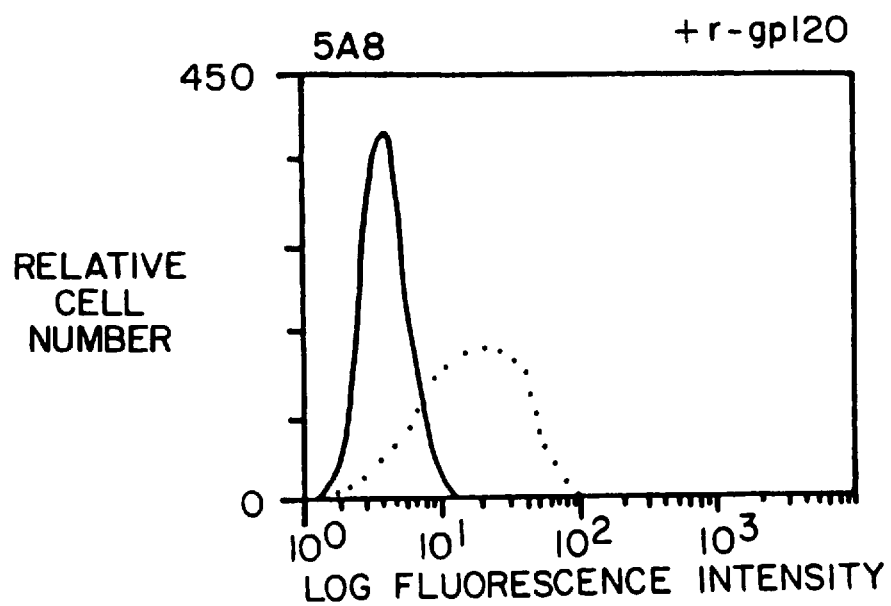
Figure 2G:
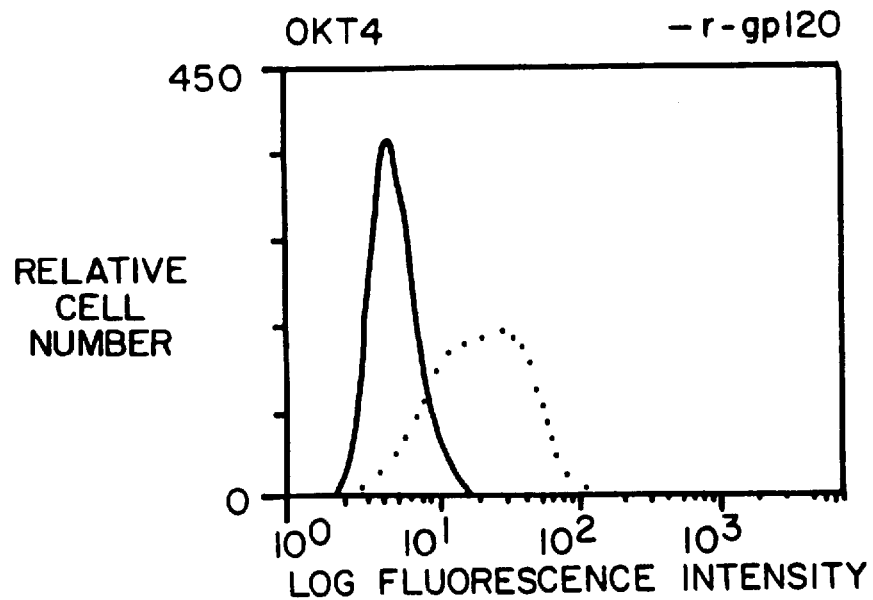
Figure 2H:
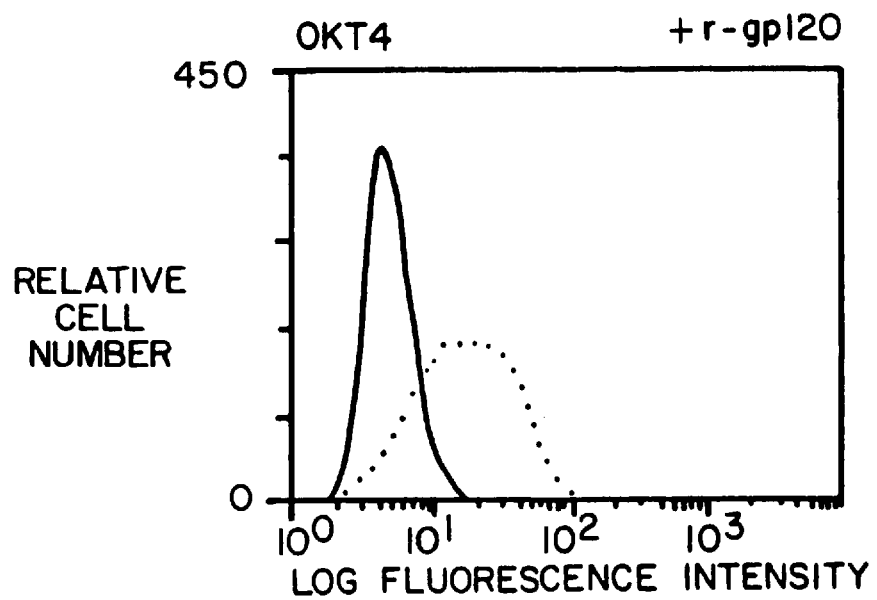

As used herein, "CD4" means any CD4 protein encoded by a naturally occurring CD4 gene.

As used herein, "CD4$^+$ cells" are cells that present the CD4 glycoprotein on their surface. Such cells include CD4$^+$ T lymphocytes and CD4$^+$ mammalian tissue culture cells, e.g., H9 and C8166 cells.

As used herein, "CD4 V1" is the region of CD4 spanning $AA_1$–$AA_{113}$.

As used herein, "CD4 V1V2" is the region of CD4 spanning $AA_1$–$AA_{180}$.

As used herein, "CD4 V3V4" is the region of CD4 spanning $AA_{181}$–$AA_{375}$.

As used herein, "recombinant soluble CD4" or "rsCD4" is a polypeptide consisting of $AA_1$–$AA_{375}$ (i.e., regions V1–V4) of human CD4.

As used herein, a "CD4 V1-specific antibody" is an antibody that binds to an epitope in the V1 region of CD4.

As used herein, a "CD4 V3V4-specific antibody" is an antibody that binds to an epitope in the V3V4 region of CD4.

As used herein, an "antibody homolog" is a protein comprising one or more polypeptides selected from immunoglobulin light chains, immunoglobulin heavy chains, and antigen-binding fragments thereof, which are capable of binding to one or more antigens. The component polypeptides of an antibody homolog composed of more than one polypeptide may optionally be disulfide-bound or otherwise covalently crosslinked. Accordingly, antibody homologs include intact immunoglobulins of types IgA, IgG, IgE, IgD, IgM (as well as subtypes thereof), wherein the light chains of the immunoglobulin may be of types kappa or lambda. Antibody homologs also include portions of intact immunoglobulins that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like.

As used herein, a "humanized recombinant antibody homolog" is an antibody homolog initially derived from a nonhuman mammal in which recombinant DNA technology has been used to substitute some or all of the amino acids not required for CD4 binding with amino acids from corresponding regions of a human immunoglobulin light or heavy chain.

As used herein, a "chimeric recombinant antibody homolog" is an antibody homolog derived initially from a nonhuman mammal, in which recombinant DNA technology has been used to replace all or part of the hinge and constant regions of the light chain, the heavy chain or both, with corresponding regions from an immunoglobulin light chain or heavy chain of a mammal of a different species, preferably a human.

As used herein, an antibody homolog that "does not significantly block binding of a CD4 V1-specific antibody to human CD4" is one that causes no more than a 30% reduction in the binding of the CD4 V1-specific antibody either to human rsCD4 (CD4 V1–V4) or to human CD4 displayed on a CD4$^+$ cell.

As used herein, an antibody homolog that "does not significantly block binding of HIV gp120 to human CD4" is one that causes no more than a 30% reduction in the binding of HIV gp120 either to human rsCD4 (CD4 V1–V4) or to human CD4 displayed on a CD4$^+$ cell.

As used herein, "OKT4" is the anti-CD4 mouse monoclonal antibody commercially available from Ortho Diagnostic Systems, Raritan, N.J. under catalog number 7042.

As used herein, "OKT4A" is the anti-CD4 mouse monoclonal antibody commercially available from Ortho Diagnostic Systems, Raritan, N.J. under catalog number 7142.

As used herein, a "5A8-mimetic agent" is a compound that causes at least a 30% reduction in the binding of monoclonal antibody 5A8 either to human rsCD4 (CD4 V1–V4) or to human CD4 displayed on a CD4$^+$ cell.

As used herein, an antibody homolog "causing no significant decrease in the number of circulating CD4$^+$ cells in vivo" is an antibody homolog which, within 24 hours after administration to a mammal having normal immune function, causes less than a 50% decrease in the number of circulating CD4$^+$ cells, as compared either to the pre-administration number for that mammal or to the number in a control mammal to whom an isotype-matched antibody homolog of irrelevant specificity has been administered instead of an antibody homolog of this invention.

As used herein, an antibody homolog "causing no significant modulation of CD4 from the surface of CD4$^+$ cells in vivo" is an antibody homolog which, within 24 hours after administration to a mammal having normal immune function, causes less than a ten-fold decrease in the number of CD4 molecules on the surface of the mammal's CD4$^+$ cells, as compared either to the pre-administration number for that mammal or to the number in a control mammal to whom an isotype-matched antibody homolog of irrelevant specificity has been administered instead of an antibody homolog of this invention.

As used herein, an antibody homolog "causing no significant decrease in circulating peripheral white blood cell counts in vivo" is an antibody homolog which, within 24 hours after administration to a mammal having normal immune function, causes less than a 50% decrease in the number of circulating peripheral white blood cells, as compared either to the pre-administration number for that mammal or to the number in a control mammal to whom an isotype-matched antibody homolog of irrelevant specificity has been administered instead of an antibody homolog of this invention. In this context, "peripheral white blood cells" include B lymphocytes, T lymphocytes (CD4$^+$ or CD8$^+$) and monocytes.

As used herein, an antibody homolog "causing no significant decrease in the antibody titer elicited in response to foreign antigens" is an antibody homolog which, upon administration to a mammal having normal immune function, causes less than a ten-fold decrease in the antibody titer elicited in response to a subsequently administered foreign antigen, as compared to the antibody titer elicited by the foreign antigen in a control mammal to whom an isotype-matched antibody homolog of irrelevant specificity has been administered instead of an antibody homolog of this invention. In this context, a "foreign antigen" is a molecule (e.g., a viral or bacterial polypeptide) that is not encoded by the genome of that mammal.

Antibody Homologs According To This Invention

The antibody homologs according to one embodiment of the present invention (a) bind to human CD4; (b) do not significantly block binding of HIV gp120 to human CD4; and (c) block HIV-induced syncytia formation between CD4$^+$ cells at least about as well as OKT4A.

Another embodiment of the present invention relates to antibody homologs that (a) bind to human CD4; (b) do not significantly block binding of HIV gp120 to human CD4; (c) block HIV-induced syncytia formation between CD4+ cells better than OKT4; and (d) are less immunosuppressive than OKT4A in an in vitro tetanus toxoid-specific proliferation assay.

A further embodiment relates to antibody homologs that (a) bind to human CD4; (b) do not significantly block binding of HIV gp120 to human CD4; (c) block HIV-induced syncytia formation between CD4+ cells at least about as well as OKT4A and (d) are less immunosuppressive than OKT4A in an in vitro tetanus toxoid-specific proliferation assay.

Certain of the antibody homologs of this invention bind to a polypeptide consisting of human CD4 V1V2 (i.e., they are V1V2-specific), but do not bind to a polypeptide consisting of human CD4 V1 (i.e., they are not solely V1-specific). Similarly, certain antibody homologs of this invention do not significantly block the binding of CD4 V1-specific antibodies, such as OKT4A and Leu3A, to human CD4.

The preferred antibody homologs of this invention inhibit infection of CD4+ cells by HIV.

Other preferred antibody homologs of this invention display one or more characteristics selected from: (a) causing no significant decrease in the number of circulating CD4+ cells in vivo; (b) causing no significant modulation of CD4 from the surface of CD4+ cells in vivo; (c) causing no significant decrease in circulating peripheral white blood cell counts in vivo; (d) causing no significant decrease in the antibody titer elicited in response to foreign antigens in vivo; and (e) causing no consistent or persistent inhibition ex vivo of T cell proliferative responses to mitogens and xenogeneic cells.

The most preferred antibody homologs of this invention display all of the above-described properties.

Specific antibody homologs according to the present invention include the mouse monoclonal antibodies designated 5A8 ($IgG_1$) 1F8 ($IgG_1$) and 5F2 ($IgG_1$), described infra. 5A8 is preferred.

While not wishing to be bound by theory, we believe that the antibody homologs of this invention are prophylactic and therapeutic for AIDS, ARC and HIV infection because they inhibit HIV-induced syncytia formation between CD4+ cells, thus slowing spread of the virus to uninfected cells. We believe the antibody homologs of this invention to be particularly useful because they should prevent syncytia formation even after HIV gp120 has bound to CD4 displayed at the surface of CD4+ lymphocytes. The antibody homologs of this invention that also inhibit infection of CD4+ cells by HIV are particularly useful. Furthermore, because the antibody homologs of this invention are non-competitive blockers of virus binding, we believe their therapeutic and prophylactic effects to be independent of plasma virus levels.

Screening Assays For Antibody Homologs According To This Invention

The ordinary skilled worker may easily determine, using well known methods, whether a particular antibody homolog (or preparation comprising an antibody homolog) displays the properties described above, and thus may identify antibody homologs according to the present invention.

To determine whether a particular antibody homolog binds to human CD4, any conventional binding assay may be used. Useful CD4 binding assays include FACS analysis, ELISA assays, radioimmunoassays and the like, which detect binding of antibody homologs to human CD4. Full-length and soluble forms of human CD4 useful in such assays are described in PCT patent application PCT/US88/02940, which is herein incorporated by reference. Reference should also be made to D. R. Littman et al., Cell, 55, p. 541 (1988), which describes the correct signal sequence cleavage site of pre-human CD4 and which was published after the filing date of PCT/US88/02940. The binding of an antibody homolog to CD4, or to soluble fragments thereof, such as rsCD4, may conveniently be detected through the use of a secondary antibody specific for immunoglobulins of the species from which the antibody homolog was derived.

To determine whether a particular antibody homolog does not significantly block binding of HIV gp120 to human CD4, any suitable competition assay may be used. Useful assays include, for example, ELISA assays, radioimmunoassays and the like that quantify the ability of the antibody homolog to cross block with HIV gp120 for binding to human CD4. Preferably, the ability of excess HIV gp120 to block binding of labelled human rsCD4 to immobilized antibody homolog is measured.

Preferably, the ability of an antibody homolog to bind to human CD4 is evaluated by testing its ability to bind to human CD4+ cells. The preferred CD4+ cells for use in determining whether a particular antibody homolog binds to human CD4 are mammalian tissue culture cells transformed with DNA encoding full-length human CD4 and expressing the CD4 on their surface. Such cells include, for example, the CHO cells transformed with DNA encoding full-length CD4 which are described in R. A. Fisher et al., "HIV Infection Is Blocked In vitro By Recombinant Soluble CD4", Nature, 331, pp. 76–78 (1988) ("r-CD4-CHO cells"). Suitable r-CD4-CHO cells were deposited with the In Vitro International, Inc. culture collection in Linthicum, Md., under accession number IVI-10260 and transferred to the American Type Culture Collection, Rockville, Md., under accession number CRL 10884.

Binding of the antibody homolog to the CD4+ cell preferably is detected by staining the cells with a fluorescently labelled secondary antibody specific for immunoglobulins of the same species from which the antibody homolog being tested is derived. A fluorescence activated cell sorter ("FACS") is used to detect and quantify any binding. See generally H. M. Shapiro, Practical Flow Cytometry, Alan R. Liss, Inc., New York, N.Y. (1985).

Most preferably, the ability of an antibody homolog to block binding of HIV gp120 to human CD4 is determined by preincubating excess HIV gp120 with CD4+ cells, and quantifying the degree to which the bound HIV gp120 blocks binding of the antibody homolog to the cells. Binding of the antibody homolog to the CD4+ cells is quantified by FACS analysis, using a fluorescently labelled secondary antibody specific for immunoglobulins of the same species from which the antibody homolog being tested is derived.

The HIV gp120 used in the above assays may be provided by cells infected with HIV, by HIV itself, by host cells transformed with the gene for HIV gp120 , or by isolated gp120. Preferably, a purified, soluble HIV gp120 isolated from a unicellular host transformed with a truncated HIV gp160 gene encoding HIV gp120 will be used. Purified, recombinant HIV gp120 is commercially available, for example, from Repligen (Cambridge, Mass.) and from Celltech (Berkshire, United Kingdom). Cells producing recombinant gp120 are described, for example, in Lasky et al., "Neutralization Of The AIDS Retrovirus By Antibodies To A Recombinant Envelope Glycoprotein", Science, 233, pp. 209–12 (1986). Suitable soluble, recombinant HIV gp120 polypeptides are produced by Spodoptera frugiperda cells transformed with recombinant baculovirus carrying the DNA sequence defined by SEQ ID NO:3.

To determine whether a particular antibody homolog blocks HIV-induced syncytia formation between CD4+ cells better than OKT4 or at least about as well as OKT4A, any known syncytia assay may be used. Preferably, an HIV laboratory isolate or HIV-infected CD4+ tissue culture cells (e.g., H9) are added to cultures of C8166 cells, and varying amounts of the antibody homolog are added to all but the control cultures. To control cultures are added similar varying amounts of OKT4 or OKT4A. Some control cultures (negative controls) are supplemented with nothing, or with an irrelevant antibody of the same isotype as the antibody homolog. After incubation, all the cultures are scored by visual inspection for syncytia. In this way, the ability of the antibody homolog to block syncytia formation is compared to the syncytia blocking abilities of OKT4 and OKT4A.

An alternative method for comparing the syncytia blocking abilities of an antibody homolog with that of OKT4 and OKT4A is the following. Transformed tissue culture cells expressing recombinant HIV envelope glycoprotein (i.e., HIV gp120/gp41 after post-translational cleavage of HIV gp160) on their surface are incubated with human CD4+ cells containing a detectable substance (e.g., Jurkat cells labelled with $^{51}$Cr) in the presence of OKT4, OKT4A, antibody homolog to be tested or no antibody. After incubation, the culture supernatants are assayed for the detectable substance (e.g., measuring τ-irradiation for $^{51}$Cr). Cell lysis is an inevitable sequela to HIV-induced syncytia formation. Therefore, the amount of detectable substance released into a culture supernatant as a consequence of cell lysis is directly proportional to syncytia formation. In this way, the degrees to which OKT4, OKT4A and a particular antibody homolog block syncytia formation are easily quantified and compared.

The most preferred transformed tissue culture cell for the above assay is a CHO cell expressing recombinant HIV envelope glycoprotein on its surface ("r-gp160-CHO cell"). Such r-gp160-CHO cells are exemplified by cultures which were deposited in the In Vitro International, Inc. culture collection, Linthicum, Md., under accession number IVI-10261 and transferred to the American Type Culture Collection, Rockville, Md., under accession number CRL 10885. The deposited cells are transformed with the DNA sequence defined herein by SEQ ID NO:1.

To determine whether a particular antibody homolog is less immunosuppressive than OKT4A in an in vitro tetanus toxoid-specific proliferation assay, the general protocol described in E. G. Engleman et al., "Activation Of Human T Lymphocyte Subsets: Helper And Suppressor/Cytotoxic T Cells Recognize And Respond to Distinct Histocompatibility Antigens", *J. Immunol.*, 127, pp. 2124–29 (1981) is preferred. In such a tetanus toxoid assay, the ability of antibody homologs and OKT4A to reduce tetanus toxoid-induced T cell proliferation is quantified. Typically, proliferation is measured by $^3$H-thymidine incorporation by the T cells.

To determine whether a particular antibody homolog either does not bind to a polypeptide consisting of the human CD4 V1 region or whether it does bind to a polypeptide consisting of the human CD4 V1V2 region, ELISA assays, radioimmunoassays (RIAs), FACS analysis or the like are useful. In such assays, the ability of the antibody homolog to bind to either of those polypeptides may be detected through use of a secondary antibody specific for immunoglobulins of the species from which the antibody homolog was derived.

Preferably, binding is determined through inhibition studies with CD4 V1 and CD4 V1V2 polypeptides as competitors for binding of the antibody homolog to human CD4 displayed on the surface of a CD4+ cell, using FACS analysis to quantify any inhibition.

Alternatively, determining whether a particular antibody homolog binds or does not bind to a CD4 V1 polypeptide or CD4 V1V2 polypeptide is accomplished using an RIA competition assay in which the antibody homolog is bound to the plate (directly or indirectly), and the CD4 V1 polypeptide or CD4 V1V2 polypeptide simultaneously competes with detectably labelled rsCD4 for binding to the antibody homolog. The amount of bound rsCD4 is compared with the amount of rsCD4 bound in the absence of the CD4 V1 or CD4 V1V2 polypeptide, allowing calculation of the percent inhibition of rsCD4 binding caused by the CD4 V1 or CD4 V1V2 polypeptide.

The preferred polypeptides consisting of the human CD4 V1 or CD4 V1V2 regions are CD4 $AA_3$–$AA_{15}$ or CD4 $AA_3$–$AA_{182}$, respectively, of the CD4 sequences set forth in PCT patent application PCT/US88/02940 or in Maddon et al., Cell, supra. Using the corrected numbering system of Littman et al., Cell, supra, these polypeptides correspond respectively to human CD4 $AA_1$–$AA_{113}$ and human CD4 $AA_1$–$AA_{180}$. A suitable CD4 V1 polypeptide is described in B. H. Chao et al., "A 113-Amino Acid Fragment Of CD4 Produced In *Escherichia coli* Blocks Human Immunodeficiency Virus-Induced Cell Fusion", *J. Biol. Chem.*, 264, pp. 5812–17 (1989). A suitable CD4 V1V2 polypeptide is described in R. L. Garlick et al., "*Escherichia coli* Expression, Purification, And Biological Activity Of A Truncated Soluble CD4", *AIDS Res. Hum. Retroviruses*, 6, pp. 465–79 (1990).

To determine whether a particular antibody homolog inhibits infection of CD4+ cells by HIV, any indication of HIV infection could be monitored. Useful indicators of HIV infection include, for example, secretion of HIV core antigen p24 by cells chronically infected by HIV and HIV-induced syncytia formation. Preferably, inhibition of HIV infection is determined by comparing HIV p24 levels in the presence and absence of the antibody homolog in HIV-infected CD4+ cell cultures.

To determine whether a particular antibody homolog causes no significant decrease in the number of circulating CD4+ cells in vivo, the number of circulating CD4+ cells isolated from a mammal within 24 hours after administration of the antibody homolog to a mammal having normal immune function is quantified, and compared to the pre-administration number or the number in a control mammal to whom an isotype-matched antibody homolog of irrelevant specificity has been administered instead of an antibody homolog of this invention. Quantification of CD4+ cells may be accomplished, for example, by staining the cells with fluorescently labelled anti-CD4 antibodies that do not cross block with the antibody homolog for binding to CD4 (e.g., OKT4), followed by FACS analysis.

To determine whether a particular antibody homolog causes no significant modulation of CD4 from the surface of CD4+ cells in vivo, the number of CD4 molecules on CD4+ cells isolated from a mammal within 24 hours after administration of the antibody homolog to a mammal having normal immune function is quantified, and compared to the pre-administration number in that mammal or the number in a control mammal to whom an isotype-matched antibody homolog of irrelevant specificity has been administered instead of an antibody homolog of this invention. Quantification of cell surface CD4 may be accomplished, for example, by staining the cells with fluorescently labelled anti-CD4 antibodies that do not cross block with the antibody homolog for binding to CD4 (e.g., OKT4), followed by FACS analysis.

To determine whether a particular antibody homolog causes no significant decrease in circulating peripheral white blood cell counts in vivo, blood drawn within 24 hours after administration of the antibody homolog to a mammal having normal immune function is fractionated by conventional means and white blood cell counts are obtained (e.g., by staining blood smears). That number is compared to the pre-administration number for that mammal or to the number in a control mammal to whom an isotype-matched antibody of irrelevant specificity has been administered instead of an antibody homolog of this invention.

To determine whether a particular antibody homolog causes no significant decrease in the antibody titer elicited in response to foreign antigens in vivo, the antibody titer elicited in a mammal having normal immune function by a foreign antigen is determined after administration of the antibody homolog, and compared to the titer elicited in a control mammal to whom an isotype-matched antibody homolog has been administered instead of an antibody homolog of this invention. The antibody titer for the foreign antigen may conveniently be determined, for example, by performing an ELISA using microtiter plates coated with the foreign antigen.

To determine whether a particular antibody homolog causes no significant inhibition in vitro of T cell proliferative responses to mitogens and xenogeneic cells the proliferative responses of T cells isolated before and at various time points after administration of antibody homolog is measured.

Useful mitogens for this purpose include Concanavalin A and phytohemagglutinin. Useful xenogeneic cells include any cells (e.g., lymphocytes) derived from a species other than the species of the mammal to which the antibody homolog was administered. Proliferative response may be measured, for example, by $^3$H-thymidine incorporation into the various T cell samples after incubation in vitro with mitogens or irradiated xenogeneic cells, which cannot proliferate.

Types Of Antibody Homologs According To This Invention- And Their Production

Antibody homologs according to the present invention may be of many types, the critical criterion being that the antibody homolog display one of the combinations of properties described above. For example, antibody homologs of this invention may be intact monoclonal antibodies, intact recombinant antibodies, intact chimeric recombinant antibodies, intact humanized recombinant antibodies, or antigen-binding portions of the foregoing antibodies.

A. Monoclonal Antibodies

The most preferred antibody homologs of the present invention are intact monoclonal antibodies produced by hybridoma cells. The technology for producing monoclonal antibodies is well known [see generally E. A. Lerner, "How To Make A Hybridoma", *Yale J. Biol. Med.*, 54, pp. 387–402 (1981); M. L. Gefter et al., "A Simple Method For Polyethylene Glycol-Promoted Hybridization Of Mouse Myeloma Cells", *Somatic Cell Genet.*, 3, pp. 231–36 (1977)]. Briefly, an immortal cell line (typically myeloma cells) is fused to lymphocytes (typically splenocytes) from a mammal immunized with a preparation comprising human CD4 or a VIV2-containing fragment thereof, and the culture supernatants of the resulting hybridoma cells are screened as described above for antibody homologs according to this invention.

Useful CD4-comprising preparations include human CD4-bearing cells (e.g., CD4$^+$ lymphocytes), fractions of such cells comprising CD4, partially purified or substantially pure human CD4 isolated from natural sources, and unpurified, partially purified or substantially pure human CD4 or V1V2-containing fragments thereof derived from recombinant host cells. Recombinant host cells expressing V1V2-containing fragments of CD4 are described, for example, in PCT patent application PCT/US88/02940.

The preferred immunogen is CD4$^+$ cells produced by transforming CD4- mammalian tissue culture cells with DNA encoding full-length human CD4. Most preferably, the immunogen is a CHO cell transformed with the DNA sequence encoding CD4 $AA_{-23}$–$AA_{435}$ set forth in Maddon et al., *Cell*, supra (i.e., CD4 $AA_{-25}$–$AA_{433}$ using the corrected numbering system set forth in Littman et al., *Cell*, supra). Such a cell, referred to herein as an "r-CD4-CHO cell", was deposited with the In Vitro International, Inc. culture collection, Linthicum, Md., under accession number IVI-10260 and transferred to the American Type Culture Collection, Rockville, Md., under accession number CRL 10884 [see also Fisher et al., *Nature*, supra].

While not wishing to be bound by theory, we believe that using r-CD4-CHO cells as the immunogen, rather than "natural" CD4$^+$ cells, isolated CD4 or truncated forms of CD4 (e.g., rsCD4), increases the likelihood of obtaining anti-CD4 antibody homologs according to the present invention from a particular fusion. We believe this increased likelihood as compared to "natural" CD4$^+$ cells to be due possibly to the fact that there are no naturally occurring T cell surface molecules other than CD4 displayed on the surface of the r-CD4-CHO cells which, if present, might associate with the CD4 and by virtue of that association render certain CD4 epitopes inaccessible. We believe this increased likelihood as compared to isolated CD4 or fragments thereof to be due possibly to a more favorable conformation assumed by the CD4 on the surface of the r-CD4-CHO cells than that assumed by isolated CD4 and fragments thereof.

Immunization may be accomplished using standard procedures. The unit dose and immunization regimen depend on the species of mammal immunized, its immune status, the body weight of the mammal, and the CD4 content of the CD4 preparation administered. Typically, the CD4 preparation will be administered with an adjuvant, such as complete or incomplete Freund's adjuvant.

In the preferred embodiment, each dose of the CD4 preparation used for immunization of mice contains at least about $2 \times 10^5$ cells, preferably about $3 \times 10^6$ to $2 \times 10^7$ r-CD4-CHO cells. Most preferably, a unit dose contains about $5 \times 10^6$ r-CD4-CHO cells. Typically, the mouse is immunized intraperitoneally on day 0 with r-CD4-CHO cells in complete Freund's adjuvant. The mouse is given a first boost intraperitoneally with r-CD4-CHO cells without adjuvant, 14 days to 6 months after the initial immunization, and preferably 15 to 20 days after the first immunization. Additional boosts may be administered if desired. Three days before fusion, the final boost (r-CD4-CHO cells without adjuvant) is administered intravenously. Typically, this final boost is administered 1 to 6 months, and preferably 39–44 days, after the initial immunization. Three days after the final boost, the mammal is sacrificed, its spleen removed and the splenocytes (including lymphocytes) are prepared for fusion with the immortal cell line.

The immunized mammals may be bled between boosts and the serum from each blood sample assayed for antibody homologs according to the present invention using the screening assays described above. The lymphocytes used in the production of hybridoma cells typically are isolated from immunized mammals whose sera have already tested positive for the presence of antibody homologs according to this invention.

Any of the many well known protocols used for fusing lymphocytes and immortalized cell lines would be useful for the purpose of generating antibody homologs of this invention [see, e.g., G. Galfre et al., "Antibodies To Major Histocompatibility Antigens Produced By Hybrid Cell Lines", Nature, 266, pp. 550–52 (1977); Gefter et al., Somatic Cell Genet., supra; Lerner, Yale J. Biol. Med., supra]. Moreover, the ordinary skilled worker will appreciate that there are many variations of such methods which also would be useful.

Typically, the immortal cell line (e.g., a myeloma cell line) is derived from the same mammalian species as the lymphocytes. Useful mammals include mice and rats.

Most preferably, both the immortal cell line and the lymphocytes are derived from an inbred mouse of strain BALB/c (Jackson Labs, Bar Harbour, Me.). Preferred immortal cell lines are mouse myeloma cell lines that are sensitive to culture medium containing hypoxanthine, aminopterin and thymidine ("HAT medium"). The most preferred mouse myeloma cell line is P3X63-AG8.653 (ATCC, Rockville, Md., catalog no. CRL 1580). Typically, HAT-sensitive mouse myeloma cells are fused to mouse splenocytes using polyethylene glycol ("PEG"), preferably PEG-3350. Hybridoma cells resulting from the fusion are then selected using HAT medium, which kills unfused and unproductively fused myeloma cells (unfused splenocytes die after several days because they are not transformed).

Hybridoma cells producing an antibody homolog (monoclonal antibody) according to the present invention are detected by screening the hybridoma culture supernatants using the screening assays described above. Preferably, the primary screen will select antibodies that bind to human CD4 displayed on the surface of $CD4^+$ cells. Such binding is detected by use of fluorescently labelled secondary antibodies specific for mouse immunoglobulins, and quantified by FACS analysis.

To produce antibody homologs of this invention which are intact monoclonal antibodies, hybridoma cells that have tested positive in the above screening assays are cultured in a nutrient medium under conditions and for a time sufficient to allow the hybridoma cells to secrete the monoclonal antibodies into the culture medium. Tissue culture techniques and culture media suitable for hybridoma cells are well known [see, e.g., Lerner, Yale J. Biol. Med., supra]. Conditioned hybridoma culture supernatant containing the antibody homologs is collected.

Alternatively, the desired antibody homolog may be produced by injecting the hybridoma cells into the peritoneal cavity of an unimmunized mouse. The hybridoma cells proliferate in the peritoneal cavity, secreting the antibody homolog, which accumulates as ascites fluid [see Lerner, Yale J. Biol. Med., supra]. The antibody homolog is harvested by withdrawing the ascites fluid from the peritoneal cavity with a syringe.

It will be understood by the ordinary skilled worker that monoclonal antibodies which are antibody homologs according to this invention may be purified with ease from conditioned hybridoma culture supernatant or from ascites.

B. Recombinant Antibodies And DNA Encoding Them

Antibody homologs according to the present invention may be recombinant monoclonal antibodies produced by host cells transformed with DNA encoding immunoglobulin light and heavy chains according to this invention. Recombinant antibodies may be produced by well known genetic engineering techniques. See, e.g., U.S. Pat. No. 4,816,397, which is incorporated herein by reference.

For example, recombinant antibodies may be produced by cloning cDNA or genomic DNA encoding the immunoglobulin light and heavy chains of the desired antibody from a hybridoma cell that produces an antibody homolog according to this invention. The cDNA or genomic DNA encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector.

This invention provides DNA sequences encoding the 5A8 light chain variable region (SEQ ID NO:14) and the 5A8 heavy chain variable region (SEQ ID NO:9), portions thereof that encode an antibody homolog according to this invention, and DNA sequences degenerate to any of those DNA sequences. Also provided are recombinant DNA molecules comprising one or more of the foregoing DNA sequences and one or more expression control sequences operatively linked thereto.

Prokaryotic or eukaryotic cells may be used as expression hosts. Expression in eukaryotic host cells is preferred because such cells are more likely than prokaryotic cells to assemble and secrete a properly folded and immunologically active antibody. However, any antibody produced that is inactive due to improper folding may be renaturable according to well known methods [P. S. Kim and R. L. Baldwin, "Specific Intermediates In The Folding Reactions Of Small Proteins And The Mechanism Of Protein Folding", Ann. Rev. Biochem., 51, pp. 459–89 (1982)]. It is possible that the host cells will produce portions of intact antibodies, such as light chain dimers or heavy chain dimers, which also are antibody homologs according to the present invention.

It will be understood that variations on the above procedure are within the scope of the present invention. For example, it may be desired to transform a host cell with DNA encoding either the light chain or the heavy chain (but not both) of an antibody homolog of this invention. Recombinant DNA technology may also be used to remove some or all of the DNA encoding either or both of the light and heavy chains that is not necessary for CD4 binding. The molecules expressed from such truncated DNA molecules are antibody homologs according to this invention. In addition, bifunctional antibodies may be produced in which one heavy and one light chain are antibody homologs of this invention and the other heavy and light chain are specific for an antigen other than CD4, or another epitope of CD4.

C. Chimeric And Humanized Recombinant Antibodies And DNA Encoding Them

DNA encoding the recombinant antibodies described above may be used as the starting point for producing chimeric or humanized recombinant antibodies. Chimeric recombinant antibodies are produced by transforming a host cell with a suitable expression vector comprising DNA encoding the desired immunoglobulin light and heavy chains in which all or some of the DNA encoding the hinge and constant regions of the heavy and/or the light chain have been substituted with DNA from the corresponding region of an immunoglobulin light or heavy chain of a different species. When the original recombinant antibody is nonhuman, substitution of corresponding human sequences is preferred. An exemplary chimeric recombinant antibody has mouse variable regions and human hinge and constant regions. See generally, U.S. Pat. No. 4,816,397 and S. L.

Morrison et al., "Chimeric Human Antibody Molecules: Mouse Antigen-Binding Domains With Human Constant Region Domains", *Proc. Natl. Acad. Sci. USA*, 81, pp. 6851–55 (1984).

In the preferred 5A8 chimeric recombinant antibody homologs of this invention, the amino acid sequence of the light chain variable region is EQ ID NO:15 and the amino acid sequence of the heavy chain variable region is SEQ ID NO:10, respectively.

Humanized recombinant antibodies are produced by transforming a host cell with a suitable expression vector comprising DNA encoding the desired nonhuman immunoglobulin light and heavy chains in which all or some of the DNA encoding amino acids not involved in CD4 binding have been substituted with DNA from the corresponding region of a desired human immunoglobulin light or heavy chain. See generally, P. T. Jones et al., "Replacing The Complementarity-Determining Regions In A Human Antibody With Those From A Mouse", *Nature*, 321, pp. 522–25 (1986).

The most preferred humanized recombinant antibodies of this invention have the 5A8 complementarity determining regions ("CDRs"). These include humanized recombinant antibodies wherein:
(a) light chain CDR1 is $AA_{24}$–$AA_{40}$ of SEQ ID NO:15;
(b) light chain CDR2 is $AA_{56}$–$AA_{62}$ of SEQ ID NO:15;
(c) light chain CDR3 is $AA_{95}$–$AA_{102}$ of SEQ ID NO:15;
(d) heavy chain CDR1 is $AA_{31}$–$AA_{35}$ of SEQ ID NO:10;
(e) heavy chain CDR2 is $AA_{50}$–$AA_{66}$ of SEQ ID NO:10; and
(f) heavy chain CDR3 is $AA_{99}$–$AA_{111}$ of SEQ ID NO:10.

Another preferred embodiment provides humanized recombinant antibody homologs having 5A8 CDRs wherein the amino acid sequence of the light chain variable region is $AA_{1}$–$AA_{112}$ of SEQ ID NO:56 and the amino acid sequence of the heavy chain variable region is $AA_{1}$–$AA_{122}$ of SEQ ID NO:45.

A further preferred embodiment provides humanized recombinant antibody homologs having 5A8 CDRs wherein the amino acid sequence of the light chain is $AA_{1}$–$AA_{219}$ of SEQ ID NO:56 and the amino acid sequence of the heavy chain is $AA_{1}$–$AA_{448}$ of SEQ ID NO:45.

This invention provides DNA sequences encoding a pre-5A8 humanized light chain (SEQ ID NO:55) and a pre-5A8 humanized heavy chain (SEQ ID NO:44), portions of the foregoing DNA sequences that encode antibody homologs according to this invention, and DNA sequences degenerate to the foregoing DNA sequences. Also provided are recombinant DNA molecules comprising one or more of the foregoing DNA sequences and one or more expression control sequences operatively linked thereto. Preferred recombinant DNA molecules include pMDR1007 (pre-5A8 humanized light chain) and pMDR1002 (pre-5A8 humanized heavy chain), deposited with the American Type Culture Collection, Rockville, Md., under accession numbers ATCC 68846 and ATCC 68847, respectively.

D. Antibody Homologs According To This Invention That Are Not Intact Antibodies

The present invention also provides antibody homologs that are not intact antibodies. Such homologs may be derived from any of the antibody homologs described above. For example, antigen-binding fragments, as well as full-length monomeric, dimeric or trimeric polypeptides derived from the above-described antibodies are themselves antibody homologs according to the present invention. Useful antibody homologs of this type include Fab fragments, Fab' fragments, F(ab')$_2$ fragments, F(v) fragments, heavy chain monomers or dimers, light chain monomers or dimers, dimers consisting of one heavy and one light chain, and the like. We believe that the foregoing fragments, other than Fab fragments of 5A8, generally are useful antibody homologs according to the present invention.

Antibody fragments may be produced by chemical methods, e.g., by cleaving an intact antibody with a protease, such as pepsin or papain, and optionally treating the cleaved product with a reducing agent. Alternatively, useful fragments may be produced by using host cells transformed with truncated heavy and/or light chain genes. Heavy and light chain monomers may be produced by treating an intact antibody with a reducing agent, such as dithiothreitol, followed by purification to separate the chains. Heavy and light chain monomers may also be produced by host cells transformed with DNA encoding either the desired heavy chain or light chain, but not both. See, e.g., E. S. Ward et al., "Binding Activities Of A Repertoire of Single Immunoglobulin Variable Domains Secreted From *Escherichia coli*", *Nature*, 341, pp. 544–46 (1989); L. Sastry et al., "Cloning Of The Immunological Repertoire in *Escherichia coli* For Generation Of Monoclonal Catalytic Antibodies: Construction Of A Heavy Chain Variable Region-Specific cDNA Library", *Proc. Natl. Acad. Sci. USA*, 86, pp. 5728–32 (1989).

Derivatized Antibody Homologs According To This Invention

In one embodiment, this invention provides derivatized antibody homologs in which any of the antibody homologs of this invention are functionally linked (by chemical coupling, genetic fusion or otherwise) to one or more members independently selected from the group consisting of antibody homologs of this invention, 5A8-mimetic agents of this invention, detectable agents, cytotoxic agents and pharmaceutical agents. One type of derivatized antibody homolog is produced by crosslinking two or more antibody homologs (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents include fluorescent compounds. Exemplary fluorescent detectable agents include fluorescein, fluorescein isothiocyanate, rhodamine, 5-dimethylamine-1-napthalenesulfonyl chloride, phycoerythrin and the like.

The antibody homologs of this invention may also be derivatized with detectable enzymes, such as alkaline phosphatase, horseradish peroxidase, glucose oxidase and the like. When the antibody homolog is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. The antibody homolog may also be derivatized with biotin, and detected through indirect measurement of avidin binding.

The present invention also provides antibody homologs linked to one or more pharmaceutical agents. Useful pharmaceutical agents include biologically active peptides, polypeptides and proteins, such as antibody homologs specific for a human polypeptide other than CD4. Other useful pharmaceutical agents include non-proteinaceous pharmaceutical agents such as HIV reverse transcriptase inhibitors (e.g., 3'-azido-2',3'-dideoxythymidine ("AZT") and 2',3'-dideoxyinosine ("DDI") and other antiviral compounds, or immunosuppressive agents (e.g., cyclosporin or FK506).

Cells That Produce Antibody Homologs According To The Present Invention

The present invention also provides cells and cell cultures that produce the antibody homologs of this invention. Such cells include hybridoma cells that produce monoclonal antibodies which are antibody homologs of this invention, as well as transformed host cells that produce recombinant antibody homologs of this invention.

Preferred cells according to this invention include those that produce the monoclonal antibodies referred to herein as "5A8", "1F8" and "5F2". The most preferred cell line produces monoclonal antibody 5A8. The hybridoma cell lines producing 5A8, 1F8 and 5F2 were deposited in the In Vitro International, Inc. culture collection in Linthicum, Md., under accession numbers IVI-10257, IVI-10258 and IVI-10259, respectively and transferred to the American Type Culture Collection, Rockville, Md., under accession numbers HB 10881, HB 10882 and HB 10883, respectively.

Other preferred cells are host cells producing the 5A8 chimeric and humanized recombinant antibodies described supra. Eukaryotic host cells transformed with pMDR1007 (pre-5A8 humanized light chain) and pMDR1002 (pre-5A8 humanized heavy chain) are most preferred for producing 5A8 humanized antibodies.

Moreover, the present invention provides a method of producing the antibody homologs of the present invention by culturing the cells of this invention, which produce the antibody homologs. Methods of culturing such cells and isolating the antibody homologs they produce are well known. These methods include tissue culture techniques, as well as the generation of ascites.

Also provided is a method for producing cells of this invention which are hybridoma cells, comprising the step of immunizing a nonhuman mammal with $CD4^+$ cells produced by transforming $CD4^-$ mammalian tissue culture cells with DNA encoding full-length human CD4, which cells express the CD4 on their surface. Preferred cells to be used as an immunogen for this process are the r-CD4-CHO cells described above.

5A8-Mimetic Agents

The present invention provides 5A8-mimetic agents, which are compounds that cause at least a 30% reduction in the binding of monoclonal antibody 5A8 either to human rsCD4 or to human CD4 displayed on the surface of a $CD4^+$ cell. 5A8-mimetic agents may be peptides, semi-peptidic compounds or non-peptidic compounds. Preferred 5A8-mimetic agents inhibit HIV-induced syncytia formation between $CD4^+$ cells, inhibit infection of $CD4^+$ cells by HIV, or both. The most preferred 5A8-mimetic agents display the properties of one or more antibody homologs of this invention. 5A8-mimetic agents of this invention may be produced by synthesizing a plurality of peptides (e.g., 5–20 amino acids in length), semi-peptidic compounds or non-peptidic, organic compounds, and then screening those compounds for their ability (1) to cross block with 5A8 for binding to human CD4, (2) to inhibit HIV-induced syncytia formation between $CD4^+$ cells, and (3) to inhibit infection of $CD4^+$ cells by HIV. See generally U.S. Pat. No. 4,833,092, J. K. Scott and G. P. Smith, "Searching For Peptide Ligands With An Epitope Library", *Science*, 249, pp. 386–90 (1990), and J. J. Devlin et al., "Random Peptide Libraries: A Source Of Specific Protein Binding Molecules", *Science*, 249, pp. 404–07 (1990), which are herein incorporated by reference.

Pharmaceutical Compositions And Methods According To This Invention

The antibody homologs and the 5A8-mimetic agents of this invention are useful in prophylactic and therapeutic compositions for preventing and treating diseases caused by infective agents whose primary targets are $CD4^+$ lymphocytes. Such diseases include AIDS, ARC and HIV infection.

Preferred pharmaceutical compositions of this invention for administration to humans include, as antibody homologs, one or more of the mouse monoclonal antibodies 5A8, 1F8 or 5F2, 5A8 mouse/human chimeric recombinant antibodies, 5A8 humanized recombinant antibodies or antigen-binding portions of those antibodies. Pharmaceutical compositions comprising 5A8 mouse/human chimeric recombinant antibodies or 5A8 humanized recombinant antibodies are most preferred.

The pharmaceutical compositions of this invention may further comprise other therapeutics for the prophylaxis or treatment of AIDS, ARC and HIV infection. For example, the antibody homologs of this invention may be used in combination with anti-retroviral agents that block reverse transcriptase, such as AZT, DDI, HPA-23, phosphonoformate, suramin, ribavirin and dideoxycytidine, or with agents that inhibit the HIV protease. Additionally, the pharmaceutical compositions of this invention may further comprise anti-viral agents such as interferons, including alpha interferon, beta interferon and gamma interferon, or glucosidase inhibitors such as castanospermine, or immunosuppressive agents such as adrenal corticosteroids, azathrioprine, cyclosporin or FK506. Moreover, the antibody homologs of this invention may advantageously be administered in combination with agents that significantly block binding of HIV gp120 to CD4. Such agents include, for example, anti-CD4 antibodies that are V1-specific (e.g., Leu3A), CD4 V1 polypeptides and antibodies (anti-idiotypic or otherwise) specific for HIV gp120.

Furthermore, one or more antibody homologs or 5A8-mimetic agents may be used in combination with two or more of the foregoing therapeutic agents. Such combination therapies may advantageously utilize lower dosages of the administered therapeutic agents, thus avoiding possible toxicities or complications associated with the various mono-therapies.

The pharmaceutical compositions of this invention comprise an immunotherapeutically effective amount of one or more antibody homologs or 5A8-mimetic agents according to this invention, or derivatized form(s) thereof and, preferably, a pharmaceutically acceptable carrier. By "immunotherapeutically effective amount" is meant an amount capable of lessening the spread, severity or immunocompromising effects of AIDS, ARC or HIV infection, or of other diseases caused by infective agents whose primary targets are $CD4^+$ lymphocytes. By "pharmaceutically acceptable carrier" is meant a carrier that does not cause an allergic reaction or other untoward effect in patients to whom it is administered.

Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody homolog or 5A8-mimetic agent.

The compositions of this invention may be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and therapeutic application. The preferred compositions are in the form of injectable or infusible solutions.

The preferred pharmaceutical compositions of this invention are similar to those used for passive immunization of humans with other antibodies. The preferred mode of administration is parenteral.

It will be apparent to those of skill in the art that the immunotherapeutically effective amount of antibody homolog or 5A8-mimetic agent of this invention will depend, inter alia, upon the administration schedule, the unit dose of antibody homolog or 5A8-mimetic agent administered, whether the antibody homolog or 5A8-mimetic agent is administered in combination with other therapeutic agents, the immune status and health of the patient, and the therapeutic activity of the particular antibody homolog or 5A8-mimetic agent administered.

In monotherapy for treatment or prophylaxis of HIV infection, ARC or AIDS, immunotherapeutically effective amounts per unit dose of an antibody homolog which is an intact antibody range from about 0.1 to 10 mg/kg patient weight, preferably 2 mg/kg patient weight. Unit doses should be administered from twice each day to once every two weeks until an antiviral effect is observed, preferably once every two weeks. The antiviral effect may be measured by a variety of methods, including viral load, lymphocyte counts and clinical signs and symptoms. It will be recognized, however, that lower or higher dosages and other administration schedules may be employed.

Treatment regimens for antibody homologs that are not intact antibodies and for 5A8-mimetic agents may differ, depending on their size and pharmaceutical properties.

In order that this invention may be better understood, the following examples are set forth. These examples are for purposes of illustration only, and are not to be construed as limiting the scope of the invention in any manner.

EXAMPLES

Production And Initial Screening Of Antibody Homologs Of This Invention

The immunogen used to generate monoclonal antibodies 1F8, 5A8 and 5F2 was CHO cells transformed with DNA encoding full-length human CD4 expressed on the cell surface ("r-CD4-CHO cells"). The CD4 sequence used to transform the CHO cells is set forth in Maddon et al., *Cell*, supra. These cells are described in R. A. Fisher et al., "HIV Infection Is Blocked In Vitro By Recombinant Soluble CD4", *Nature*, 331, pp. 76–78 (1988), and were deposited with the In Vitro International, Inc. culture collection, Linthicum, Md., under accession number IVI-10260 and transferred to American Type Culture Collection, Rockville, Md., under accession number CRL 10884.

The r-CD4-CHO cells were maintained at 37° C., under 5% $CO_2$, in a MEM media (Gibco, Grand Island, N.Y.) supplemented with 10% dialyzed fetal calf serum ("FCS") (North American Biologics, Miami, Fla., cat. no. 33189) and 30 nM methotrexate. Cells were prepared for injection by substituting the above culture medium with phosphate buffered ($Ca^+$- and $Mg^+$-free) saline ("PBS") supplemented with 5 mM EDTA, and harvesting the cells in that buffer. The harvested cells were pelleted by centrifugation at $500 \times g_{av}$ for about 5 minutes, washed once by resuspending the pellet in PBS and centrifuging as before, counted, and adjusted to the appropriate volume for injection by resuspending the cell pellet in PBS.

Two female BALB/c J mice, about 4–6 weeks old (Jackson Labs, Bar Harbour, Me.), were immunized with r-CD4-CHO cells as follows. The first mouse was primed intraperitoneally (i.p.) on day 0 with a 1:1 emulsion of r-CD4-CHO cells in PBS with complete Freunds adjuvant ("CFA") (Colorado Serum Co., Denver, Colo., cat. no. C51450), boosted i.p. on day 20 with r-CD4-CHO cells in PBS without adjuvant, and finally boosted intravenously on day 44 with r-CD4-CHO cells in PBS, without adjuvant. The other mouse was primed i.p. on day 0, boosted i.p. on day 15, and finally boosted intravenously on day 39 (all injections with r-CD4-CHO cells in PBS, without adjuvant). For both mice, each injection contained approximately $3 \times 10^6$ to $2 \times 10^7$ r-CD4-CHO cells in a volume of approximately 250 $\mu$l.

Three days after the last injection, both mice were sacrificed and each spleen was removed and placed in approximately 5 ml of serum-free DMEM (Gibco, cat. no. 430-2100) in a petri dish. The splenic capsules were cut and the spleen cells were teased out into the medium. The spleen cell suspensions were transferred to one 15 ml conical bottom tube and allowed to settle for about 5 minutes. The supernatant was removed to a fresh 15 ml conical bottom tube and placed in an incubator (37° C., 5% $CO_2$) until the fusion. The spleen cells from both mice were pooled.

A 5-ml single cell suspension of control spleen feeder cells was prepared from an unimmunized mouse essentially as described above for the immunized spleen cells, and placed in an incubator (37° C., 5% $CO_2$) until needed.

The fusion partner for the immunized spleen cells was a hypoxanthine/aminopterin/thymidine ("HAT")-sensitive, non-secreting mouse myeloma cell line—P3X63-AG8.653 (ATCC, Rockville, Md., cat. no. CRL 1580). Prior to the fusions, the P3X63-AG8.653 cells were maintained in DMEM/10% FCS (37° C., 5% $CO_2$), ensuring that they were in a logarithmic growing phase on the day of the fusions.

The fusion protocol used was a hybrid of the protocols set forth in Lerner, *Yale J. Biol. Med.*, supra and Gefter et al., *Somatic Cell Genet.*, supra. Specifically, immediately before the fusions, the pooled spleen cells prepared as described above were washed three times with PBS, resuspended in approximately 10 ml of PBS and counted. Also immediately before fusion, the logarithmic phase P3X63-AG8.653 cells were washed three times with PBS and counted. The myeloma cells were resuspended to $1 \times 10^7$ cells/ml in PBS. For each fusion, $1.5 \times 10^8$ spleen cells were mixed with $3 \times 10^7$ myeloma cells in a 50 ml conical bottom polypropylene tube, and the cells were washed once with PBS. The ratio of spleen cells to myeloma cells was 5:1. The tubes were centrifuged at $500 \times g_{av}$ for 5 minutes to pellet the cells. After aspiration of the supernatants, the pellets were gently resuspended by tapping the bottom of the tubes. The tubes were then placed in a beaker of 37° C. water. All subsequent fusion steps were carried out in this beaker.

Next, 0.8 ml of 37° C. fusion medium (50 w/v % polyethylene glycol 3350 ("Baker" grade from J. T. Baker Co., Phillipsburg, N.J.) in serum-free DMEM was slowly added to each cell pellet over the course of about 1 minute, while gently rocking the tube. One ml serum-free DMEM was added dropwise to each pellet over the course of another minute, and then 20 ml serum-free DMEM was added to each pellet over the next 5 minutes. Both tubes were centrifuged at 600×g for 10 minutes at room temperature, and the supernatants were aspirated. Fifty ml of "HAT selection medium" containing 400 $\mu$l of the 5-ml suspension of control spleen feeder cells (prepared as described above) were added stepwise to each pellet, with occasional mixing. "HAT selection medium" was prepared by diluting a 50× HAT stock (Sigma Chemical Co., St. Louis, Mo., cat. no. H-0262) 50-fold in DMEM/10% FCS (final concentrations: 10 $\mu$M hypoxanthine, 0.4 $\mu$M aminopterin, 16 $\mu$M thymidine).

Each 50-ml cell suspension was plated into 5 96-well flat-bottom microtiter plates, with ~100 μl/well. The plates were kept in an incubator at 37° C., 5% $CO_2$. On day 2 post-fusion, the cells were fed by addition of 100 μl HAT selection medium per well. On day 10 post-fusion, the medium was aspirated and 200 μl HAT selection medium was added to each well. Supernatants were withdrawn for primary screening on days 12, 14, 16 and 19 post-fusion, from wells containing clones. The fusion efficiency was 34% (327 out of 960 possible wells developed clones that were screened).

The primary screen used was a radioimmunoassay (RIA) designed to detect antibodies that bind to human rsCD4.

To perform the RIA, affinity-purified goat anti-mouse IgG ($F_c$ fragment-specific) (Cappell, Cochranville, Pa., cat. no. 22950) in PBS was added to 96-well PVC microtiter plates (50 μl/well) and incubated overnight at 4° C. The goat anti-mouse IgG was removed from the plates and the wells were blocked with 100 μl/well of 5% FCS/PBS for 1 hour at room temperature. After removing the blocking solution, neat hybridoma culture supernatant was added to the wells (50 μl/well) and incubated 1 hour at room temperature. The plates were washed 3 times with PBS/0.05% Tween-20. Next, 50 μl $^{125}$I-rsCD4 (~20,000 cpm) in PBS/5% FCS (prepared as described below) was added to each well, and incubated 1 hour at room temperature. Finally, the wells were washed 3 times with PBS/0.05% Tween-20. After flicking out all the wash buffer, the wells were separated by cutting the plates and analyzed in a gamma counter. Wells to which 5% FCS/PBS had been added instead of culture supernatant served as background wells.

The $^{125}$I-rsCD4 used in the primary screening assay consisted of purified, $^{125}$I-labelled human CD4 $AA_3$–$AA_{377}$ of the CD4 sequence set forth in Maddon et al., *Cell,* supra (i.e., human CD4 $AA_1$–$AA_{375}$ according to the corrected numbering system of Littman et al., *Cell,* supra). The rsCD4 was produced by transformed CHO cells substantially as described in Fisher et al., *Nature,* supra. The rsCD4 produced by those cells may be purified as described in Fisher et al., *Nature,* supra.

The purified rsCD4 was labelled with $^{125}$I according to the Bolton-Hunter method, substantially as described by the supplier of the Bolton-Hunter reagent (New England Nuclear, Boston, Mass.). The quality of the $^{125}$I-rsCD4 was routinely monitored by confirming that the labelling procedure did not destroy the epitopes recognized by the commercially available CD4 V1-specific monoclonal antibodies Leu3A (Becton Dickinson, Mountain View, Calif., cat. no. 7326) and OKT4A (Ortho Diagnostic Systems, Raritan, N.J., cat. no. 7124) and the CD4 V3V4-specific monoclonal antibody OKT4 (Ortho Diagnostic Systems, cat. no. 7024).

Clones were considered to be positive on primary screening if they were approximately 10-fold over background in the RIA. By this criterion, approximately 6% of the clones (21) were positive. The 21 positive clones were pulled and expansion was attempted; 13 clones survived expansion and were stored frozen. Many of these 13 clones were successfully subcloned, including 1F8, 5A8 and 5F2. Expansion, subcloning and freezing of the cells was conducted substantially as described in Lerner, *Yale J. Biol Med.,* supra.

The 13 positive clones isolated after primary screening were subjected to the battery of tests described below. Based on those assays, we identified three hybridoma cell lines that produced antibody homologs according to the present invention—1F8, 5A8 and 5F2. The results of the screening assays for clones 1F8, 5A8 and 5F2 are discussed below. The data for the other 10 antibodies are not shown.

The first secondary screen we conducted was designed to determine whether the antibodies recognized native CD4 epitopes. This was accomplished by FACS analysis of cell surface CD4 displayed on $CD4^+$ Jurkat cells and r-CD4-CHO cells stained with the monoclonal antibodies, visualizing binding with fluorescently labelled goat anti-mouse second antibody, substantially as described below. All 13 antibodies recognized cell surface CD4. Next, to localize the CD4 epitopes bound by our antibodies, we conducted competition assays as described below with a CD4 V1 polypeptide and a CD4 V1V2 polypeptide, with commercially available CD4 V1-specific and CD4 V3V4-specific antibodies, and with HIV gp120. Many of the antibodies were then also assessed for their ability to inhibit HIV-induced syncytia formation between $CD4^+$ cells and infection of $CD4^+$ cells by HIV, as well as for their immunosuppressive activity in an in vitro tetanus toxoid-specific proliferation assay.

Based on the competition assays, we determined that of the 13 positive clones, 3 secreted CD4 V1-specific antibodies, 5 secreted antibodies that were CD4 V3V4-specific, and 5 secreted antibodies that were CD4 V1V2-specific. Of the CD4 V1V2-specific antibodies, only three— 1F2, 5A8 and 5F2—did not significantly block HIV gp120 binding to CD4.

In a single fusion performed after immunization of a mouse with human rsCD4, none of the hybridomas was found to produce an antibody that was an antibody homolog of this invention, although other anti-CD4 monoclonal antibodies were produced. We believe that anti-CD4 antibody homologs according to this invention may be generated by immunization with rsCD4; however, using r-CD4-CHO cells as the immunogen increases the likelihood of obtaining such antibodies.

Specificity For CD4 VI And CD4 V1V2 Polypeptides

In order to characterize the CD4 epitopes recognized by the antibody homologs of this invention, we determined whether several antibody homologs recognized an epitope in the V1V2 region of human CD4, or an epitope defined solely by the CD4 V1 region. Specifically, we studied the ability of polypeptides consisting of $AA_1$–AA 113 and/or $AA_1$–$AA_{111}$ of human CD4 ("CD4-V1") and $AA_1$–$AA_{180}$ of human CD4 ("CD4-V1V2") to inhibit binding of human rsCD4 to three anti-CD4 antibody homologs of this invention (monoclonal antibodies 1F8, 5A8, and 5F2), two CD4 V1-specific monoclonal antibodies (Leu3A and OKT4A) and a CD4 V3V4-specific monoclonal antibody (OKT4).

Briefly, an RIA was performed in which each microtiter plate well was coated with an anti-mouse Ig, blocked, and then incubated with one of the hybridoma culture supernatants being tested. Next, a mixture of CD4-V1 or CD4-V1V2 and $^{125}$I-rsCD4 was added. After incubation, the wells were washed and the bound $^{125}$I-rsCD4 was detected in a gamma counter.

Specifically, microtiter plates (96-well) were coated overnight at 4° C. with 50 μl/well of affinity-purified goat anti-mouse IgG (Fc fragment-specific) (Cappell). Wells were washed 3 times with PBS/0.05% Tween-20, and then blocked by incubating 1 hour with 100 μl/well of 5% FCS/PBS. After removing the blocking buffer, the wells were incubated 1 hour at room temperature with 50 μl/well neat hybridoma culture supernatant (5–20 μg/ml Ig). The control wells were incubated with 50 μl/well OKT4 (10 μg/ml in PBS/5% FCS), OKT4A (500 ng/ml in PBS/5% FCS) or Leu3A (500 ng/ml in PBS/5% FCS). The plates were washed 3 times with PBS/0.05% Tween-20. CD4-V1 and CD4-V1V2 (final concentrations 5 μg/ml) were separately pre-incubated with approximately 20,000 cpm $^{125}$I-rsCD4 (prepared as described above), for approximately 35–45 minutes at room temperature. Those pre-incubated mixtures were then incubated in the wells for 1–2 hours at room temperature. Following the incubation, the wells were washed 3 times with PBS/0.05% Tween-20 and then counted for radioactivity.

The CD4-V1used in this experiment consisted of $AA_3$–$AA_{115}$ and/or $AA_3$–$AA_{113}$ of the CD4 sequence set forth in FIG. 16 of PCT patent application PCT/US88/02940, which correspond respectively to CD4 $AA_1$–$AA_{113}$ and $AA_1$–$AA_{111}$ according to the corrected numbering system of Littman et al., Cell, supra. These CD4 V1 polypeptides were produced and purified as described in B. H. Chao et al., "A 113-Amino Acid Fragment Of CD4 produced In Escherichia coli Blocks Human Immunodeficiency Virus-Induced Cell Fusion", J. Biol. Chem., 264, pp. 5812–17 (1989).

The CD4-V1V2 used in this experiment consisted of $AA_3$–$AA_{182}$ of the CD4 sequence set forth in FIG. 16 of PCT patent application PCT/US88/02940, which corresponds to CD4 $AA_1$–$AA_{180}$ according to the corrected numbering system of Littman et al., Cell, supra.

The CD4 V1V2 polypeptide was bacterially produced using standard molecular biology techniques, in a manner analogous to the protocol used for production of the CD4 V1 polypeptide described in Chao et al., J. Biol. Chem., supra. A plasmid carrying DNA encoding the CD4 V1V2 polypeptide was transfected into E. coli, strain A89 [S. A. Goff et al., "Heat Shock Regulatory Gene htDR Influences Rates of Protein Degradation And Expression Of The lon Gene In Escherichia coli", Proc. Natl. Acad. Sci. USA, 81, pp. 6647–51 (1984)]. The cells were fermented under standard conditions in a 10-liter fermenter, harvested using a Pelikon concentration system followed by centrifugation at 3000 rpm in a Beckman J-6M centrifuge. The cell pellet was stored frozen at −20° C. until use.

To purify the CD4-V1V2, the cells were thawed and suspended in 8 ml buffer (20 mM Tris-HCl, pH 7.7/1 mM $Na_2$EDTA) per gram wet cell weight. The cells were broken by 3 passes through a french press. The insoluble material containing the CD4-V1V2 was pelleted by centrifugation. The pellets were washed 3 times with 1M urea/15 mM sodium acetate, pH 5.5 (15–20 ml per gram wet cell weight), followed by 2 washes with 20 mM Tris-HCl, pH 7.7/1 mM $Na_2$EDTA. The resulting washed pellet was extracted overnight at room temperature with 25 ml per gram of wet cell weight using 6M guanidine-HCl/10 mM DTT/20 mM Tris-HCl, pH 7.7. The extract was clarified by centrifuging at 48,000×$g_{av}$ for 45 minutes at room temperature.

To renature the CD4-V1V2, the clarified extract was diluted 1:60 v/v into cold (4° C.) 20 mM Tris-HCl, pH 7.7, and bovine serum albumin ("BSA") was added to a final concentration of 0.5 mg/ml. All subsequent steps were performed at 4° C. The pH was lowered to 7.0 with 6N HCl, and the suspension was clarified by passage through a 5 micron hydrophilic Millidisk filter (Millipore, Bedford, Mass., cat. no. MCSC 40S 01) followed by passage through a Durapore 0.2 micron filter (Millipore, cat. no. CVGL 01T P3). The clarified preparation was loaded onto an S-Sepharose Fast Flow column (Pharmacia LKB Biotechnology, Inc., Piscataway, N.J.), pre-equilibrated with 20 mM Tris-HCl, pH 7.0, at a ratio of 1 volume S-Sepharose Fast Flow gel per 100 volumes load. The column was washed with 20 mM Tris-HCL, pH 7.0, and the bound proteins were eluted with 20 mM Tris-HCl, pH 7.7/300 mM NaCl.

The eluate pool containing the CD4-V1V2 was diluted with an equal volume of 20 mM Tris-HCl, pH 7.7, and then loaded onto an anti-CD4 monoclonal antibody affinity column (described below), pre-equilibrated with 20 mM Tris-HCl, pH 7.7/150 mM NaCl. The column was washed with 20 mM Tris-HCl, pH 7.7/150 mM NaCl followed by 20 mM Tris-HCl, pH 7.7/1 M NaCl. The bound proteins were eluted with 50 mM glycine/250 mM NaCl, pH 3.0. The eluted material was dialyzed into 20 mM HEPES, pH 6.8, and concentrated on a PM 10 membrane in an Amicon ultrafiltration cell. The purified, concentrated CD4-V1V2 (approximately 0.5–3.0 mg/ml) was stored at −70° C. until use.

The anti-CD4 monoclonal antibody affinity column was prepared using one of the CD4 V1-specific monoclonal antibodies produced from the fusions described above. The monoclonal antibody was purified from ascites by ammonium sulfate fractionation and anion exchange chromatography, concentrated by ultrafiltration, dialyzed into 0.1M sodium borate (pH 8.0)/0.5M sodium chloride, .and concentrated again by ultrafiltration to a concentration of approximately 5 mg/ml. The purified anti-CD4 monoclonal antibody (10 ml containing approximately 50 mg protein) was coupled to 4 g of CNBr-Sepharose according to the manufacturer's directions (Sigma Chemical Co., cat. no. C9142), yielding 12 ml of derivatized resin.

The results of these experiments are summarized in Tables I and II.

TABLE I

CD4-V1 Inhibition of rsCD4 Binding: Simultaneous Competition

| Anti-CD4 Monoclonal Antibody | CD4-V1 % Inhibition of rsCD4 Binding | Number of Replicates |
|---|---|---|
| 1F8 | −4.9* | 1 |
| 5A8 | 4.3 ± 8.8* | 3 |
| 5F2 | −2.3* | 1 |
| OKT4 | −5.5 ± 6.0* | 4 |
| OKT4A | 87.3 ± 9.1 | 4 |
| Leu3A | 88.2 ± 8.7 | 3 |

*Because of the standard deviations encountered in assays of this type, we consider this figure to indicate that CD4-V1 caused no real inhibition of rsCD4 binding to the anti-CD4 monoclonal antibody indicated.

TABLE II

CD4-V1V2 Inhibition of rsCD4 Binding: Simultaneous Competition

| Anti-CD4 Monoclonal Antibody | CD4-V1V2 % Inhibition of rsCD4 Binding | Number of Replicates |
|---|---|---|
| 1F8 | 94.0 ± 1.8 | 3 |
| 5A8 | 96.4 ± 0.5 | 3 |
| 5F2 | 93.5 ± 0.9 | 3 |
| OKT4 | 14.4 ± 15.1* | 2 |
| OKT4A | 95.5 ± 1.7 | 2 |
| Leu3A | 94.0 ± 3.4 | 2 |

*Because of the standard deviations encountered in assays of this type, we consider this figure to indicate that CD4-V1V2 caused no real inhibition of rsCD4 binding to the anti-CD4 monoclonal antibody indicated.

The data displayed in Tables I and II demonstrate that monoclonal antibodies 1F8, 5A8 and 5F2 do not bind to a polypeptide consisting of human CD4 V1, and do bind to a polypeptide consisting of human CD4 V1V2.

Cross Blocking With 5A8 and With Antibodies That Are CD4 V1-Specific and CD4 V3V4-Specific To characterize further the CD4 epitopes recognized by the antibody homologs of this invention, we performed cross blocking experiments for rsCD4 with an antibody homolog, 5A8, and two CD4 V1-specific antibodies (OKT4A and Leu3A), as well as with a CD4 V3V4-specific antibody (OKT4). We also performed similar cross blocking experiments between 5A8 and other antibody homologs of this invention. In addition, we performed a cross blocking experiment with Leu3A and 5A8 for native CD4 displayed on the surface of human peripheral blood lymphocytes. The results of these cross blocking experiments are displayed in Tables III and IV, and in FIG. 1.

For the rsCD4 cross blocking experiment presented in Table III, an RIA was performed substantially as described above for the CD4-V1 and CD4-V1V2 crossblocking experiments. Specifically, each microtiter plate well was coated with anti-mouse Ig, blocked, and then incubated with 5A8 culture supernatant (5–20 μg/ml), OKT4A (500 ng/ml), OKT4 (10 μg/ml) or Leu3A (500 ng/ml). The wells were then washed, and blocked with the 100 μl/well mouse Ig (50 μg/ml) in PBS for 30 minutes to 1 hour at room temperature. Competitor antibody (i.e., OKT4A, OKT4 or Leu3A at twice the above concentrations) was pre-incubated with $^{125}$I-rsCD4, and each mixture was added to the wells at 50 μl/well. After incubating 1 hour at room temperature, the wells were washed and the bound 125 I-rsCD4 was quantified in a gamma counter.

Table III lists the percent inhibition of binding of $^{125}$I-rsCD4 to the immobilized anti-CD4 antibodies 5A8, OKT4, OKT4A and Leu3A by the soluble anti-CD4 antibodies Leu3A, OKT4A and OKT4.

TABLE III

Leu 3A, OKT4A and OKT4 Cross Blocking:
Anti-CD4 Monoclonal Antibodies Preincubated In Solution With rsCD4

| Immobilized Anti-CD4 Monoclonal Antibody | % Inhibition rsCD4 Binding: | | | Number Of Replicates |
|---|---|---|---|---|
| | By Leu 3A | By OKT4A | By OKT4 | |
| 5A8 | 16.1 ± 5.7 | 5.3 ± 8.3* | −15.6 ± 25.4* | 3 |
| OKT4 | 8.4 ± 3.3 | 3.6 ± 7.7* | 91.3 ± 2.1 | 3 |
| OKT4A | 62.0 ± 3.1 | 68.5 ± 2.6 | −26.8 ± 18.3* | 3 |
| Leu3A | 85.8 ± 0.5 | 73.9 ± 1.9 | −10.3 ± 8.9* | 3 |

*Because of the standard deviations encountered in assays of this type, we consider this figure to indicate that the anti-CD4 monoclonal antibody indicated at the top of the column caused no real inhibition of rsCD4 binding to the indicated anti-CD4 monoclonal antibody for that row.

The data displayed in Table III demonstrate that Leu3A, OKT4A and OKT4 do not significantly block binding of rsCD4 to 5A8. These results imply that 5A8 recognizes different CD4 epitope(s) than those recognized by Leu3A, OKT4A and OKT4.

For the rsCD4 cross blocking experiment presented in Table IV, an RIA was performed substantially as described above for the experiment presented in Table III, except that only 5A8 was immobilized, and the soluble competitor antibodies were 1F8 (5–20 μg/ml), 5A8 (5–20 μg/ml), 5F2 (−5 μg/ml), OKT4 (10 μg/ml) and Leu3A (500 ng/ml). In addition, the $^{125}$I-rsCD4 used in this experiment consisted of purified, $^{125}$I-labelled human CD4 AA$_3$–AA$_{377}$ of the CD4 sequence set forth in FIG. 16 of PCT patent application PCT/US88/02940 (rather than the sequence set forth in Maddon et al., Cell, supra, which corresponds to CD4 AA 1–AA 375 according to the corrected numbering system of Littman et al., Cell, supra.

Table IV lists the percent inhibition of binding of $^{125}$I-rsCD4 to immobilized 5A8 by the soluble anti-CD4 antibodies 1F8, 5F2, 5A8, OKT4 and Leu3A.

TABLE IV

5A8 Cross Blocking:
Anti-CD4 Monoclonal Antibodies
Preincubated In Solution With rsCD4

| Soluble Anti-CD4 Monoclonal Antibody | % Inhibition rsCD4 Binding |
|---|---|
| 1FB | 97 |
| 5A8 | 98 |
| 5F2 | 89 |
| OKT4 | 4 |
| Leu3A | 0 |

The data displayed in Table IV demonstrate that 1F8 and 5F2 block binding of rsCD4 to 5A8, implying that 5A8, 1F8 and 5F2 recognize the same, overlapping, or proximate CD4 epitope(s).

FIG. 1 displays the results of the cell surface CD4 cross blocking experiment. Human peripheral blood lymphocytes ("PBLs") were incubated with buffer (FIG. 1A), Leu3A (FIG. 1B), OKT4A (FIG. 1C), OKT4 (FIG. 1D) or 5A8 (FIG. 1E). The cells then were washed and incubated with Leu3A labelled with fluorescein isothiocyanate ("Leu3A-FITC"). After washing again, the cells were analyzed using a FACStar fluorescence activated cell sorter. The results of the this FACS analysis are depicted in FIG. 1. The data demonstrate that 5A8 does not significantly block binding of the V1-specific antibody Leu3A to cell surface CD4. The protocol for this experiment follows.

Specifically, human PBLs were isolated by diluting 10 ml blood two-fold with unsupplemented RPMI-1640 media and layering the mixture over 10 ml of Lymphocyte Separation Media (Organon Teknika, Durham, N.C., cat. no. 36427) in a 50-ml tube at room temperature. The tube was centrifuged at room temperature for 30 minutes at 400×g$_{av}$. PBLs were collected from the interface, washed two times with unsupplemented RPMI-1640 media and counted. For each sample, 3×10$^5$ PBLs were suspended in 50 μl of staining buffer (PBS/1% BSA/0.02% sodium azide) per tube and washed one time with staining buffer. The staining buffer was aspirated from the pelleted cells, and antibody reagent was added to each pellet. For 5A8, the antibody reagent was 50 μl conditioned hybridoma cell culture supernatant containing approximately 5–20 μg/ml 5A8. The antibody reagents for the control antibodies were 2.5 μg/ml solutions in staining buffer: 60 μl/tube Leu3A; 30 μl/tube OKT4A; 30 μl/tube OKT4. As an additional control, one cell sample received 50 μl of staining buffer without antibody.

Samples were incubated for 30 minutes on ice, then washed three times in 1 ml volumes of staining buffer. Next, 66 μl of FITC-conjugated Leu3A (Becton Dickinson, cat. no. 7323) was added at a 1:10 dilution in staining buffer; then the samples were incubated for 20 minutes on ice, washed two times and analyzed on a FACStar fluorescence activated cell sorter (Becton Dickinson Immunocytometry Systems, Mountain View, Calif.).

HIV gp120 Cross Blocking

We used two approaches to determine whether antibody homologs of this invention block binding of HIV gp120 to human CD4—an RIA using human rsCD4 and FACS analysis with human CD4$^+$ tissue culture cells.

The soluble, recombinant, HIV gp120 ("r-gp120")-used in these assays was produced using a baculovirus vector/ insect cell culture system. The vector used to transfer the truncated HIV-1 gp120 gene into *Autographa californica* nuclear polyhedrosis virus (baculovirus) was a derivative of vector pAc373 [G. E. Smith et al., "Modification And Secretion Of Human Interleukin 2 Produced In Insect Cells By A Baculovirus Expression Vector", *Proc. Natl. Acad. Sci. USA,* 82, pp. 8404–08 (1985)].

DNA sequences encoding the signal peptide and propeptide of human tissue plasminogen activator and a C-terminal methionine were ligated in-frame to HIV-1 DNA sequences encoding $AA_{13}$–$AA_{471}$ of gp160 (see SEQ ID NO:1 and SEQ ID NO:2), followed by DNA encoding leucine and serine (SEQ ID NO:3), in the pAc373 vector. The resulting vector and wild type baculovirus were cotransfected into Spodoptera frugiperda (sf9) cells, and the recombinant baculovirus expressing the two HIV r-gp120 polypeptides was isolated according to the methods described in M. D. Summers and G. E. Smith, in *A Manual Of Methods For Baculovirus Vectors And Insect Cell Culture Procedures,* Texas Agricultural Experiment Station Bulletin No. 1555. Recombinant viruses were identified by their ability to produce a protein that could be specifically immunoprecipitated by HIV-1 antisera. Expression of SEQ ID NO:3 in the *Spodoptera frugiperda* cells resulted in production of two different r-gp120 polypeptides: 70% of the polypeptides extended from $AA_{33}$ to $AA_{498}$ of SEQ ID NO:4 and 30% of the polypeptides extended from $AA_{23}$ to $AA_{498}$ of SEQ ID NO:4.

All purification steps were performed at 4° C. The conditioned insect cell culture supernatant was clarified by filtration through a Millipore Durapore hydrophilic 2 micron filter cartridge. The clarified filtrate was diluted with an equal volume of 40 mM MES, pH 5.5 and loaded onto an S-Sepharose Fast Flow column (pre-equilibrated with 20 mM MES, pH 5.5) at a ratio of 1 ml resin per 100 ml conditioned culture supernatant. The column was washed with 20 mM MES, pH 5.5, followed by 20 mM Tris-HCl, pH 7.0. The bound proteins were eluted with 20 mM Tris-HCl, pH 7.0/300 mM NaCl. The eluate pool, containing HIV r-gp120 was diluted with an equal volume of 20 mM Tris-HCl, pH 7.0 and applied to a human rsCD4 affinity column. The affinity column contained purified human rsCD4 (described above) immobilized on Affi-Gel 10 resin at 5 mg rsCD4 per ml resin, substantially according to the resin manufacturer's directions (Bio-Rad Laboratories, Richmond, Calif., cat. no. 153-6046). The column was washed with 5 column volumes of PBS, then with 5 column volumes PBS/500 mM NaCl, and then with 5 volumes PBS. The bound HIV r-gp120 polypeptides were eluted with 50 mM sodium citrate, pH 3.0/250 mM NaCl. The eluted fractions were immediately neutralized by addition of one tenth volume of 1 M Tris-HCl, pH 7. The purified HIV r-gp120 polypeptides (approximately 0.2–0.3 mg/ml) were stored at −70° C. until use.

The RIA competition experiment was conducted substantially as described above for the CD4-V1 and CD4-V1V2 competition experiments. Specifically, each microtiter plate well was coated with anti-mouse Ig, blocked and then incubated with hybridoma culture supernatant (1F8, 5A8 or 5F2), OKT4, OKT4A or Leu3A, as described above. The purified baculovirus r-gp120 (final concentration 2.5 μg/ml) and $^{125}$I-rsCD4 were pre-incubated together 0.5 hour and then the mixture was added to each well. After incubation, the wells were washed and the bound $^{125}$I-rsCD4 was detected using a gamma counter.

The results of the ELISA cross blocking experiment are shown in Table V, which lists the percent inhibition of human rsCD4 binding to three antibody homologs of this invention (1F8, 5A8 and 5F2), two CD4 V1-specific monoclonal antibodies (Leu3A and OKT4A), and a CD4 V3V4-specific monoclonal antibody (OKT4) caused by purified HIV r-gp120.

TABLE V

HIV r-gp120 Cross Blocking: Anti-CD4 Monoclonal Antibodies Preincubated In Solution With rsCD4

| Immobilized Anti-CD4 Monoclonal Antibody | HIV r-gp120 % Inhibition rsCD4 Binding | Number Of Replicates |
|---|---|---|
| 1F8 | 11.9 | 1 |
| 5A8 | 25.0 ± 0.9 | 2 |
| 5F2 | 8.6 | 1 |
| OKT4 | −8.2 ± 11.8 | 3 |
| Leu3A | 85.1 ± 0.0 | 2 |
| OKT4A | 66.1 ± 17.9 | 3 |

The data displayed in Table V demonstrate that preincubation of human rsCD4 with HIV gp120 does not significantly block the binding of monoclonal antibodies 1F8, 5A8 or 5F2 to the r-gp120 /rsCD4 complex. In contrast, the r-gp120 nearly abolished binding of the CD4 V1-specific antibodies OKT4A and Leu3A to human rsCD4.

In our second approach, we used immunofluorescent staining to determine whether purified HIV r-gp120 would compete with 5A8, two CD4 V1-specific antibodies (Leu3A and OKT4A) and a CD4 V3V4-specific antibody (OKT4) for binding to a $CD4^+$ human cell line (H9). Two parallel sets of cell samples were stained. One set was stained only with the anti-CD4 monoclonal antibodies. The other set was preincubated with saturating HIV r-gp120 before staining with the anti-CD4 monoclonal antibodies.

Specifically, for each sample, $2\times10^5$ H9 cells (gift of Dr. Robert T. Schooley, University of Colorado Medical School, Denver, Colo.) were suspended in 50 μl of staining buffer PBS/2% FCS/0.02% sodium azide and 50 μl of antibody reagent was added. For 5A8, the antibody reagent was conditioned hybridoma cell culture supernatant containing approximately 5–20 μg/ml 5A8. The antibody reagents for the control antibodies were 10 μg/ml solutions in staining buffer of Leu3A, OKT4A or OKT4. As negative controls, two cell samples received antibody reagents containing 10 μg/ml in staining buffer of an antibody of irrelevant specificity—purified mouse myeloma proteins from MOPC 21 cells ($IgG_1$) (Litton Bionetics, Inc., Charleston, S.C., cat. no. 8402–03) or from UPC-10 cells (IgG2a) (Litton Bionetics, Inc., cat. no. 8402-24).

Samples were incubated for 30 minutes on ice, 30 then washed three times in 1 ml volumes of staining buffer. Next, 2 μl FITC-conjugated goat anti-mouse immunoglobulin (Jackson Immunoresearch, West Grove, Pa., cat. no. 115-006-062) was added at a 1:50 final dilution in staining buffer (30 μg/ml), and the samples were incubated for 20 minutes on ice, washed two times and analyzed on a FACStar fluorescence activated cell sorter.

In a parallel experiment (also with $2\times10^5$ H9 cells per tube), the cell samples were incubated with excess r-gp120 (saturating the cell surface CD4 molecules) before staining with the anti-CD4 monoclonal antibodies as described above. Specifically, 50 μl staining buffer containing 10 μg r-gp120 was added to each cell sample. After a 30 minute preincubation with r-gp120 on ice, the above antibody reagents were added, and the staining procedure was continued as described above. The cells were analyzed on a FACStar, as above.

FIG. 2 displays the results of this experiment. Each profile displays relative cell number (linear scale, x-axis) versus log fluorescence intensity of the H9 cells. Log fluorescence intensity is directly proportional to the density of stained molecules per cell. The profiles in FIGS. 2A, 2C, 2E and 2G relate to the set of experiments in which the anti-CD4 antibodies were added directly to the H9 cells. The profiles in FIGS. 2B, 2D, 2F and 2H relate to the set of experiments in which the cells were preincubated with excess HIV r-gp120 before adding the anti-CD4 antibodies. The dotted lines represent staining with the anti-CD4 monoclonal antibodies. The solid lines represent staining by the irrelevant negative control mouse IgG antibodies. The UPC-10 immunoglobulin ($IgG_2$) served as a control for OKT4A ($IgG_{2a}$) in FIGS. 2(A–B) and OKT4 ($IgG_{2b}$) in FIGS. 2(G–H), and the MOPC-21 immunoglobulin ($IgG_1$) served as a control for 5A8 ($IgG_1$) in FIGS. 2(E–F).

The results demonstrate that 5A8 binding to $CD4^+$ H9 cells is unaffected by preincubating the cells with excess HIV r-gp120. In contrast, the binding of the CD4 V1-specific antibodies Leu3A and OKT4A was completely blocked by preincubating with excess HIV r-gp120. As expected, the CD4 V3V4-specific monoclonal antibody OKT4 was unaffected by preincubating with HIV r-gp120.

Blocking of HIV-Induced Syncytia Formation

We studied the ability of antibody homologs of this invention to block HIV-induced syncytia formation between $CD4^+$ cells in order to assess their potential therapeutic benefit in the prophylaxis and treatment of AIDS, ARC and HIV infection.

In a first approach, we tested several antibody homologs of this invention for their ability to block syncytia formation between HIV-infected H9 cells and uninfected C8166 cells, as described in B. D. Walker et al., "Inhibition Of Human Immunodeficiency Virus Syncytium Formation And Virus Replication By Castanospermine", Proc. Natl. Acad. Sci. USA, 84, pp. 8120–24 (1984). HIV-infected H9 cells and C8166 cells (see Walker et al., Proc. Natl. Acad. Sci. USA, supra) are $CD4^+$ human T cell lines. C8166 is a $CD4^+$ transformed human umbilical cord blood-lymphocyte cell line, described in J. Sodroski et al., "Role Of The HTLV-III/LAV Envelope In Syncytium Formation And Cytopathicity", Nature, 322, pp. 470–74 (1986). Both cell lines were a gift from Dr. Robert T. Schooley, University of Colorado Medical School, Denver, Colo., and are also available from the AIDS Reference Reagent Program, National Institutes of Health, Bethesda, Md.

Specifically, for each sample, we incubated $5 \times 10^3$ of the chronically HIV-infected H9 cells in 100 µl "R-20 media" (RPMI 1640 culture media containing 10 mM HEPES (pH 6.8) and 2 mM glutamine, supplemented with 20% FCS), for 30 minutes at 37° C. in a 5% $CO_2$ atmosphere, with 50 µl hybridoma cell culture supernatant containing approximately 5–20 µg/ml of an antibody homolog of this invention. The culture supernatants were tested at serial two-fold dilutions in R-20 media from 1:2 to 1:256. We then added $15 \times 10^3$ uninfected C8166 cells in 100 µl R-20 media, to give a final volume of 200 µl in each well. The samples were incubated at 37° C. in a 5% $CO_2$ atmosphere after adding the C8166 cells, and the number of syncytia per well was then scored by visual inspection under a light microscope.

The maximum number of syncytia per well was established in the absence of any added anti-CD4 antibody-containing culture supernatant. In one sample, 100 µl of culture supernatant containing approximately 5–20 µg/ml of an isotype-matched irrelevant mouse immunoglobulin (hybridoma culture supernatant) was added as a negative control for any non-specific blocking effects. As a positive control, the CD4 V1-specific monoclonal antibody Leu3A was tested at a number of concentrations, ranging from 2.5 µg/ml down to 0.04 µg/ml.

The results of this experiment are depicted in Table VI. Data are expressed as the reciprocal of the hybridoma culture supernatant dilution that resulted in 50% blocking of syncytia formation.

TABLE VI

Blocking of Syncytia Formation
By Antibody Homologs Of This Invention

| Hybridoma<br>Culture Supernatant | Reciprocal Of<br>Dilution Blocking 50% |
| --- | --- |
| 5A8 | >256 |
| 1F8 | (not assayed) |
| 5F8 | 8 |
| Controls | |
| irrelevant IgG | no blocking |
| Leu3A | blocking* |

*Greater than or equal to 80% blocking down to 0.04 µg/ml.

In several independent experiments using the above assay, the concentration of OKT4 (a CD4 V3V4-specific antibody) required to cause 50% blocking of syncytia formation ranged from 1–10 µg/ml.

The above assay was also performed several times with purified 5A8, purified Leu3A, and purified 5A8 together with purified Leu3A. When Leu3A and 5A8 were administered together, synergistic inhibition was observed. For example, in one experiment, both Leu3A and 5A8 inhibited syncytia formation 50% at a concentration of 0.02 µg/ml when used alone. At 0.008 µg/ml of either Leu3A or 5A8 alone, we observed 30% and 20% syncytia blocking, respectively. However, when Leu3A and 5A8 were administered together only 0.004 µg/ml of each was required for 50% inhibition. Similar synergistic effects were observed in 3 out of 4 additional experiments.

In an alternative syncytia assay, we accurately quantified the ability of purified 5A8 to block HIV-induced syncytia formation between human $CD4^+$ Jurkat cells and transformed CHO cells expressing recombinant gp160 on their surface ("r-gp160-CHO cells"). The Jurkat cells were a gift of Dr. Timothy Springer, Dana Farber Cancer Institute, Boston, Mass., and are also available from American Type Culture Collection, Rockville, Md., cat. no. TIB152. The r-gp160-CHO cells were deposited with the In Vitro International Inc. culture collection in Linthicum, Md., under accession number IVI-10261 and were transferred to the American Type Culture Collection, Rockville, Md., under accession number CRL 10885. The nucleotide sequence of the HIV gp160 gene used to transform those cells is set forth in SEQ ID NO:1, and the amino acid sequence of the gp120/gp41 polypeptides it encodes also is set forth in SEQ ID NO:1, as well as in SEQ ID NO:2. For the purpose of comparison, we also used this assay to test the syncytia-blocking ability of two CD4 V1-specific monoclonal antibodies (OKT4A and Leu3A) and one CD4 V3V4-specific monoclonal antibody (2-103-D11, similar to OKT4 in behavior).

The purified 5A8 antibody used in this assay was prepared as follows. 5A8 hybridoma cells ($1 \times 10^6$) were injected intraperitoneally into Balb/c mice (primed with pristane), to generate ascites. 5A8 ascites was stored frozen at −20° C.

until use. After thawing, the 5A8 ascites was centrifuged at approximately 500×$g_{av}$ for 20 minutes at room temperature. The supernatant was filtered through a 0.45 µM Millipore filter, and then diluted six-fold and purified according to the manufacturer's directions using an Affi-Gel Protein A MAPSII column (Bio-Rad Laboratories, cat. no. 1536159). The sample was then dialyzed extensively against phosphate buffered saline at 4° C. The dialyzed 5A8 preparation was divided into aliquots and stored at −70° C. until use.

Specifically, r-gp160-CHO cells were plated into 96-well (flat bottomed) microtiter plates at 1.5×10⁴ cells/well in 100 µl media (a MEM supplemented with 10% dialyzed FCS, 4 mM L-glutamine and 500 nM methotrexate), and incubated overnight at 37° C. in a 5% $CO_2$ atmosphere. After incubation, the plates were flipped onto absorbent paper to remove the media from the wells and 100 µl of antibody reagent was added to each well (each antibody concentration was tested in triplicate); these samples yield "test cpm". As antibody reagent, we added purified 5A8, Leu3A, OKT4 or 2-103-D11 (purified as described above for 5A8), at concentrations ranging from 0.026 to 10,000 ng/ml. We then added 6×10⁴ ⁵¹Cr-labelled CD4⁺ Jurkat cells (prepared as described infra) in 100 µl RPMI media supplemented with 10% heat-inactivated FCS, 2 mM glutamine and 100 U/ml penicillin G and streptomycin. To control for nonspecific ⁵¹Cr release from the Jurkat cells, we added to a well 6×10⁴ ⁵¹Cr-labelled Jurkat cells in a volume of 200 µl; this sample yielded "background cpm".

The microtiter plates were incubated at 37° C. in a 5% $CO_2$ atmosphere for 17–19 hours. After the incubation, the wells were visually inspected under a light microscope for syncytia lysis in the positive control wells and inhibition of lysis in the wells containing anti-CD4 antibodies expected to block syncytia formation. The plates were centrifuged three to four minutes at approximately 400×$g_{av}$. Supernatant (100 µl) was withdrawn from each well without touching the bottom and placed in Titertube Microtubes (Bio-Rad Laboratories, cat. no. 223-9390). The Microtubes were then transferred individually to counting vials and the cpm emitted by each vial was measured in a gamma counter (Beckman).

To determine the total counts added to each assay ("total cpm"), 6×10⁴ of the ⁵¹Cr-labelled Jurkat cells were added to a scintillation vial, and then lysed in the vial by adding 0.2N NaOH and 1% sodium dodecyl sulfate in PBS. The cpm emitted by this control vial was then measured in the gamma counter.

The ⁵¹Cr-labelled Jurkat cells were prepared as follows. Jurkat cells from flasks were spun down, resuspended in fresh growth media (RPMI media supplemented with 10% heat-inactivated FCS, 2 mM L-glutamine and 100 U/ml penicillin G and streptomycin) and counted. Fresh ⁵¹Cr was added to 50-ml conical bottom sterile tubes at the following ratios: (1) 100 µCi ⁵¹Cr (100 µl) added to 900 µl media containing up to 5×10⁶ cells; (2) 200–250 µCi ⁵¹Cr (200–250 µl) added to 800–750 µl media containing from 5×10⁶ up to 10×10⁶ cells. The cells were incubated at 37° C. under 5% $CO_2$ with loose caps for 45 minutes, with occasional gentle shaking. After incubation, the cells were washed three times in their growth media (30 ml per wash). The washed cells were resuspended in 1 ml of growth media, counted, and added to the syncytia assays. The cells were used in the assay within 30 minutes of their preparation.

Percent inhibition was calculated as follows.

$$\frac{\text{test cpm} - \text{background cpm}}{\text{total cpm} - \text{background cpm}} \times 100 = \% \text{ syncytia lysis}$$

% Inhibition =

$$\left(1 - \frac{\% \text{ syncytia lysis in presence of anti-}CD4\text{ }MAb}{\% \text{ syncytia lysis in absence of anti-}CD4\text{ }MAb}\right) \times 100$$

FIGS. 3 and 4 display the results of these experiments, plotting percent syncytia inhibition (calculated as described above) versus concentration (ng/ml) of antibody. FIG. 3 shows the effect on syncytia formation of 0.026 to 2,000 ng/ml of 5A8, Leu3A and OKT4A. Unexpectedly, FIG. 3 demonstrates that the efficacy of 5A8 is comparable to that of Leu3A and OKT4A, with 50% syncytia blocking achieved at approximately 10 ng/ml. FIG. 4 shows the effect on syncytia formation of 3.2 to 10,000 ng/ml of 5A8, Leu3A, OKT4A and the "OKT4-like" monoclonal antibody 2-103-D11. FIG. 4 demonstrates that the CD4 V3V4-specific antibody (2-103-D11) blocked syncytia formation only at a concentration several orders of magnitude higher than that required by 5A8.

Blocking Of HIV Infection Of CD4⁺ Cells

We studied the ability of antibody homologs of this invention to block infection of CD4⁺ cells by HIV in order to assess their potential therapeutic benefit in the prophylaxis and treatment of AIDS, ARC and HIV infection. For these measurements, we used a microassay based on the protocol described in M. Robert-Guroff et al., "HTLV-III-Neutralizing Antibodies In Patients With AIDS And AIDS-Related Complex", *Nature*, 316, pp. 72–74 (1985).

In a first experiment, 200 $TCID_{50}$ (200 times the lowest dilution of virus that reproducibly infects one half the cultures inoculated) of HIV isolate HTLV-IIIB [Robert-Guroff et al., *Nature*, supra] in R-20 media was added to 20 µl of an undiluted hybridoma culture supernatant containing anti-CD4 monoclonal antibodies or an irrelevant mouse $IgG_1$-containing culture supernatant (as negative control) and 4×10⁴ C8166 cells in 10 µl R-20 media. HTLV-IIIB was a gift from Dr. Robert T. Schooley, University of Colorado Medical School, Denver, Colo., and is also available from the AIDS Reference Reagent Program, National Institutes of Health, Bethesda, Md.). Aliquots of each mixture were added to three wells (15 µl/well) and each well was brought to a total volume of 200 µl with R-20 media. In a second experiment, cells were preincubated with the hybridoma culture supernatant for 30 minutes at 37° C. before adding 100 $TCID_{50}$ of HIV. Preincubation had no obvious effect on 5A8 blocking of infection.

The wells from both experiments were visually scored under a light microscope four to eight days later for the onset of infection, as evidenced by the presence of syncytia. A well was scored as positive for infection if it contained more than 5 syncytia, with each syncytium being greater than 3 cell diameters in diameter.

We considered 2 to 3 positive wells to be indicative of a successful infection, whereas 0 or 1 positive wells was indicative of effective blocking.

Table VII displays the effects of 5A8 (5–20 µg/ml), 1F8 (5–20 µg/ml), 5F2 (~5 µg/ml), the CD4 V3V4-specific mouse monoclonal $IgG_1$ 2-103-D11 (~5 µg/ml) and an irrelevant mouse $IgG_1$ culture supernatant (5–20 µg/ml) on the infection by 200 $TCID_{50}$ of HIV of CD4⁺ C8166 cells, without preincubation of the cells and the antibodies. Table VIII displays the effects of the same antibodies, at the same concentrations, on the infection by 100 TCID$_{50}$ of HIV, with preincubation of the cells and the antibodies.

TABLE VII

Infection By 200 TCID$_{50}$ HIV In The Presence Of Antibody Homologs Of This Invention: No Preincubation

| Monoclonal Antibody | Number Of Wells Infected (of 3 possible) | |
|---|---|---|
| | Day 5 | Day 7 |
| 5A8 | 0 | 0 |
| 1F8 | 0 | 1 |
| 5F2 | 3 | 2 |
| Controls | | |
| 2-103-D11 | 1 | 3 |
| irrelevant IgG$_1$ | 1 | 2 |
| no antibody | 3 | 3 |

TABLE VIII

Infection By 100 TCID$_{50}$ HIV In The Presence Of Antibody Homologs Of This Invention: With Preincubation

| Monoclonal Antibody | Number Of Wells Infected (of 3 possible) | |
|---|---|---|
| | Day 4 | Day 8 |
| 5A8 | 0 | 1 |
| 1F8 | 0 | 2 |
| 5F2 | 2 | 1 |
| Controls | | |
| 2-103-D11 | 1 | 3 |
| irrelevant IgG$_1$ | 1 | 3 |
| no antibody | 0 | 2 |
| no antibody | 3 | 3 |
| no antibody | 3 | 3 |

Tables VII and VIII demonstrate that 5A8 was able to block reproducibly the establishment of HIV infection in CD4$^+$ cells. 1F8 and 5F2 also showed evidence of being able to block HIV infection.

We performed additional infectivity experiments using a recent patient HIV isolate (isolate 0108E, Massachusetts General Hospital Phase I Reception Clinical Trial: R. T. Schooley et al., "A Phase I/II Escalating Dose Trial Of Recombinant Soluble CD4 Therapy In Patients With AIDS Or AIDS-Related Complex", Ann. Int. Med., 112, pp. 247–53 (1989)) instead of the laboratory strain (HTLV-IIIB) used in the experiments described above.

In this experiment, 500 µl of antibody reagent was added to 250 µl of "R-3 media" (R-20 media supplemented with 25 U/ml recombinant T cell growth factor ("r-IL2" or "r-TCGF") manufactured by Biogen, Inc., Cambridge, Mass.) containing 5–10 TCID$_{50}$ of HIV isolate 0108E and 250 µl of R-3 media containing 1×10$^6$ phytohemagglutinin ("PHA")-activated human peripheral blood lymphocytes ("PBLs") (prepared as described below). The antibody reagents used in the experiment presented in Table IX were 5A8-containing hybridoma culture supernatant (5–20 µg/ml) and an isotype-matched IgG$_1$-containing culture supernatant (5–20 µg/ml) as a negative control, both diluted in R-20 media. The antibody reagents used in the experiment presented in Table X were purified 5A8 (described above), purified Leu3A as a positive control, and isotype-matched, purified mouse IgG$_1$ MOPC-21 as a negative control (Litton Bionetics, cat. no. 8402-031), all diluted in R-20 media.

The PHA-activated human PBLs were prepared as follows. Whole Blood (Red Cross) was layered on Histopaque (Sigma Chemical Co., cat. no. 1077-1), and centrifuged at 400×g$_{av}$ for 40 minutes, at room temperature. PBLs were collected from the interface, washed three times in unsupplemented RPMI-1640 media, and counted. The PBLs were then resuspended at 4×10$^6$ cell/ml in R-3 media supplemented with 1 µg/ml PHA-P (Difco, Springfield, N.J., cat. no. DF 3110 56 4), and incubated for 3 days. After the incubation, the cells were frozen (10% DMSO in R-20 media) and stored at −80° C. until use. Before use, the activated PBLs were thawed and cultured in R-3 media for 5 days.

In the experiment using purified 5A8 (Table X), the PHA-activated PBLs were preincubated with the antibody reagents for 1 hour at 37° C. before adding virus. In the other experiment (Table IX), using 5A8 hybridoma culture supernatant, there was no such preincubation. In both experiments, the cells were incubated with the antibody reagents and the virus for 24 hours at 37° C., under 5% CO$_2$. Each sample of cells was washed three times with R-20 media, divided into two wells, and incubated at 37° C. under 5% CO$_2$ in R-3 media. Every 3–4 days, 450 µl of cell supernatant was withdrawn and assayed for the presence of HIV core antigen p24 (an indicator of HIV infection). After each such withdrawal, 500 µl R-3 media was added to each well.

We assayed for HIV p24 by solid phase ELISA using a commercially available kit that employs anti-p24 monoclonal antibody immobilized in microtiter plate wells to capture p24 core antigen present in the sample (NEN Research Products, E. I. DuPont de Nemours and Co., Inc., Boston, Mass., "HIV Core Profile ELISA", cat. nos. NEK-060, NEK-060A, NEK-060B). The kit was used as specified by the manufacturer, with the extended range standard curve indicated in Appendix C of the procedure booklet supplied with the kit.

A well was classified as "infected" if it contained greater than 0.1 ng/ml HIV p24.

The results of these experiments are shown in Tables IX and X.

TABLE IX

Infection By 5–10 TCID$_{50}$ Of A Patient HIV Isolate In The Presence Of 5A8 Culture Supernatant

| | Number Of Wells Infected (of 2 possible) | | |
|---|---|---|---|
| | Day 7 | Day 15 | Day 25 |
| Dilution Of 5A8 Sup. | | | |
| 1:4 | 0 | 0 | 0 |
| 1:8 | 1 | 1 | 1 |
| 1:16 | 0 | 0 | 0 |
| 1:32 | 1 | 1 | 1 |
| Dilution Of IaG$_1$ Control Sup. | | | |
| 1:4 | 0 | 1 | 1 |
| 1:8 | 1 | 2 | 2 |
| 1:16 | 2 | 2 | 2 |
| 1:32 | 2 | 2 | 2 |

TABLE X

Infection By 5–10 TCID$_{50}$ Of A Patient HIV Isolate In The Presence Of Purified 5A8, Leu3A And IaG$_1$ Control Antibodies

| Dose (μg/ml) | Number of Wells Infected On Day 12 (of 2 possible) | | |
|---|---|---|---|
| | 5A8 | Leu3A | IgG$_1$ control |
| 2.5 | 0 | 0 | 2 |
| 1.25 | 1 | 1 | 1 |
| 0.62 | 0 | 0 | 2 |
| 0.31 | 0 | 0 | 2 |
| 0.16 | 0 | 0 | 2 |
| 0.08 | 0 | 0 | 1 |

Tables IX and X demonstrate that 5A8 is an extremely effective blocker of infection by an HIV patient isolate. 5A8-containing culture supernatant blocked infection even at a 1:16 dilution. Purified 5A8 blocked infection by the patient virus isolate at a concentration as low as 0.08 μg/ml, the lowest concentration tested, which was comparable to Leu3A.

Immunosuppressiveness

We compared the immunosuppressiveness of an antibody homolog of this invention (5A8) with that of two CD4 V1-specific anti-CD4 antibodies (Leu3A and OKT4A) using a T cell proliferation assay modified after the protocol described in E. G. Engleman et al., "Activation Of Human T Lymphocyte Subsets: Helper and Suppressor/Cytotoxic T Cells Recognize And Respond To Distinct Histocompatibility Antigens", *J. Immunol.*, 127, pp. 2124–29 (1981) ("Tetanus Toxoid" or "TT" assay). In this assay, human PBLs are treated with tetanus toxoid, which stimulates their proliferation. If an immunosuppressive substance is present when the tetanus toxoid is added, then proliferation will be impeded. Proliferation is quantified as 3H-thymidine incorporation by the cells.

Human PBLs were isolated by diluting 10 ml blood two-fold with unsupplemented RPMI-1640 media and layering the mixture over 10 ml of Lymphocyte Separation Media in a 50-ml tube at room temperature. The tube was centrifuged at room temperature for 30 minutes at 400×g$_{av}$. PBLs were collected from the interface, washed two times with unsupplemented RPMI-1640 media, counted, and used in the Tetanus Toxoid assay as described below.

The Tetanus Toxoid assay was performed in 96-well flat bottom microtiter plates, with each well containing human PBLs and tetanus toxoid. Antibody reagents were added to some of the wells, with the total volume in each well being 200 μl. Wells containing only cells (no antibody reagent or tetanus toxoid) constituted the "background" for this assay.

The assay was performed in triplicate. Assay components were added in the following order: (1) 50 μl "assay media" (RPMI-1640 supplemented with 10% heat-inactivated fetal bovine serum (Hazelton Biologics, Inc., Lenexa, Kans., cat. no. 12-10378P), 2 mM L-glutamine and 100 Units/ml penicillin G and streptomycin); (2) 50 μl assay media (for "background" wells) or antibody reagent (final TT assay concentrations ranging from 10 to 0.1 μg/ml purified 5A8, Leu3A, OKT4A, MOPC 21 or UPC 10; (3) 50 μl of 40 μg/ml tetanus toxoid diluted in assay media (final TT assay concentration was 10 μg/ml); and (4) 1.5×10$^5$ PHA-activated PBLS, prepared as described above.

The tetanus toxoid was obtained as a concentrate from the Massachusetts Public Health Biologic Laboratory, Jamaica Plain, Mass., and was dialyzed at 4° C. against 4 L of PBS for over 48 hours before use. The CD4 V1-specific antibodies OKT4A (isotype IgG$_2$) and Leu3A (isotype IgG$_1$) were obtained from Ortho Diagnostic Systems and Becton Dickinson, respectively. The purified 5A8 (isotype IgG$_1$) was produced as described above. The purified MOPC 21 control antibody (Litton Bionetics) is isotype matched to 5A8 and Leu3A. The purified UPC 10 antibody is isotype matched to OKT4A.

Following the addition of all reagents to the assays, the plates were incubated at 37° C. in a 5% CO$_2$ atmosphere for four and five days. On the fourth and fifth days, the plates were pulsed with 1 μCi of $^3$H-thymidine (NEN Research Products, cat. no. NET-027) for 6–18 hours at 37° C., 5% CO$_2$. After incubation with label, the plates were harvested with a PHD Cell Harvester (Cambridge Technologies, Inc., Cambridge, Mass.), and filters containing the radioactive DNA were transferred to scintillation vials, to which scintillation fluid was added (3 ml per vial) (Scintiverse, Fisher Scientific Co., cat. no. SK12-4). The radioactivity of the vials was counted in a β-counter (Beckman Model LS 3801).

The results of the TT assays are displayed in FIGS. 5 (day 4) and 6 (day 5). FIGS. 5 and 6 show the effect on proliferation (identified as cpm×10$^3$ of 5A8 and the various control antibodies. The bars labelled "TT Control" show the baseline growth of the cells without TT stimulation (open bar) and the TT response without any antibody (solid bar). The effect on proliferation of antibody only, without TT stimulation, is indicated by the bars with large spots. The figures also show the effect on proliferation after TT stimulation (i.e., inhibition of TT response) of the various antibodies at concentrations of 10 μg/ml (bars with dots) (MOPC 21 and 5A8 only), 1 μg/ml (bars with diagonal stripes) (every antibody) and 0.1 μg/ml (bars with crosshatching) (every antibody).

The data in FIGS. 5 and 6 demonstrate that 5A8 was less immunosuppressive than OKT4A on both days four and five of the assay. The immunosuppressiveness of 5A8 was comparable to Leu3A in these assays.

5A8 Epitope Mapping

As part of our effort to characterize 5A8's mechanism of action, we performed several studies to map the CD4 epitope bound by 5A8. The results of these studies are summarized below.

5A8 was found to recognize nonreduced, SDS-denatured CD4 on a Western blot. However, 5A8 did not bind to reduced CD4 or to proteolytic fragments of CD4 (five different proteases were used). Thus, 5A8 appears to recognize a conformational epitope of CD4. This result is consistent with the fact that 5A8 was raised against r-CD4$^+$-CHO cells, which presumably display CD4 having its native conformation, rather than against denatured CD4 or CD4 fragments.

We studied the binding of 5A8 to a panel of mouse/human chimeric CD4 molecules. 5A8 does not recognize mouse CD4. Accordingly, by studying the binding of 5A8 to various mouse/human chimeric CD4 molecules, we hoped to identify the human CD4 residues required for 5A8 binding.

Gene constructs encoding the mouse/human CD4 chimeras were provided by Daniel R. Littman of the Howard Hughes Medical Institute, University of California, San Francisco, Calif. and are described in N. R. Landau et al., "The Envelope Glycoprotein Of The Human Immunodeficiency Virus Binds To The Immunoglobulin-Like Domain Of CD4", *Nature*, 334, pp. 159–62 (1988). We transiently transformed COS-7 cells with expression vectors containing those constructs, and assessed 5A8's ability to bind to the various expressed chimeras by FACS analysis. As controls we used the anti-human CD4 monoclonal antibodies Leu3a and OKT4, and the anti-mouse CD4 monoclonal antibody GK1.5. Antibody binding was assessed quantitatively by titering 5A8 or the control antibodies, at sub-saturating concentrations, for each chimeric form.

The results of the 5A8/chimeric CD4 binding studies indicate that: (1) human CD4 V1V2 residues are both required and sufficient for 5A8 binding; (2) human V1 residues (through amino acid 83) are not required for efficient 5A8 binding; (3) human residues of the rod-like B strand which connects V1 and V2 ($AA_{83}$–$AA_{105}$) significantly influence 5A8 binding [see J. Wang et al., *Nature*, 348, pp. 411–18 (1990) for human CD4 crystal structure]; and (4) human CD4 V2 residues $AA_{105}$–$AA_{131}$ (strands B and C of V2) are absolutely required for 5A8 binding.

We also studied the binding of 5A8 to various point and cluster mouse/human substitution mutants of rsCD4. The substituted amino acid positions of the mutants were as follows: $AA_{60}$ (VI), $AA_{121}$–$AA_{124}$ (V2), $AA_{127}$–$AA_{134}$ (V2), $AA_{165}$ (V2), $AA_{220}$–$AA_{226}$ (V3) and $AA_{240}$–$AA_{252}$ (V3). Specifically, we assesed the ability of these mutants to block binding of 5A8 to $CD4^+$ cells, in comparison to their ability to block binding of the CD4 V3V4-specific antibody OKT4 to $CD4^+$ cells.

At a concentration of 1 µg/ml, every mutant form blocked OKT4 binding comparably (about 60%). In contrast, mutants at $AA_{121}$–$AA_{124}$ (connecting loop between strand B and C of V2) and $AA_{127}$–$AA_{134}$ (strand C of V2) failed to block 5A8 binding to $CD4^+$ cells. These data localize residues within V2 which are critical for 5A8 binding, agreeing well with those identified using the mouse/human chimeras. In addition, residue 165 was identified as contributing to recognition of CD4 by 5A8, although it was considerably less important than $AA_{121}$–AA124 and $AA_{127}$–$AA_{134}$.

Immune System Effects Of 5A8 In Rhesus Monkeys

Monoclonal antibody 5A8 or a control isotype-matched monoclonal antibody (MOPC21) was administered to rhesus macaque monkeys in order to assess the impact of 5A8 on normal immune function in vivo. Several indicia of immune function were examined before and at various time points after 5A8 or MOPC21 infusion. Specifically, we assessed whether 5A8 caused (a) a decrease in the number of circulating $CD4^+$ cells in vivo, (b) a modulation of CD4 from the surface of $CD4^+$ cells, (c) a decrease in the circulating peripheral white blood cell counts in vivo or (d) a decrease in the antibody titer elicited in response to a foreign antigen (tetanus toxoid) in vivo.

We determined that 5A8 had no significant effect on any of those indicia of immunosuppression in vivo. Thus, it appears that 5A e has no adverse effects on the immune system in vivo.

1. Injection And Sampling Protocols

Two adult rhesus monkeys (Mn 261–85 and Mn 251-87) were infused intravenously with 3 mg/kg 5A8 purified as described above or with control MOPC21 (Mn 265-85 and Mn 265-87) (4 monkeys total) on days 0, 2 and 4. On days 3 and 21, 0.5 ml alum-adsorbed tetanus toxoid (Squibb-Connaught) (standard human dose) was administered intramuscularly. Blood was drawn from each monkey prior to the first 5A8 injection and on each of days 0–4, 6, 9, 14, 21 or 24, 28, 35 and 42, and analyzed as described below.

2. Peripheral White Blood Cell Counts

We assayed blood samples from both groups of monkeys (5A8-injected and MOPC21-injected) for their counts of white blood cells using standard staining of blood smears. The results are displayed in FIGS. 7(A–B).

Figure 7A:
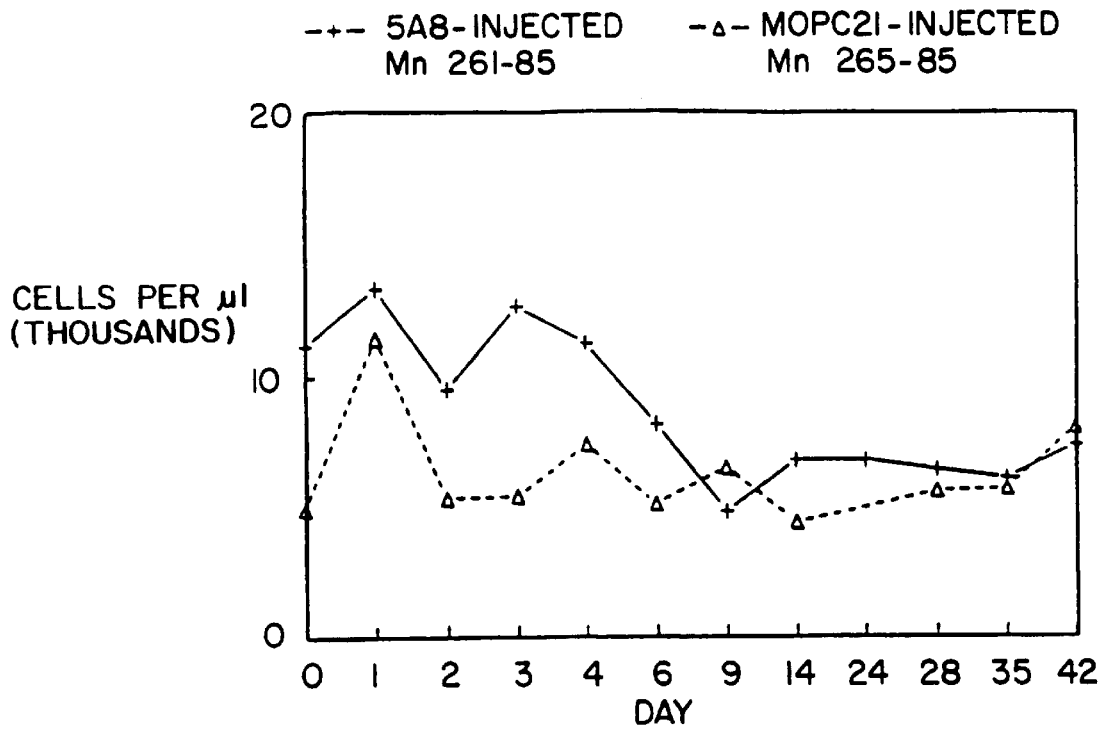
FIGS. 7(A–B) depicts the peripheral white blood cell count of rhesus monkeys at various time points before, during and after a course of treatment with 5A8 (solid lines, Mn 261-85 in FIG. 7A and Mn 251-87 in FIG. 7B) or the isotype-matched control monoclonal antibody MOPC21 (dashed lines, Mn 265-85 in FIG. 7A and Mn 265-87 in FIG. 7B). The y-axes depict white blood cells (in thousands) per microliter of blood. The x-axes depict days, where 5A8 or MOPC21 was injected on days 0, 2 and 4.
Figure 7B:
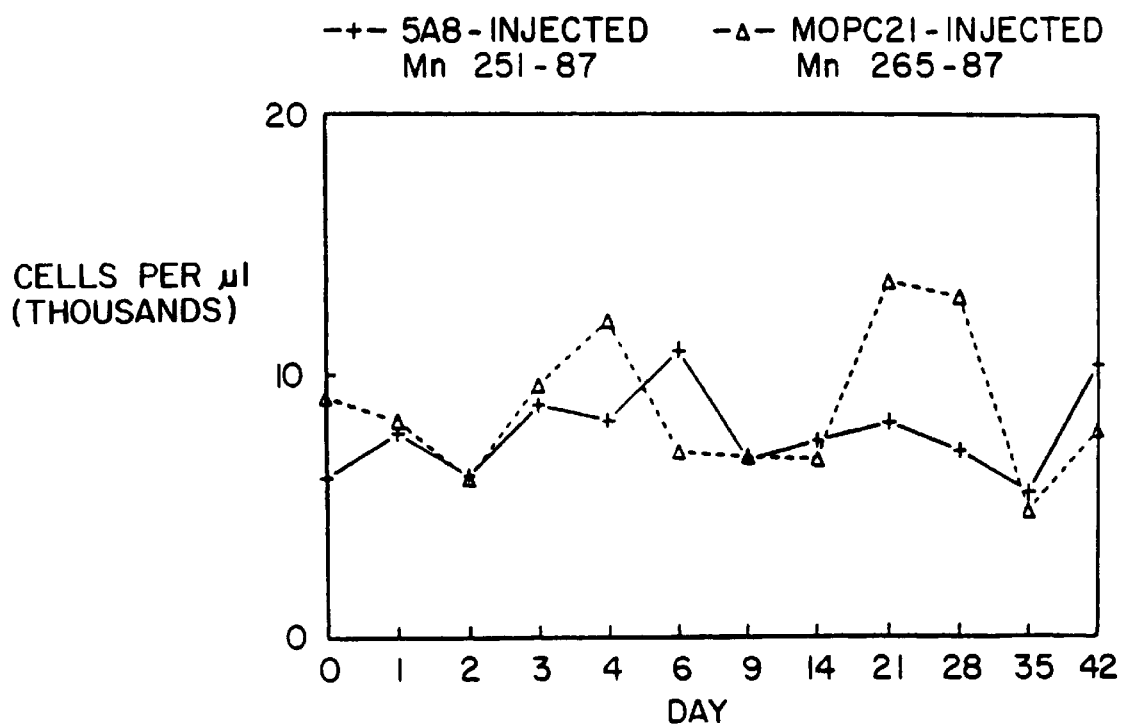

As shown in FIGS. 7(A–B), there was no significant difference between the 5A8-injected and control groups with respect to their white blood cell counts, before or after injection of the monoclonal antibodies.

3. Circulating $CD4^+$ Cell Counts And Modulation Of Cell Surface CD4

We assayed blood samples from both groups of monkeys (5A8-injected and MOPC21-injected) for their counts of $CD4^+$ cells. $CD4^+$ cell count was determined by FACS analysis, both after direct staining with FITC-OKT4 and after indirect staining with 5A8 (i.e., in vitro incubation with excess 5A8 followed by FITC-goat anti-mouse Ig). The protocols used were analogous to the FACS protocols described above. The results of these experiments are depicted in FIGS. 8(A–B).

Figure 8A:
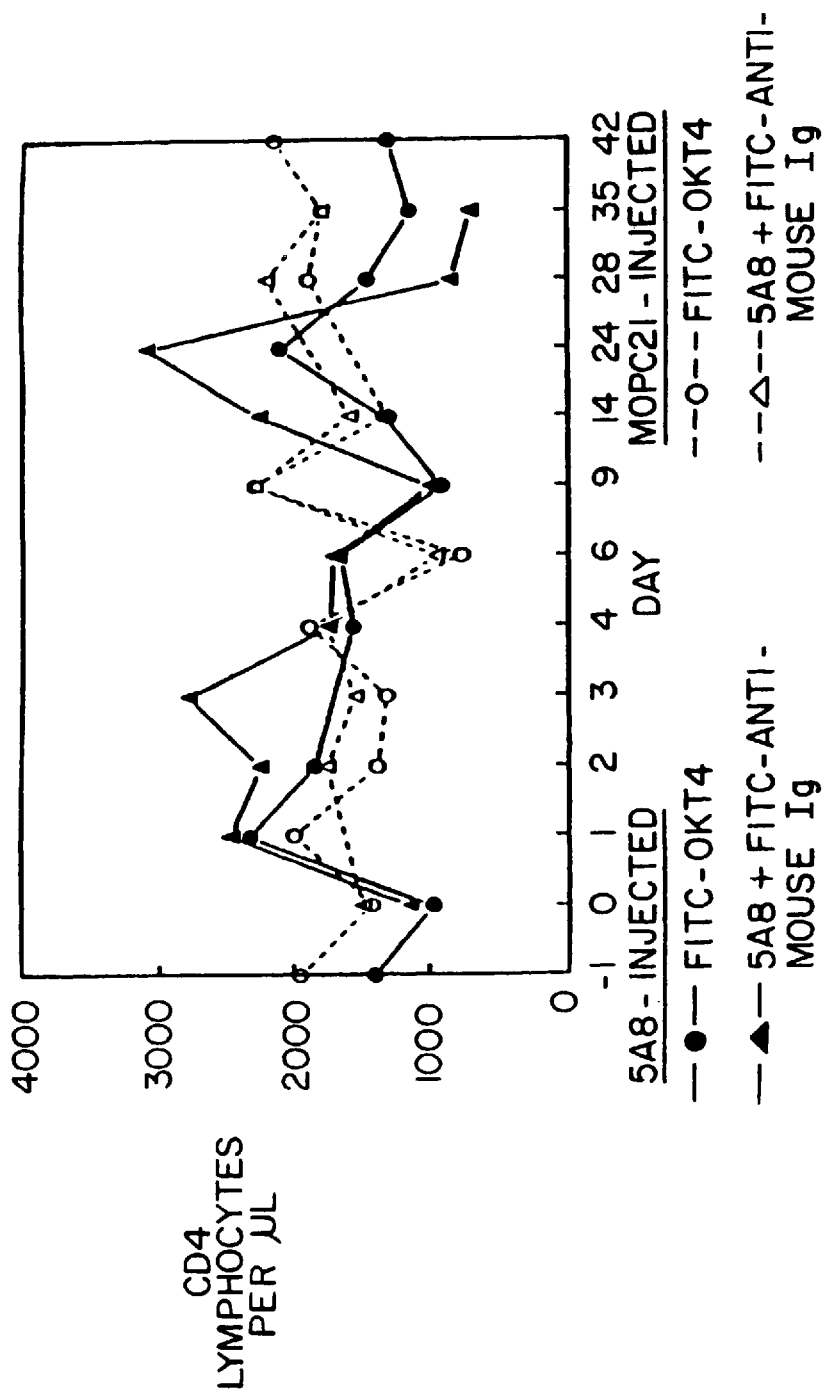
FIGS. 8(A–B) depicts the number of peripheral $CD4^+$ lymphocytes in rhesus monkeys at various time points before, during and after a course of treatment with 5A8 (solid lines, Mn 261-85 (FIG. 8A) and Mn 251-87 (FIG. 8B)) or the isotype-matched control monoclonal antibody MOPC21 (dashed lines, Mn 265-85 (FIB. 8A) and Mn 265-87 (FIG. 8B)). $CD4^+$ cell number is quantitated by FACS analysis after staining with the fluorescently labelled CD4 V3V4-specific monoclonal antibody FITC-OKT4 (open and closed circles) or by FACS analysis after incubating isolated cells with excess 5A8 in vitro and then staining with fluorescently labelled goat anti-mouse Ig (open and closed triangles). The y-axes depict $CD4^+$ cell number per microliter. The x-axes depict days, where 5A8 or MOPC21 was injected on days 0, 2 and 4.
Figure 8B:
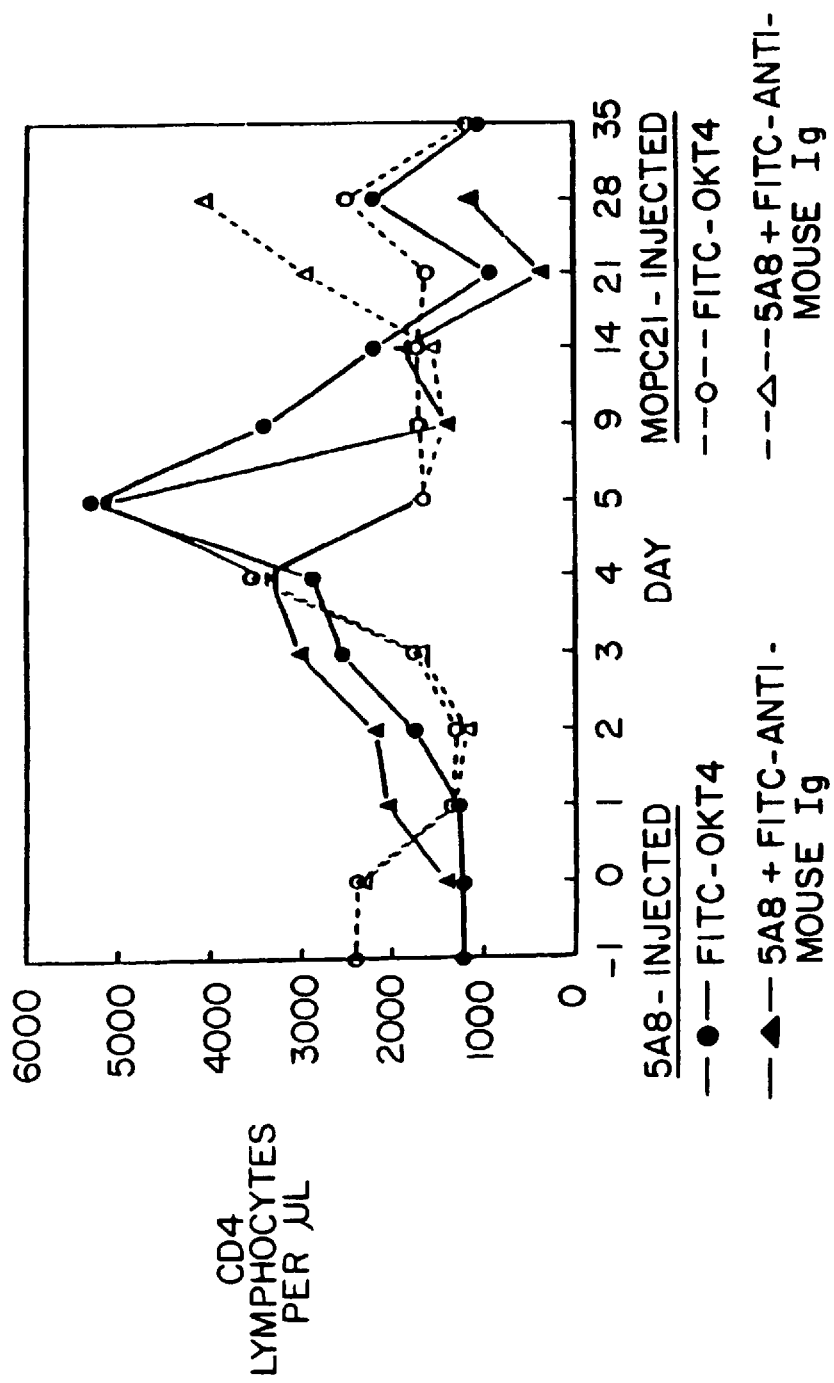

As shown in FIG. 8(A–B), the number of circulating $CD4^+$ cells in the 5A8-injected animals and the control animals did not change significantly after injection of the antibodies. Moreover, the intensity of staining for CD4 was not significantly different between the 5A8-injected and control monkeys. All other blood cell parameters, including CD2, CD8 and CD20 staining, were similar between 5A8-injected and control animals (data not shown).

These results demonstrate that 5A8 did not significantly deplete $CD4^+$ cells and did not singificantly modulate CD4 from the surface of circulating $CD4^+$ cells.

4. Binding Of 5A8 To Rhesus $CD4^+$ Cells In Vivo

Saturation for CD4 binding sites on the monkey $CD4^+$ peripheral T cells was determined by (1) FACS analysis after staining with FITC-goat anti-mouse Ig, (2) FACS analysis after adding additional 5A8 plus FITC-goat anti-mouse Ig (no increase in staining intensity), and (3) the inability of cells recovered from the 5A8-injected monkeys to bind measurable amounts of FITC-5A8.

Saturation for CD4 binding sites on all circulating $CD4^+$ cells of the 5A8-injected rhesus monkeys was observed by day 1 and persisted for at least 9 days. In addition, a lymph node biopsy of a 5A8-injected monkey on day 4 revealed complete penetration and coating by 5A8 of lymph node $CD4^+$ cells. No $CD4^+$ cell coating was observed in the control monkeys. $CD4^+$ cell coating by 5A8, as measured by indirect staining with FITC-goat anti-mouse Ig, could not be detected after day 14.

5. 5A8 and Anti-5A8 Serum Levels

Using an anti-mouse Ig sandwich ELISA, 5A8 levels were found to be high through day 9 (about 10–100 µg/ml), but dropped off sharply between days 9 and 14. Conversely, monkey anti-mouse Ig titers (detected by ELISA on 5A8-coated plates) appeared between days 9 and 14. It is not clear whether complexed 5A8 was present after day 9 because the anti-mouse Ig trap might fail to detect it.

6. Antibody Response To Tetanus Toxoid

We assessed the possible effect of 5A8 on the monkeys' ability to generate antibodies upon infusion of a foreign antigen—tetanus toxoid. We immunized the 5A8-injected and control animals with tetanus toxoid adsorbed to alum (i.m.) on day 3, after complete coating of $CD4^+$ cells had been achieved in the 5A8-injected animals, and on day 21. The anti-tetanus toxoid titers elicited in the monkeys over time are displayed in FIG. 9.

Figure 9:
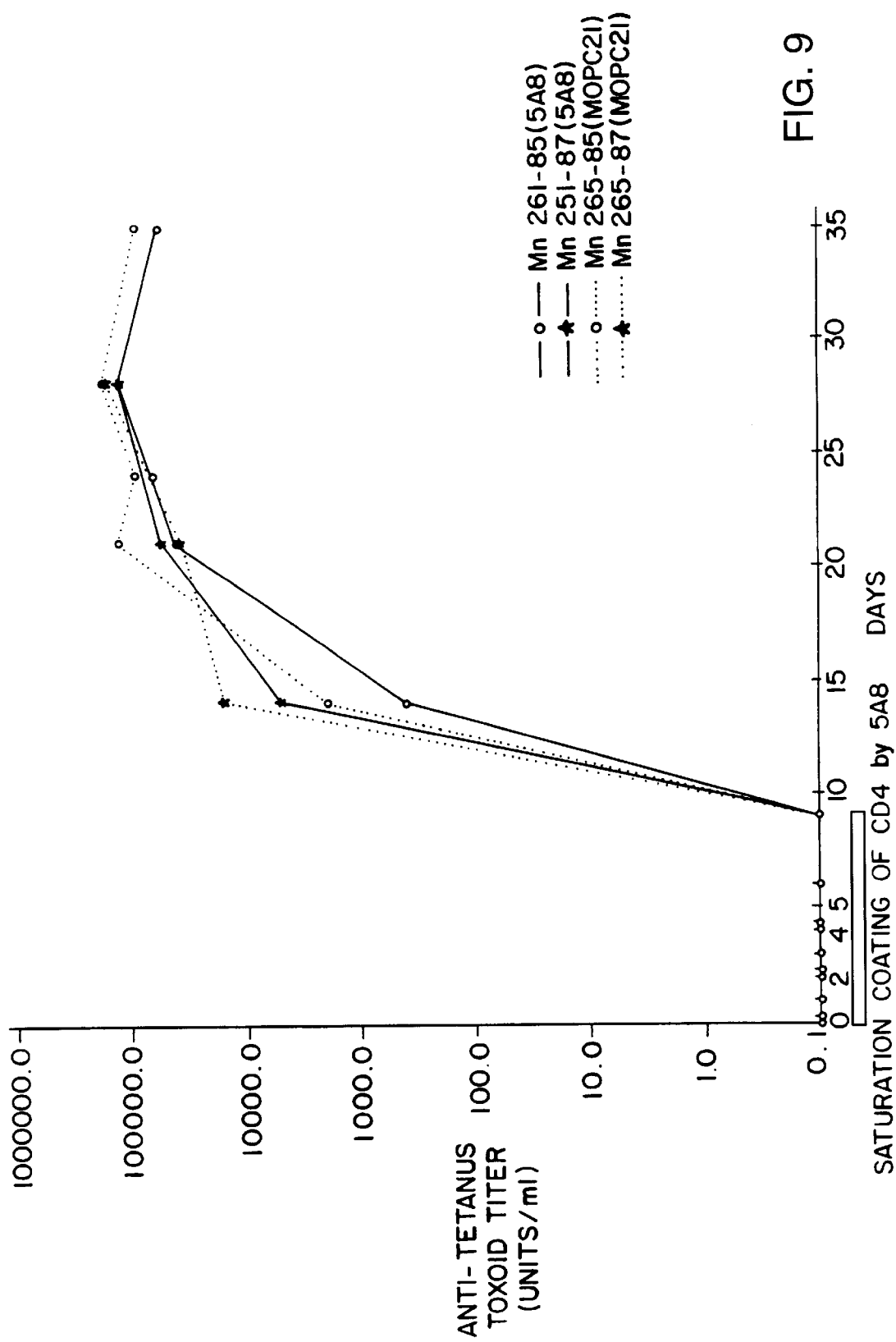
FIG. 9 depicts the anti-tetanus toxoid titers of rhesus monkeys at various time points before, during and after treatment with 5A8 (solid lines, Mn 261-85 and Mn 251-87) or the isotype-matched control monoclonal antibody MOPC21 (dotted lines, Mn 265-85 and Mn 265-87). The y-axis depicts units per milliliter blood of anti-tetanus toxoid antibodies established relative to a standard anti-tetanus toxoid immune serum. The x-axis depicts days, where 5A8 or MOPC21 was injected on days 0, 2 and 4 and tetanus toxoid was injected on days 3 and 21. The bar beneath days 0–9 indicates the time period during which there was saturation coating of CD4 by 5A8 in vivo.

As shown in FIG. 9, we observed anti-tetanus toxoid serum antibody responses in all monkeys with comparable kinetics and titers. Anti-tetanus toxoid titers were measured by ELISA using tetanus toxoid-coated plates, followed by detection with an enzyme-linked goat anti-human/monkey IgM+G. Thus, 5A8 did not affect B cell and helper T cell function.

DNA Encoding 5A8 Heavy Chain Variable Region

Genomic DNA was prepared from the murine hybridoma cell line 5A8 (ATCC accession number HB 10881) substantially as described in J. Sambrook et al., *Molecular Cloning*, ch. 9 (Cold Spring Harbor Laboratory Press 1989). DNA encoding the variable region of the 5A8 immunoglobulin heavy chain (5A8 VH) was isolated from this genomic DNA library as described below.

DNA encoding the 5A8 heavy chain variable region was amplified from the genomic DNA by polymerase chain reaction (PCR) using VH01 (SEQ ID NO:5) and VH02 (SEQ ID NO:6) as primers. These primers are identical to the VH1BACK and VH1FOR primers, respectively, described in Orlandi et al., "Cloning Immunoglobulin Variable Domains For Expression By The Polymerase Chain Reaction", *Proc. Natl. Acad. Sci. USA*, 86, pp. 3833–37 (1989), except that VH02 lacks the two 3' nucleotides of VH1FOR.

VH01 and VH02 (400 pmoles each) were dried down and then resuspended in 50 $\mu$l 1× Kinase Buffer (10× Kinase Buffer is 0.66M Tris-HCl, pH 7.6, 10 mM ATP, 10 mM spermidine, 100 mM $MgCl_2$, 150 mM dithiothreitol, 2 mg/ml gelatin). T4 polynucleotide kinase (1 $\mu$l) (New England Biolabs, 10 U/$\mu$l) was added and the reaction was incubated at 37° C. for 30 minutes, and then at 70° C. for 5 minutes.

The PCR reaction mixture contained 50 pmoles of each kinased primer (VH01 and VH02), 1 $\mu$g genomic 5A8 DNA and 1.25 mM of each dXTP in 1× PCR Buffer (10× PCR Buffer is 100 mM Tris-HCl, pH 8.3, 500 mM KCl, 15 mM $MgCl_2$, 0.01% gelatin). Taq polymerase (0.5 $\mu$l) (Perkin Elmer-Cetus, 5 U/$\mu$l) was added during the 72° C. incubation of the first incubation cycle. The PCR reaction conditions were: 30 cycles of incubation at 94° C. for 2 minutes, 65° C. for 2 minutes, and 72° C. for 2 minutes.

The PCR reaction products were fractionated on a 1% agarose gel by standard methods and the band corresponding to the expected size of immunoglobulin variable region (330 bp) was excised. The DNA in that band was eluted by the GENECLEAN II® technique (Bio101 Inc., LaJolla, Calif.), ethanol precipitated and subsequently resuspended in 10 $\mu$l TE buffer (10 mM Tris-HCl, 1 mM $Na_2EDTA$).

The purified PCR fragment was incubated at room temperature for 20 minutes with the Klenow fragment of DNA polymerase I (1 $\mu$l) (New England Biolabs, 5 U/$\mu$l) and 0.125 mM of each dXTP in 1× Ligation Buffer (10× Ligation Buffer is 0.5M Tris-HCl, pH 7.6, 100 mM $MgCl_2$, 100 mM dithiothreitol, 500 $\mu$g/ml gelatin), at a final reaction volume of 15 $\mu$l. The reaction was terminated by incubation at 65° C. for 5 minutes.

Next, the PCR fragment was ligated into vector pNN03. Vector pNN03 was constructed by removing the synthetic polylinker sequence of pUC8 (Pharmacia, Piscataway, N.J.) by endonuclease cleavage, and replacing it with a novel synthetic polylinker (SEQ ID NO:57). The DNA sequence of pNN03 is set forth as SEQ ID NO:7. Vector pNN03 was prepared for ligation by linearizing with EcoR5, dephosphorylating the 5' ends with calf alkaline phosphatase, fractionating on a low melting temperature agarose gel, and excising the band corresponding to linearized pNN03 (2.7 kb). The linearized, dephosphorylated pNN03 was then ligated to the Klenow-treated PCR 5A8 VH fragment using T4 DNA ligase.

The ligation mixture was used to transform *E. coli* JA221 (ATCC 33875) to ampicillin resistance. Colonies were grown up and mini-prep DNA was prepared. The recombinant plasmids were screened for the presence of an approximately 450 bp Sac2 insert. In addition, the amino acid sequence encoded by the PCR fragment was compared to the experimentally determined amino terminal amino acid sequence of the 5A8 heavy chain. By these means, the insert of vector pMDR904 was confirmed to contain a DNA sequence encoding $AA_2$–$AA_{122}$ of the 5A8 heavy chain variable region. *E. coli* harboring pMDR904 have been deposited with the American Type Culture Collection, Rockville, Md., under accession number ATCC 68848.

SEQ ID NO:8 sets forth the DNA sequence of the pMDR904 insert. Nucleotides 3 to 365 of SEQ ID NO:8 encode $AA_2$–$AA_{22}$ of the 5A8 $V_H$ sequence. Vector pMDR904 does not contain the codon for $AA_1$ of 5A8 $V_H$. This codon is "built back" using an oligonucleotide when a 5A8 $V_H$ expression vector is made.

Although pMDR904 is missing the codon for $AA_1$ of 5A8 $V_H$, we know the identity of that amino acid from amino acid sequence results. The complete amino acid sequence of 5A8 $V_H$ ($AA_1$–$AA_{122}$) is set forth as SEQ ID NO:10. A DNA sequence (hypothetical as to $AA_1$) encoding the 5A8 $V_H$ amino acid sequence is set forth as SEQ ID NO:9.

By comparison to known complementarity determining region (CDR) and framework (FR) sequences, we identified the following as the CDRs of the 5A8 heavy chain: CDR1 is $AA_{31}$–$AA_{35}$, CDR2 is $AA_{50}$–$AA_{66}$, CDR3 is $AA_{99}$–$AA_{111}$, all with respect to SEQ ID NO:10.

DNA Encoding 5A8 Light Chain Variable Region

Total RNA was prepared from the murine hybridoma cell line 5A8 (ATCC accession number HB 1088) according to a conventional guanidinium isothiocyanate protocol. Poly (A)+RNA was prepared from the total RNA using an oligo-d(T) column (Clontech), also according to conventional procedures.

cDNA was prepared from the poly(A)$^+$ RNA as follows. Oligonucleotides ACE149 (SEQ ID NO:11) and ACE150 (SEQ ID NO:12) (200 pmoles each) were incubated separately with 1 $\mu$l T4 polynucleotide kinase (New England Biolabs, 10 U/$\mu$l) in 100 $\mu$l of 1× Kinase Buffer. 5A8 poly(A)$^+$ RNA (25 $\mu$g) was dried down, and then incubated 10 minutes at room temperature with a mixture of: 5 $\mu$l of each kinased oligonucleotide, 2 $\mu$l 25 mM methylmercury hydroxide and 10 $\mu$l water. After that 10 minute incubation, 2 $\mu$l 50 mM dithiothreitol was added, and the mixture was incubated an additional 5 minutes at room temperature. Next, the following were added: 10 $\mu$l M-MLV reverse transcriptase (BRL 80255B, 200 U/$\mu$l), 20 $\mu$l 2.5 mM dXTPs, 26 $\mu$l water and 20 $\mu$l 5× Reverse Transcriptase Buffer (250 mM Tris-HCl, pH 8.3, 375 mM KCl, 50 mM dithiothreitol, 15 mM $MgCl_2$). After incubating at 37° C. for 1 hour, the reverse transcriptase reaction was terminated by freezing.

DNA encoding the 5A8 light chain variable region was amplified from the 5A8 cDNA by PCR using ACE149 (SEQ ID NO:11) and ACE150 (SEQ ID NO:12) as primers. The PCR reaction mixture contained 50 pmoles of each kinased primer, 5 $\mu$l 5A8 cDNA, 8 $\mu$l 2.5 mM dXTPs, 0.5 $\mu$l Taq polymerase (5 U/$\mu$l) and 10 $\mu$l 10× PCR Buffer. The PCR reaction conditions were: 30 cycles of incubation at 94° C. for 1 minute, 37° C. for 1 minute, and 72° C. for 2 minutes.

The completed PCR reaction mixture was extracted once with ether, once with phenol:chloroform (1:1) saturated with TE buffer, and then ethanol precipitated. The ethanol precipitate was resuspended in 100 $\mu$l of buffer containing 0.5 mM dXTPs, 100 mM NaCl, 10 mM Tris-HCl, pH 8.0, 1 mM $Na_2EDTA$, 100 $\mu$g/ml gelatin and 10 mM dithiothreitol. Klenow fragment of DNA polymerase I (1 $\mu$l, 5 U/$\mu$l) was added and the mixture was incubated at room temperature for 10 minutes. The reaction mixture was fractionated on a 2% agarose gel by standard methods and the band corresponding to the expected size of immunoglobulin variable region (350 bp) was excised. The DNA in that band was eluted by the GENECLEAN II® technique.

Next, the PCR fragment was ligated into vector pUC19 (New England Biolabs). Vector pUC19 was prepared for ligation by linearizing with Sma1, dephosphorylating the 5' ends with calf alkaline phosphatase, fractionating on a low melting temperature agarose gel, and excising the band corresponding to linearized pUC19 (2.7 kb). The linearized, dephosphorylated pUC19 was then ligated to the Klenow-treated PCR 5A8 $V_L$ fragment using T4 DNA ligase.

The ligation mixture was used to transform *E. coli* JA221 to ampicillin resistance. Colonies were grown up and mini-prep DNA was prepared. The recombinant plasmids were screened for the presence of an approximately 400 bp EcoRI/Hind3 fragment. In addition, the amino acid sequence encoded by the PCR fragment was compared to the experimentally determined amino terminal amino acid sequence of the 5A8 light chain. By these means, the insert of vector pMDR927 was confirmed to contain a DNA sequence encoding $AA_1$–$AA_{111}$ of the 5A8 light chain variable region. *E. coli* harboring pMDR927 have been deposited with the American Type Culture Collection, Rockville, Md., under accession number ATCC 68849.

SEQ ID NO:13 sets forth the DNA sequence of the pMDR927 insert. Nucleotides 4 to 336 of SEQ ID NO:13 encode $AA_1$–$AA_{111}$ of the 5A8 $V_L$ sequence. Vector pMDR927 does not contain the codon for $AA_{112}$ of 5A8 $V_L$. That codon is "built back" using an oligonucleotide when a 5A8 $V_L$ expression vector is made.

Although pMDR927 is missing the codon for $AA_{112}$ of the 5A8 $V_L$, we know the identity of that amino acid from amino acid sequence results. The complete amino acid sequence of 5A8 $V_L$ is set forth as SEQ ID NO:15. A DNA sequence (hypothetical as to $AA_{112}$) encoding the 5A8 $V_L$ amino acid sequence is set forth as SEQ ID NO:14.

By comparison to known CDR and FR sequences, we identified the following as the CDRs of the 5A8 light chain: CDR1 is $AA_{24}$–$AA_{40}$, CDR2 is $AA_{56}$–$AA_{62}$, CDR3 is $AA_{95}$–$AA_{102}$, all with respect to SEQ ID NO:15.

Humanizing 5A8 Heavy And Light Chains

The amino acid sequences of the 5A8 $V_H$ and $V_L$ regions were compared to the known human immunoglobulin sequences to find the human framework sequences most closely matching the murine 5A8 framework sequences. Humanized versions of the 5A8 heavy and light chain variable regions then were designed by grafting the CDRs of the 5A8 $V_H$ and $V_L$ onto the human frameworks. These humanized variable regions were then ligated to DNA encoding human $IgG_4$ heavy chain and kappa light chain constant regions, respectively, and inserted into eukaryotic expression vectors.

1. Humanizing 5A8 Heavy Chain Variable Region

The 5A8 heavy chain variable region was humanized by PCR mutagenesis. Three PCR reactions were carried out using three different pairs of oligonucleotide PCR primers: (a) primers 312-56 (SEQ ID NO:16) and 312-57 (SEQ ID NO:17); (b) primers 312-58 (SEQ ID NO:18) and 312-59 (SEQ ID NO:19); and (c) primers 312-60 (SEQ ID NO:20) and 312-61 (SEQ ID NO:21). Each PCR reaction contained 30 pmoles of each of the appropriate primers, 1 μg pMDR904 (insert sequence is SEQ ID NO:8), 16 μl 1.25 mM dXTPs, 0.5 μl Taq polymerase (5 U/μl) and 10 μl 10× PCR Buffer. The incubation conditions for PCR were 10 cycles of incubation for 3 minutes at 94° C., 2 minutes at 45° C. and 2 minutes at 72° C. The PCR products were fractionated through a 2% agarose gel, and the bands corresponding to approximately 160 bp, 175 bp and 165 bp were excised. The three PCR fragments were eluted separately using GENECLEAN II®, into 100 μl aliquots of TE buffer.

The three eluted PCR fragments (10 μl each) were combined and subjected to a second round of PCR using oligonucleotide primers 312-56 (SEQ ID NO:16) and 312-61 (SEQ ID NO:21) for 20 cycles of incubation for 3 minutes at 94° C., 2 minutes at 72° C. and 2 minutes at 72° C., with the same reaction conditions used in the first round of PCR. The PCR products were fractionated through a 2% agarose gel, and the band corresponding to approximately 365 bp was excised. The PCR fragment was eluted using GENECLEAN II® and the eluate was ethanol precipitated. The ethanol precipitate was resuspended in 20 μl TE buffer, and treated with the Klenow fragment of DNA polymerase I as described above.

Next, the PCR fragment was ligated into vector pNN03 (SEQ ID NO:7). Vector pNN03 was prepared for ligation by linearizing with EcoR5, dephosphorylating the 5' ends with calf alkaline phosphatase, fractionating on a low melting temperature agarose gel, and excising the band corresponding to linearized pNN03 (2.7 kb). The linearized, dephosphorylated pNN03 was then ligated to the Klenow-treated PCR 5A8 humanized $V_H$ fragment using T4 DNA ligase.

The ligation mixture was used to transform *E. coli* JA221 (Iq) to ampicillin resistance. *E. coli* JA221(Iq) cells were deposited with the American Type Culture Collection, Rockville, Md., and have been assigned accession number ATCC 68845. Colonies were grown up and mini-prep DNA was prepared. The recombinant plasmids were screened for the presence of an approximately 400 bp Sac2 fragment. DNA sequence analysis revealed that none of the plasmids had the correct sequence, but one plasmid—pMDR989-15 (insert sequence is SEQ ID NO:22)—had approximately 50% of the mutations necessary to convert the murine 5A8 $V_H$ sequence to the designed humanized sequence. Therefore, pMDR989-15 was subjected to a second two rounds of PCR as described immediately above. Thereafter, the insert of vector pMDR991 was identified by DNA sequence analysis to have the designed 5A8 $V_H$ humanized sequence.

SEQ ID NO:23 sets forth the DNA sequence of the pMDR991 insert. Nucleotides 1 to 357 of SEQ ID NO:23 encode $AA_2$–$AA_{120}$ of the humanized 5A8 $V_H$ sequence. Vector pMDR991 does not contain codons for $AA_1$ and $AA_{121}$–$AA_{122}$ of humanized 5A8 $V_H$. As described below, these codons were "built back" using oligonucleotides when the humanized 5A8 $V_H$ eukaryotic expression vector was made.

2. Humanizing 5A8 Light Chain Variable Region

The humanized 5A8 light chain variable region was prepared by ligating 10 oligonucleotides, which together span the entire humanized 5A8 $V_L$ region, and screening for constructs having the correct sequence. The protocol is described in more detail below.

Oligonucleotides 312-62 through 312-71 (SEQ ID NO:24 through SEQ ID NO:33, respectively) (20 pmoles each) were dried down, and separately resuspended in 20 μl 1× Kinase Buffer containing 1 mM ATP and 1 μl T4 polynucleotide kinase (10 U/μl). The kinase reaction mixture was incubated for 1 hour at 37° C. The reaction was terminated by incubating at 70° C. for 5 minutes.

The kinase-treated oligonucleotides (0.4 μg each) were combined with each other and with 25 μl 10 mM ATP and 2 μl T4 DNA ligase (10 U/μl), and the reaction mixture was incubated at room temperature for 6 hours. The ligation reaction mixture was extracted with phenol:chloroform (1:1) saturated with TE buffer, and then ethanol precipitated.

The ethanol precipitate was resuspended in 50 µl 1× 150 mM Restriction Enzyme Buffer (10× 150 mM Restriction Enzyme Buffer is 100 mM Tris-HCl, pH 8.0, 1.5M NaCl, 100 mM MgCl$_2$, 1 mg/ml gelatin, 10 mM dithiothreitol) and incubated with restriction enzymes Bgl2 and Asp718 for 16 hours at 37° C. The digestion products were electrophoresed through a 2% agarose gel, and the band corresponding to 330 bp was excised. The fragment was eluted using GENECLEAN II® and the eluate was ethanol precipitated. The ethanol precipitate was resuspended in 20 µl TE buffer.

Next, the 330 bp fragment was ligated into vector pNN03 (SEQ ID NO:7). Vector pNN03 was prepared for ligation by linearizing with Asp718 and Bgl2, dephosphorylating the 5' ends with calf alkaline phosphatase, fractionating on a low melting temperature agarose gel, and excising the band corresponding to linearized pNN03 (2.7 kb). The linearized, dephosphorylated pNN03 was then ligated to the 330 bp oligonucleotide fragment encoding the humanized $V_L$ region using T4 DNA ligase.

The ligation mixture was used to transform E. coli JA221 (Iq) to ampicillin resistance. Colonies were grown up and mini-prep DNA was prepared. The recombinant plasmids were screened for the presence of an approximately 400 bp Sac2 fragment. DNA sequence analysis identified vector pMDR1003 as having the designed humanized sequence for the 5A8 kappa light chain variable region.

SEQ ID NO:34 sets forth the DNA sequence of the pMDR1003 insert. Nucleotides 11 to 343 of SEQ ID NO:34 encode $AA_1$–$AA_{111}$ of the humanized 5A8 $V_L$ sequence. Vector pMDR1003 does not contain the codon for $AA_{112}$ of humanized 5A8 $V_L$. As described below, that codon was "built back" using an oligonucleotide when the humanized 5A8 $V_L$ eukaryotic expression vector was made.

3. 5A8 Humanized Heavy Chain Expression Vector

A eukaryotic expression vector carrying 5A8 humanized heavy chain (pMDR1002) was constructed by ligating intermediate plasmids pMDR1001, pBAG101 and pSAB132, as described below.

A. Intermediate Plasmid DMDR1001

Intermediate plasmid pMDR1001 was constructed to carry DNA encoding the human HG3 immunoglobulin heavy chain signal sequence (see Kabat, Sequence of Proteins of Immunological Interest, p. 460 (4th ed.), $AA_1$–$AA_{122}$ of the humanized 5A8 heavy chain variable region, followed by an RNA 5' splice site. Plasmid pMDR1001 was constructed from pLCB7 and pMDR991. Plasmid pLCB7, in turn, was constructed from pLCB6 and pMDR904.

Plasmid pLCB6 was designed to carry DNA encoding the human immunoglobulin heavy chain signal sequence, an RNA 5' splice site and restriction sites for Pst1 and BstE2. To make pLCB6, oligonucleotides 312-45 (SEQ ID NO:35), and 312-50 (SEQ ID NO:36) and 312-46 through 312-49 (SEQ ID NO:58 through SEQ ID NO:61, respectively) were treated with polynucleotide kinase and ligated together as described above. Next, the ligated oligonucleotide was itself ligated into a 2701 bp Asn718/BamH1 fragment of plasmid pNN03, giving pLCB6. The DNA sequence of the pLCB6 insert is SEQ ID NO:37.

Plasmid pLCB6 was cleaved with Pst1 and BstE2, and a 2820 bp fragment was isolated. That fragment was ligated to the 346 bp Pst1/BstE2 fragment of pMDR904. Plasmid pLCB7 was identified by the presence of a 397 bp StyI restriction fragment. The DNA sequence of the pLCB7 insert is SEQ ID NO:38.

Plasmids pLCB7 and pMDR991 were individually cleaved with Pst1 and BstE2, and 2820 bp (vector) and 337 bp (insert) fragments, respectively, were isolated following separate fractionation through low temperature melting agarose. These fragments were then ligated together. Plasmid pMDR1001 was identified by the presence of a diagnostic Hae2 restriction pattern (1871 bp, 523 bp, 393 bp and 370 bp). The DNA sequence of the pMDR1001 insert is SEQ ID NO:39.

Plasmid pMDR1001 was cleaved with Not1 and Hind3 and the 443 bp fragment containing the plasmid insert was isolated by fractionation through low temperature melting agarose.

B. Intermediate Plasmid PSAB132

Intermediate plasmid pSAB132 was constructed to be a general purpose eukaryotic expression shuttle vector. It carries the human cytomegalovirus immediate early promoter and enhancer. The construction of pSAB132 is described at pages 55–56 of commonly assigned U.S. patent application Ser. No. 07/770,967. The entire sequence of pSAB132 is set forth as SEQ ID NO:40.

Vector pSAB132 was linearized with Not1. The 7913 bp linearized vector then was dephosphorylated and isolated by fractionation through low temperature melting agarose.

C. Intermediate Plasmid pBAG101

Intermediate plasmid pBAG101 was constructed to carry genomic DNA encoding the human $IgG_4$ heavy chain constant region.

Genomic DNA was prepared from human placenta substantially as described in J. Sambrook et al., Molecular Cloning, ch. 9 (Cold Spring Harbor Laboratory Press 1989). DNA encoding the $IgG_4$ constant region was amplified as described above from the genomic DNA by PCR using oligonucleotides 370-38 (SEQ ID NO:41) and 370-40 (SEQ ID NO:42) as primers.

The approximately 2109 bp PCR fragment was isolated by gel electrophoresis and ligated into EcoR5 linearized pNN03. Plasmid pBAG101 was identified by the presence of 3887 bp and 3896 bp Bgl2 restriction fragments. The DNA sequence of the pBAG101 insert is SEQ ID NO:43. The DNA sequence encoding the human $IgG_4$ heavy chain constant region in the pBAG101 insert was obtained from the corresponding sequence of Genbank Accession Number K01316-PR:HUMIGCD2.

Plasmid pBAG101 was cleaved with Not1 and Hind3 and the 2109 bp fragment containing the plasmid insert was isolated by fractionation through low temperature melting agarose.

D. Final Construction Of Vector PMDR1002

Three fragments were ligated together to generate pMDR1002: (a) 443 bp Not1/Hind3 fragment of pMDR1001; (b) 7913 bp Not1 linearized pSAB132; and (c) 2109 bp Not1/Hind3 fragment of pBAG101. The ligation mixture was used to transform E. coli JA221(Iq) to ampicillin resistance. Colonies were grown up and mini-prep DNA was prepared. The recombinant plasmids were screened for the presence of approximately 1276 bp and 9160 bp EcoR1 fragments, identifying pMDR1002.

The DNA sequence of pMDR1002's insert is set forth as SEQ ID NO:44. The amino acid sequence encoded by that DNA sequence is set out as SEQ ID NO:45. The pMDR1002 insert comprises DNA encoding, in 5' to 3' order, (1) the immunoglobulin signal sequence (nucleotides 12–68 of SEQ ID NO:44, corresponding to $AA_{-19}$–$AA_{-1}$ of SEQ ID NO:45), (2) $AA_1$–$AA_{122}$ of the designed humanized sequence for the 5A8 heavy chain variable region (nucleotides 69–434 of SEQ ID NO:44, corresponding to $AA_1$–$AA_{122}$ of SEQ ID NO:45), followed by genomic DNA (nucleotides 27 to 2525 of Genbank accession number K01316) encoding $AA_{114-AA478}$ (Kabat numbering) of the human $IgG_4$ heavy chain (i.e., the heavy chain constant region) (nucleotides 712–1005, 1396–1431, 1550–1879, and 1977–2296 of SEQ ID NO:44, corresponding to $AA_{123}$–$AA_{448}$ of SEQ ID NO:45).

E. coli harboring pMDR1002 have been deposited with the American Type Culture Collection, Rockville, Md., under accession number ATCC 68847.

4. 5A8 Humanized Light Chain Expression Vector

A eukaryotic expression vector carrying 5A8 humanized light chain (pMDR1007) was constructed by ligating intermediate plasmids pMDR1006 and pSAB132. Plasmid PMDR1006 was in turn constructed by ligating intermediate plasmids pMDR985, PMDR986 and pMDR1003. The specific construction strategy is discussed below.

A. Intermediate Plasmid PMDR985

Intermediate plasmid PMDR985 was constructed to carry DNA encoding a prototypical human immunoglobulin kappa light chain signal sequence.

To make plasmid pMDR985, oligonucleotides 360-81 (SEQ ID NO:46) and 360-82 (SEQ ID NO:47) were treated with polynucleotide kinase and ligated together as described above. Next, the ligated oligonucleotide was itself ligated into a 2707 bp Hind3/EcoR5 fragment of plasmid pNN03 that had been dephosphorylated by calf alkaline phosphatase. The ligation mixture was used to transform E. coli JA221(Iq) to ampicillin resistance. Colonies were grown up and mini-prep DNA was prepared. The recombinant plasmids were screened for the presence of approximately 461 bp and 2321 bp EcoO109 I fragments, identifying pMDR985.

The DNA sequence of pMDR985's insert is set forth as SEQ ID NO:48. DNA sequence analysis confirmed pMDR985 to have the correct codons for the signal sequence (nucleotides 9 to 77 of SEQ ID NO:48); however, due to a cloning artifact the designed Hind3 site (5' of the insert) was not reconstituted in pMDR985.

Plasmid pMDR985 was cleave d with Aat2 and EcoR5 and the 572 bp fragment containing the plasmid insert was isolated by fractionation through low temperature melting agarose.

B. Intermediate Plasmid DMDR986

Intermediate plasmid pMDR986 was constructed to carry genomic DNA encoding $AA_{108}$–$AA_{214}$ (Kabat numbering) of a human kappa light chain (i.e., the light chain constant region).

Genomic DNA was prepared from human placenta (substantially as described in J. Sambrook et al., *Molecular Cloning*, ch. 9 (Cold Spring Harbor Laboratory Press 1989). The genomic DNA was cleaved with EcoRI and a 2.5 kb EcoR1 fragment comprising the kappa chain constant region (Genbank Accession Number J00241 -PR:HUMIGKC3) was cloned into the EcoR1 site of pUC8, generating pAB8.

DNA encoding the kappa constant region ($AA_{108}$–$AA_{214}$) was amplified as described above from pAB8 by PCR using oligonucleotides 370-54 (SEQ ID NO:49) and 370-55 (SEQ ID NO:50) as primers. The approximately 1240 bp PCR fragment was isolated and ligated into EcoR5 linearized pNN03 that had been dephosphorylated. Plasmid pSAB153 was identified by the presence of a 1314 bp Xmn1 restriction fragment. The DNA sequence of the pSAB153 insert is SEQ ID NO:51.

Plasmid pMDR986 was constructed from pSAB153 as follows. The kappa constant region was amplified from pSAB153 by PCR using oligonucleotides 360-83 (SEQ ID NO:52) and 370-55 (SEQ ID NO:50) as primers. The approximately 1276 bp PCR fragment was isolated by GENECLEAN II® elution, followed by electrophoresis through agarose, ethanol precipitation and resuspension in 20 µl TE buffer. The purified PCR fragment was treated with the Klenow fragment of DNA polymerase I and ligated to EcoR5 linearized pNN03 that had been dephosphorylated by calf alkaline phosphatase.

The ligation mixture was used to transform E. coli JA221 (Iq) cells. DNA was prepared from ampicillin resistant colonies and screened by EcoO109 I restriction digestion. Plasmid pMDR986 was identified by the presence of a 1122 bp EcoO109 I restriction fragment. The pMDR986 plasmid then was used to transform E. coli GM2929, which does not methylate its DNA (a dam-13, dcm-6 strain).

The DNA sequence of the pMDR986 insert is SEQ ID NO:53. DNA sequence analysis confirmed pMDR986 to have the correct exons to encode $AA_{108}$–$AA_{214}$ of the human kappa chain. However, due to a cloning artifact the designed Not1 site 3' of the constant region was not reconstituted in pMDR986 and a Pvu1 site was created instead.

Plasmid pMDR986 was cleaved with Aat2 and Bcl1 , treated with calf alkaline phosphatase, and the 3443 bp fragment was isolated by fractionation through low temperature melting agarose.

C. Intermediate Plasmid DMDR1003

The construction of plasmid PMDR1003 is described above. It carries DNA encoding humanized 5A8 kappa light chain variable region. The DNA sequence of the PMDR1003 insert is set forth as SEQ ID NO:34.

Plasmid pMDR1003 was cleaved with EcoR5 and Bgl2 and the 326 bp fragment containing the plasmid insert was isolated by fractionation through low temperature melting agarose.

D. Final Construction Of Vector MDR1007

Vector pMDR1007 was constructed from PSAB132 (SEQ ID NO:40) and PMDR1006 (insert DNA sequence is SEQ ID NO:54).

Three fragments were ligated together to generate pMDR1006: (a) 572 bp Aat2/EcoR5 fragment of pMDR985; (b) 3442 bp Aat2/Bcl1 fragment of pMDR986; and (c) 326 bp LcoR5/12 fragment of pMDR1003. The ligation mixture was used to transform E. coli JA221(Iq) [source?] to ampicillin resistance. Colonies were grown up and mini-prep DNA was prepared. The recombinant plasmids were screened for the presence of diagnostic EcoO109 I restriction fragments (2741 bp, 767 bp and 461 bp, 243 bp and 129 bp), identifying pMDR1006. The DNA sequence of pMDR1006's insert is set forth as SEQ ID NO:54.

Plasmid pMDR1006 was cleaved with Not1 and the 1693 bp fragment was isolated. The Not1 fragment was ligated into Not1 linearized pSAB132 (SEQ ID NO:40) that had previously been dephosphorylated by calf alkaline phosphatase. The dephosphorylated reaction mixture was fractionated through low temperature melting agarose, and then used to transform E. coli JA221(Iq) to ampicillin resistance. Colonies were grown up and mini-prep DNA was prepared. The recombinant plasmids were screened for a diagnostic ApaL1 digestion pattern (fragments of 6249 bp, 1593 bp, 1246 bp, and 498 bp), identifying pMDR1007.

The DNA sequence of pMDR1007's insert is set forth as SEQ ID NO:55. The amino acid sequence encoded by that DNA sequence is set out as SEQ ID NO:56. The pMDR1007 insert comprises DNA encoding, in 5' to 3' order, (1) the immunoglobulin kappa chain signal sequence (nucleotides 35-100 of SEQ ID NO:55, corresponding to $AA_{-22}$–$AA_{-1}$ of SEQ ID NO:56), (2) $AA_1$–$AA_{112}$ of the designed humanized sequence for the 5A8 light chain variable region (nucleotides 101-436 of SEQ ID NO:55, corresponding to $AA_1$–$AA_{112}$ of SEQ ID NO:56), followed by genomic DNA (nucleotides 1 to 1201 of Genbank Accession Number J00241-PR:HUMIGKC3) encoding $AA_{108}$–$AA_{214}$ (Kabat numbering) of the human kappa light chain (i.e., the light chain constant region) (nucleotides 437 and 782-1101 of SEQ ID NO:55, corresponding to $AA_{113}$–$AA_{219}$ of SEQ ID NO:56).

E. coli harboring pMDR1007 have been deposited with the American Type Culture Collection, Rockville, Md., under accession number ATCC 68846.

5. Expression Of Humanized 5A8

In a preliminary experiment, COS7 cells were transfected with expression vectors pMDR1007 and pMDR1002 by electroporation and the cells were cultured for 48 hours. The cells were then radiolabelled with $^{35}$S-methionine. Then, cell extracts and conditioned culture media were incubated with Protein A-Sepharose. The Protein A-Sepharose was washed and the bound proteins were eluted with SDS polyacrylamide gel electrophoresis (PAGE) loading buffer, and analyzed by PAGE. Assembled immunoglobulin molecules were detected in the conditioned media at very low yields, as evidenced by Protein A precipitation of immunoglobulin light chain.

Deposits

Cells and antibody homologs according to the present invention are exemplified by cultures deposited under the Budapest Treaty in the In-Vitro International, Inc. culture collection in Linthicum, Maryland, U.S.A. on Nov. 20, 1990, and identified as:

"5A8-2F6"
"7-27-1F8-2B4"
"7-27-5F2-2C5"
"CHO 379 clone 12.1"
"CHO-160"

These cultures were assigned accession numbers IVI-10257 to IVI-10261, respectively. These deposits were transferred on Jun. 20, 1991 to the American Type Culture Collection, Rockville, Md., and are being maintained by the American Type Culture Collection under the Budapest Treaty under accession numbers HB 10881, HB 10882, HB 10883, CRL 10884 and CRL 10885, respectively.

DNA sequences and recombinant DNA molecules according to the present invention, and a microorganism useful in preparing same, are exemplified by cultures deposited under the Budapest Treaty with the American Type Culture Collection, Rockville, Md., U.S.A. on Nov. 21, 1991, and identified as:

"E. coli K12 JA221(Iq)"
"E. coli K12 JA221(Iq)/pMDR1007"
"E. coli K12 JA221(Iq)/pMDR1002"
"E. coli K12 JA221(Iq)/pMDR904"
"E. coli K12 JA221(Iq)/pMDR927"

These cultures were assigned accession numbers ATCC 68845 to ATCC 68849, respectively.

Sequences

The following is a summary of the sequences set forth in the sequence library:

SEQ ID NO:1 DNA sequence of pre-HIV gp160
SEQ ID NO:2 Amino acid sequence of pre-HIV gp160
SEQ ID NO:3 DNA sequence of soluble HIV gp120
SEQ ID NO:4 Amino acid sequence of soluble HIV gp120
SEQ ID NO:5 DNA sequence of VH01 PCR primer
SEQ ID NO:6 DNA sequence of VH02 PCR primer
SEQ ID NO:7 DNA sequence of pNN03
SEQ ID NO:8 DNA sequence of pMDR904 insert (5A8 $V_H$)
SEQ ID NO:9 DNA sequence of 5A8 heavy chain variable region
SEQ ID NO:10 Amino acid sequence of 5A8 heavy chain variable region
SEQ ID NO:11 DNA sequence of ACE149 PCR primer
SEQ ID NO:12 DNA sequence of ACE150 PCR primer
SEQ ID NO:13 DNA sequence of pMDR927 insert (5A8 $V_L$)
SEQ ID NO:14 DNA sequence of 5A8 light chain variable region
SEQ ID NO:15 Amino acid sequence of 5A8 light chain variable region
SEQ ID NO:16 DNA sequence of 312-56 PCR primer
SEQ ID NO:17 DNA sequence of 312-57 PCR primer
SEQ ID NO:18 DNA sequence of 312-58 PCR primer
SEQ ID NO:19 DNA sequence of 312-59 PCR primer
SEQ ID NO:20 DNA sequence of 312-60 PCR primer
SEQ ID NO:21 DNA sequence of 312-61 PCR primer
SEQ ID NO:22 DNA sequence of pMDR989-15 insert
SEQ ID NO:23 DNA sequence of pMDR991 insert
SEQ ID NO:24 DNA sequence of 312-62 oligonucleotide
SEQ ID NO:25 DNA sequence of 312-63 oligonucleotide
SEQ ID NO:26 DNA sequence of 312-64 oligonucleotide
SEQ ID NO:27 DNA sequence of 312-65 oligonucleotide
SEQ ID NO:28 DNA sequence of 312-66 oligonucleotide
SEQ ID NO:29 DNA sequence of 312-67 oligonucleotide
SEQ ID NO:30 DNA sequence of 312-68 oligonucleotide
SEQ ID NO:31 DNA sequence of 312-69 oligonucleotide
SEQ ID NO:32 DNA sequence of 312-70 oligonucleotide
SEQ ID NO:33 DNA sequence of 312-71 oligonucleotide
SEQ ID NO:34 DNA sequence of pMDR1003 insert
SEQ ID NO:35 DNA sequence of 312-45 oligonucleotide
SEQ ID NO:36 DNA sequence of 312-50 oligonucleotide
SEQ ID NO:37 DNA sequence of pLCB6 insert
SEQ ID NO:38 DNA sequence of pLCB7 insert
SEQ ID NO:39 DNA sequence of pMDR1001 insert
SEQ ID NO:40 DNA sequence of pSAB132
SEQ ID NO:41 DNA sequence of 370-38 PCR primer
SEQ ID NO:42 DNA sequence of 370-40 PCR primer
SEQ ID NO:43 DNA sequence of pBAG101 insert
SEQ ID NO:44 DNA sequence of pMDR1002 insert (pre-5A8 humanized heavy chain)
SEQ ID NO:45 Amino acid sequence of pMDR1002 insert (pre-5A8 humanized heavy chain)
SEQ ID NO:46 DNA sequence of 360-81 oligonucleotide
SEQ ID NO:47 DNA sequence of 360-82 oligonucleotide
SEQ ID NO:48 DNA sequence of pMDR985 insert
SEQ ID NO:49 DNA sequence of 370-54 PCR primer
SEQ ID NO:50 DNA sequence of 370-55 PCR primer
SEQ ID NO:51 DNA sequence of pSAB1.53 insert
SEQ ID NO:52 DNA sequence of 360-83 PCR primer
SEQ ID NO:53 DNA sequence of pMDR986 insert
SEQ ID NO:54 DNA sequence of pMDR1006 insert
SEQ ID NO:55 DNA sequence of pMDR1007 insert (pre-5A8 humanized light chain)
SEQ ID NO:56 Amino acid sequence of pMDR1007 insert (pre-5A8 humanized light chain)
SEQ ID NO:57 DNA sequence of pNN03 synthetic polylinker
SEQ ID NO:58 DNA sequence of 312-46 oligonucleotide
SEQ ID NO:59 DNA sequence of 312-47 oligonucleotide
SEQ ID NO:60 DNA sequence of 312-48 oligonucleotide
SEQ ID NO:61 DNA sequence of 312-49 oligonucleotide.

While we have hereinbefore described a number of embodiments of this invention, it is apparent that our basic embodiments can be altered to provide other embodiments that utilize the compositions and processes of this invention.

Therefore, it will be appreciated that the scope of this invention includes all alternative embodiments and variations which are defined in the foregoing specification and by the claims appended hereto; and the invention is not to be limited by the specific embodiments that have been presented herein by way of example. These deposits have been made under conditions that assure that if the cultures should die or be destroyed during the term of the deposit, the cultures shall be replaced and that access thereto will be available during pendency of this application to those determined by the Commissioner to be eligible thereto and that all restrictions imposed by the deposits on the availability to the public of the material will be irrevocably removed upon granting of the patent.

We claim:

1. An antibody homolog that
   (a) binds to human CD4;
   (b) does not significantly block binding of HIV gp 120 to human CD4;
   (c) blocks HIV-induced syncytia formation between CD4+ cells at least as well as OKT4A.

2. An antibody homolog according to claim 1, wherein the antibody homolog does not bind to a polypeptide consisting of human CD4 V1.

3. An antibody homolog according to claim 1, wherein the antibody homolog does not significantly block the binding of CD4 V1-specific antibodies to human CD4.

4. An antibody homolog according to claim 1, wherein the antibody homolog inhibits infection of CD4+ cells by HIV.

5. An antibody homolog according to claim 1, wherein the antibody homolog displays one or more characteristics selected from:
   (a) causing no significant decrease in the number of circulation CD4+ cells in vivo;
   (b) causing no significant modulation of CD4 from the surface of CD4+ cells in vivo;
   (c) causing no significant decrease in circulating peripheral white blood cell counts in vivo; and
   (d) causing no significant decrease in antibody titer elicited in response to foreign antigens in vivo.

6. An antibody homolog according to claim 1, which is a humanized recombinant antibody homolog.

7. An humanized recombinant antibody homolog according to claim 6, wherein the amino acid sequences of the CDRs are as follows:
   (a) light chain CDR1 is AA24–AA40 of SEQ ID NO: 15;
   (b) light chain CDR2 is AA56–AA62 of SEQ ID NO: 15;
   (c) light chain CDR3 is AA95–AA102 of SEQ ID NO: 15;
   (d) heavy chain CDR1 is AA31–AA35 of SEQ ID NO: 10;
   (e) heavy chain CDR2 is AA50–AA66 of SEQ ID NO: 10; and
   (f) heavy chain CDR3 is AA99–AA111 of SEQ ID NO: 10.

8. An antibody homolog according to claim 1, which is a chimeric recombinant antibody homolog, having a light chain or having a heavy chain or having both chains derived from a first mammalian species, wherein all or part of the hinge and constant region of said light chain or heavy chain or both chains have been replaced with corresponding regions derived from an antibody of a second mammalian species.

9. A chimeric recombinant antibody homolog according to claim 8, wherein:
   (a) the amino acid sequence of the light chain variable region is SEQ ID NO: 15; and
   (b) the amino acid sequence of the heavy chain variable region is SEQ ID NO: 10.

10. A 5A8-mimetic peptide displaying the properties of an antibody homolog according to claim 1.

11. A 5A8-mimetic peptide which inhibits HIV-induced syncytia formation between CD4+ cells.

12. A 5A8-mimetic peptide which inhibits infection of CD4+ cells by HIV.

13. A composition for inhibiting HIV-1 replication, comprising an immunotherapeutically effective amount of one or more members selected from the group consisting of: an antibody homolog, an antibody homolog that is a conjugate, and a 5A8-mimetic peptide, each of said members having the property of (a) binding to human CD4; (b) not significantly blocking binding of HIV gp120 to human CD4; and (c) blocking HIV-induced syncytia formation between CD4+ cells at least as well as OKT4A; in combination with a pharmaceutically acceptable carrier.

14. The composition of claim 13, further comprising one or more agents which significantly block binding of HIV gp120 to CD4.

15. The composition of claim 14, wherein said one or more agents is selected from the group consisting of CD4 V1-specific antibody homologs, CD4 V1 polypeptides and anti-HIV gp120 antibody homologs.

16. A method for inhibiting HIV-1 replication in a mammal, comprising administering to the mammal an immunotherapeutically effective amount of one or more members selected from the group consisting of: an antibody homolog, an antibody homolog that is a conjugate, and a 5A8-mimetic peptide, each of said members having the property of (a) binding to human CD4; (b) not significantly blocking binding of HIV gp120 to human CD4; and (c) blocking HIV-induced syncytia formation between CD4+ cells at least as well as OKT4A; in combination with a pharmaceutically acceptable carrier.

17. An antibody homolog derived from a hybridoma selected from the group of hybridomas having accession numbers HB 10881 (5A8), HB 10882 (1F8) and HB 10883 (5F2).

18. An antibody homolog according to claim 17, derived from the hybridoma having accession number HB 10881 (5A8).

19. An antibody homolog according to claim 17, wherein the antibody homolog is an intact monoclonal antibody.

20. An antibody homolog according to claim 17, wherein the antibody homolog is selected from the group consisting of Fab fragments, Fab'; fragments, F(ab')2 fragments and F(v) fragments.

21. An antibody homolog comprising an antibody homolog according to claim 17, linked to one or more members independently selected from the group consisting of: an antibody homolog that (a) binds to human CD4; (b) does not significantly block binding of HIV gp120 to human CD4; and (c) blocks HIV-induced syncytia formation between CD4+ cells at least as well as OKT4A, a 5A8-mimetic peptide, a detectable agent, a cytotoxic agent and a pharmaceutical agent.

* * * * *

SEQUENCE LISTING ( 1 ) GENERAL INFORMATION:

( i i i ) NUMBER OF SEQUENCES: 61

( 2 ) INFORMATION FOR SEQ ID NO:1:

( i ) SEQUENCE CHARACTERISTICS:
        ( A ) LENGTH: 2571 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: sig_peptide
        ( B ) LOCATION: 1..87

( i x ) FEATURE:
        ( A ) NAME/KEY: mat_peptide
        ( B ) LOCATION: 88..2568

( i x ) FEATURE:
        ( A ) NAME/KEY: misc_feature
        ( B ) LOCATION: 1533..1534
        ( D ) OTHER INFORMATION: /note= ""gp120/gp41 cleavage site""

( i x ) FEATURE:
        ( A ) NAME/KEY: CDS
        ( B ) LOCATION: 1..2568

( i x ) FEATURE:
        ( A ) NAME/KEY: misc_feature
        ( B ) LOCATION: 1
        ( D ) OTHER INFORMATION: /note= "pre-HIV gp160"

( x i ) SEQUENCE DESCRIPTION: SEQ ID NO:1:

```
ATG  AGA  GTG  AAG  GAG  AAA  TAT  CAG  CAC  TTG  TGG  AGA  TGG  GGG  TGG  AGA       48
Met  Arg  Val  Lys  Glu  Lys  Tyr  Gln  His  Leu  Trp  Arg  Trp  Gly  Trp  Arg
-29            -25                      -20                     -15

TGG  GGC  ACC  ATG  CTC  CTT  GGG  ATG  TTG  ATG  ATC  TGT  AGT  GCT  ACA  GAA       96
Trp  Gly  Thr  Met  Leu  Leu  Gly  Met  Leu  Met  Ile  Cys  Ser  Ala  Thr  Glu
              -10                       -5                     1

AAA  TTG  TGG  GTC  ACA  GTC  TAT  TAT  GGG  GTA  CCT  GTG  TGG  AAG  GAA  GCA      144
Lys  Leu  Trp  Val  Thr  Val  Tyr  Tyr  Gly  Val  Pro  Val  Trp  Lys  Glu  Ala
      5                           10                  15

ACC  ACC  ACT  CTA  TTT  TGT  GCA  TCA  GAT  GCT  AAA  GCA  TAT  GAT  ACA  GAG      192
Thr  Thr  Thr  Leu  Phe  Cys  Ala  Ser  Asp  Ala  Lys  Ala  Tyr  Asp  Thr  Glu
 20                       25                  30                       35

GTA  CAT  AAT  GTT  TGG  GCC  ACA  CAT  GCC  TGT  GTA  CCC  ACA  GAC  CCC  AAC      240
Val  His  Asn  Val  Trp  Ala  Thr  His  Ala  Cys  Val  Pro  Thr  Asp  Pro  Asn
                         40                  45                       50

CCA  CAA  GAA  GTA  GTA  TTG  GTA  AAT  GTG  ACA  GAA  AAT  TTT  AAC  ATG  TGG      288
Pro  Gln  Glu  Val  Val  Leu  Val  Asn  Val  Thr  Glu  Asn  Phe  Asn  Met  Trp
                55                       60                  65
```

| | | | | | | | | | | | | | | | | |
|---|---|---|---|---|---|---|---|---|---|---|---|---|---|---|---|---|
| AAA | AAT | GAC | ATG | GTA | GAA | CAG | ATG | CAT | GAG | GAT | ATA | ATC | AGT | TTA | TGG | 336 |
| Lys | Asn | Asp | Met | Val | Glu | Gln | Met | His | Glu | Asp | Ile | Ile | Ser | Leu | Trp | |
| | | 70 | | | | | 75 | | | | | 80 | | | | |
| GAT | CAA | AGC | CTA | AAG | CCA | TGT | GTA | AAA | TTA | ACC | CCA | CTC | TGT | GTT | AGT | 384 |
| Asp | Gln | Ser | Leu | Lys | Pro | Cys | Val | Lys | Leu | Thr | Pro | Leu | Cys | Val | Ser | |
| | 85 | | | | | 90 | | | | | 95 | | | | | |
| TTA | AAG | TGC | ACT | GAT | TTG | AAG | AAT | GAT | ACT | AAT | ACC | AAT | AGT | AGT | AGC | 432 |
| Leu | Lys | Cys | Thr | Asp | Leu | Lys | Asn | Asp | Thr | Asn | Thr | Asn | Ser | Ser | Ser | |
| 100 | | | | | 105 | | | | | 110 | | | | | 115 | |
| GGG | AGA | ATG | ATA | ATG | GAG | AAA | GGA | GAG | ATA | AAA | AAC | TGC | TCT | TTC | AAT | 480 |
| Gly | Arg | Met | Ile | Met | Glu | Lys | Gly | Glu | Ile | Lys | Asn | Cys | Ser | Phe | Asn | |
| | | | | 120 | | | | | 125 | | | | | 130 | | |
| ATC | AGC | ACA | AGC | ATA | AGA | GGT | AAG | GTG | CAG | AAA | GAA | TAT | GCA | TTT | TTT | 528 |
| Ile | Ser | Thr | Ser | Ile | Arg | Gly | Lys | Val | Gln | Lys | Glu | Tyr | Ala | Phe | Phe | |
| | | | 135 | | | | | 140 | | | | | 145 | | | |
| TAT | AAA | CTT | GAT | ATA | ATA | CCA | ATA | GAT | AAT | GAT | ACT | ACC | AGC | TAT | AAG | 576 |
| Tyr | Lys | Leu | Asp | Ile | Ile | Pro | Ile | Asp | Asn | Asp | Thr | Thr | Ser | Tyr | Lys | |
| | | 150 | | | | | 155 | | | | | 160 | | | | |
| TTG | ACA | AGT | TGT | AAC | ACC | TCA | GTC | ATT | ACA | CAG | GCC | TGT | CCA | AAG | GTA | 624 |
| Leu | Thr | Ser | Cys | Asn | Thr | Ser | Val | Ile | Thr | Gln | Ala | Cys | Pro | Lys | Val | |
| | 165 | | | | | 170 | | | | | 175 | | | | | |
| TCC | TTT | GAG | CCA | ATT | CCC | ATA | CAT | TAT | TGT | GCC | CCG | GCT | GGT | TTT | GCG | 672 |
| Ser | Phe | Glu | Pro | Ile | Pro | Ile | His | Tyr | Cys | Ala | Pro | Ala | Gly | Phe | Ala | |
| 180 | | | | | 185 | | | | | 190 | | | | | 195 | |
| ATT | CTA | AAA | TGT | AAT | AAT | AAG | ACG | TTC | AAT | GGA | ACA | GGA | CCA | TGT | ACA | 720 |
| Ile | Leu | Lys | Cys | Asn | Asn | Lys | Thr | Phe | Asn | Gly | Thr | Gly | Pro | Cys | Thr | |
| | | | | 200 | | | | | 205 | | | | | 210 | | |
| AAT | GTC | AGC | ACA | GTA | CAA | TGT | ACA | CAT | GGA | ATT | AGG | CCA | GTA | GTA | TCA | 768 |
| Asn | Val | Ser | Thr | Val | Gln | Cys | Thr | His | Gly | Ile | Arg | Pro | Val | Val | Ser | |
| | | | 215 | | | | | 220 | | | | | 225 | | | |
| ACT | CAA | CTG | CTG | TTA | AAT | GGC | AGT | CTA | GCA | GAA | GAA | GAG | GTA | GTA | ATT | 816 |
| Thr | Gln | Leu | Leu | Leu | Asn | Gly | Ser | Leu | Ala | Glu | Glu | Glu | Val | Val | Ile | |
| | | 230 | | | | | 235 | | | | | 240 | | | | |
| AGA | TCT | GTC | AAT | TTC | ACG | GAC | AAT | GCT | AAA | ACC | ATA | ATA | GTA | CAG | CTG | 864 |
| Arg | Ser | Val | Asn | Phe | Thr | Asp | Asn | Ala | Lys | Thr | Ile | Ile | Val | Gln | Leu | |
| | 245 | | | | | 250 | | | | | 255 | | | | | |
| AAC | ACA | TCT | GTA | GAA | ATT | AAT | TGT | ACA | AGA | CCC | AAC | AAC | AAT | ACA | AGA | 912 |
| Asn | Thr | Ser | Val | Glu | Ile | Asn | Cys | Thr | Arg | Pro | Asn | Asn | Asn | Thr | Arg | |
| 260 | | | | | 265 | | | | | 270 | | | | | 275 | |
| AAA | AGA | ATC | CGT | ATC | CAG | AGA | GGA | CCA | GGG | AGA | GCA | TTT | GTT | ACA | ATA | 960 |
| Lys | Arg | Ile | Arg | Ile | Gln | Arg | Gly | Pro | Gly | Arg | Ala | Phe | Val | Thr | Ile | |
| | | | | 280 | | | | | 285 | | | | | 290 | | |
| GGA | AAA | ATA | GGA | AAT | ATG | AGA | CAA | GCA | CAT | TGT | AAC | ATT | AGT | AGA | GCA | 1008 |
| Gly | Lys | Ile | Gly | Asn | Met | Arg | Gln | Ala | His | Cys | Asn | Ile | Ser | Arg | Ala | |
| | | | 295 | | | | | 300 | | | | | 305 | | | |
| AAA | TGG | AAT | AAC | ACT | TTA | AAA | CAG | ATA | GCT | AGC | AAA | TTA | AGA | GAA | CAA | 1056 |
| Lys | Trp | Asn | Asn | Thr | Leu | Lys | Gln | Ile | Ala | Ser | Lys | Leu | Arg | Glu | Gln | |
| | | 310 | | | | | 315 | | | | | 320 | | | | |
| TTT | GGA | AAT | AAT | AAA | ACA | ATA | ATC | TTT | AAG | CAA | TCC | TCA | GGA | GGG | GAC | 1104 |
| Phe | Gly | Asn | Asn | Lys | Thr | Ile | Ile | Phe | Lys | Gln | Ser | Ser | Gly | Gly | Asp | |
| | 325 | | | | | 330 | | | | | 335 | | | | | |
| CCA | GAA | ATT | GTA | ACG | CAC | AGT | TTT | AAT | TGT | GGA | GGG | GAA | TTT | TTC | TAC | 1152 |
| Pro | Glu | Ile | Val | Thr | His | Ser | Phe | Asn | Cys | Gly | Gly | Glu | Phe | Phe | Tyr | |
| 340 | | | | | 345 | | | | | 350 | | | | | 355 | |
| TGT | AAT | TCA | ACA | CAA | CTG | TTT | AAT | AGT | ACT | TGG | TTT | AAT | AGT | ACT | TGG | 1200 |
| Cys | Asn | Ser | Thr | Gln | Leu | Phe | Asn | Ser | Thr | Trp | Phe | Asn | Ser | Thr | Trp | |
| | | | | 360 | | | | | 365 | | | | | 370 | | |
| AGT | ACT | GAA | GGG | TCA | AAT | AAC | ACT | GAA | GGA | AGT | GAC | ACA | ATC | ACC | CTC | 1248 |
| Ser | Thr | Glu | Gly | Ser | Asn | Asn | Thr | Glu | Gly | Ser | Asp | Thr | Ile | Thr | Leu | |
| | | | 375 | | | | | 380 | | | | | 385 | | | |

| | | | | | | | | | | | | | | | | |
|---|---|---|---|---|---|---|---|---|---|---|---|---|---|---|---|---|
| CCA | TGC | AGA | ATA | AAA | CAA | ATT | ATA | AAC | ATG | TGG | CAG | AAA | GTA | GGA | AAA | 1296 |
| Pro | Cys | Arg | Ile | Lys | Gln | Ile | Ile | Asn | Met | Trp | Gln | Lys | Val | Gly | Lys | |
| | 390 | | | | | 395 | | | | | 400 | | | | | |
| GCA | ATG | TAT | GCC | CCT | CCC | ATC | AGT | GGA | CAA | ATT | AGA | TGT | TCA | TCA | AAT | 1344 |
| Ala | Met | Tyr | Ala | Pro | Pro | Ile | Ser | Gly | Gln | Ile | Arg | Cys | Ser | Ser | Asn | |
| 405 | | | | | 410 | | | | | 415 | | | | | | |
| ATT | ACA | GGG | CTG | CTA | TTA | ACA | AGA | GAT | GGT | GGT | AAT | AGC | AAC | AAT | GAG | 1392 |
| Ile | Thr | Gly | Leu | Leu | Leu | Thr | Arg | Asp | Gly | Gly | Asn | Ser | Asn | Asn | Glu | |
| 420 | | | | | 425 | | | | | 430 | | | | | 435 | |
| TCC | GAG | ATC | TTC | AGA | CCT | GGA | GGA | GGA | GAT | ATG | AGG | GAC | AAT | TGG | AGA | 1440 |
| Ser | Glu | Ile | Phe | Arg | Pro | Gly | Gly | Gly | Asp | Met | Arg | Asp | Asn | Trp | Arg | |
| | | | | 440 | | | | | 445 | | | | | 450 | | |
| AGT | GAA | TTA | TAT | AAA | TAT | AAA | GTA | GTA | AAA | ATT | GAA | CCA | TTA | GGA | GTA | 1488 |
| Ser | Glu | Leu | Tyr | Lys | Tyr | Lys | Val | Val | Lys | Ile | Glu | Pro | Leu | Gly | Val | |
| | | | 455 | | | | | 460 | | | | | 465 | | | |
| GCA | CCC | ACC | AAG | GCA | AAG | AGA | AGA | GTG | GTG | CAG | AGA | GAA | AAA | AGA | GCA | 1536 |
| Ala | Pro | Thr | Lys | Ala | Lys | Arg | Arg | Val | Val | Gln | Arg | Glu | Lys | Arg | Ala | |
| | | 470 | | | | | 475 | | | | | 480 | | | | |
| GTG | GGA | ATA | GGA | GCT | TTG | TTC | CTT | GGG | TTC | TTG | GGA | GCA | GCA | GGA | AGC | 1584 |
| Val | Gly | Ile | Gly | Ala | Leu | Phe | Leu | Gly | Phe | Leu | Gly | Ala | Ala | Gly | Ser | |
| | 485 | | | | | 490 | | | | | 495 | | | | | |
| ACT | ATG | GGC | GCA | GCG | TCA | ATG | ACG | CTG | ACG | GTA | CAG | GCC | AGA | CAA | TTA | 1632 |
| Thr | Met | Gly | Ala | Ala | Ser | Met | Thr | Leu | Thr | Val | Gln | Ala | Arg | Gln | Leu | |
| 500 | | | | | 505 | | | | | 510 | | | | | 515 | |
| TTG | TCT | GGT | ATA | GTG | CAG | CAG | CAG | AAC | AAT | TTG | CTG | AGG | GCT | ATT | GAG | 1680 |
| Leu | Ser | Gly | Ile | Val | Gln | Gln | Gln | Asn | Asn | Leu | Leu | Arg | Ala | Ile | Glu | |
| | | | | 520 | | | | | 525 | | | | | 530 | | |
| GCG | CAA | CAG | CAT | CTG | TTG | CAA | CTC | ACA | GTC | TGG | GGC | ATC | AAG | CAG | CTC | 1728 |
| Ala | Gln | Gln | His | Leu | Leu | Gln | Leu | Thr | Val | Trp | Gly | Ile | Lys | Gln | Leu | |
| | | | 535 | | | | | 540 | | | | | 545 | | | |
| CAG | GCA | AGA | ATC | CTG | GCT | GTG | GAA | AGA | TAC | CTA | AAG | GAT | CAA | CAG | CTC | 1776 |
| Gln | Ala | Arg | Ile | Leu | Ala | Val | Glu | Arg | Tyr | Leu | Lys | Asp | Gln | Gln | Leu | |
| | | 550 | | | | | 555 | | | | | 560 | | | | |
| CTA | GGG | ATT | TGG | GGT | TGC | TCT | GGA | AAA | CTC | ATT | TGC | ACC | ACT | GCT | GTG | 1824 |
| Leu | Gly | Ile | Trp | Gly | Cys | Ser | Gly | Lys | Leu | Ile | Cys | Thr | Thr | Ala | Val | |
| | 565 | | | | | 570 | | | | | 575 | | | | | |
| CCT | TGG | AAT | GCT | AGT | TGG | AGT | AAT | AAA | TCT | CTG | GAA | CAG | ATT | TGG | AAT | 1872 |
| Pro | Trp | Asn | Ala | Ser | Trp | Ser | Asn | Lys | Ser | Leu | Glu | Gln | Ile | Trp | Asn | |
| 580 | | | | | 585 | | | | | 590 | | | | | 595 | |
| CAC | ACG | ACC | TGG | ATG | GAG | TGG | GAC | AGA | GAA | ATT | AAC | AAT | TAC | ACA | AGC | 1920 |
| His | Thr | Thr | Trp | Met | Glu | Trp | Asp | Arg | Glu | Ile | Asn | Asn | Tyr | Thr | Ser | |
| | | | | 600 | | | | | 605 | | | | | 610 | | |
| TTA | ATA | CAC | TCC | TTA | ATT | GAA | GAA | TCG | CAA | AAC | CAG | CAA | GAA | AAG | AAT | 1968 |
| Leu | Ile | His | Ser | Leu | Ile | Glu | Glu | Ser | Gln | Asn | Gln | Gln | Glu | Lys | Asn | |
| | | | 615 | | | | | 620 | | | | | 625 | | | |
| GAA | CAA | GAA | TTA | TTG | GAA | TTA | GAT | AAA | TGG | GCA | AGT | TTG | TGG | AAT | TGG | 2016 |
| Glu | Gln | Glu | Leu | Leu | Glu | Leu | Asp | Lys | Trp | Ala | Ser | Leu | Trp | Asn | Trp | |
| | | 630 | | | | | 635 | | | | | 640 | | | | |
| TTT | AAC | ATA | ACA | AAT | TGG | CTG | TGG | TAT | ATA | AAA | TTA | TTC | ATA | ATG | ATA | 2064 |
| Phe | Asn | Ile | Thr | Asn | Trp | Leu | Trp | Tyr | Ile | Lys | Leu | Phe | Ile | Met | Ile | |
| | 645 | | | | | 650 | | | | | 655 | | | | | |
| GTA | GGA | GGC | TTG | GTA | GGT | TTA | AGA | ATA | GTT | TTT | GCT | GTA | CTT | TCT | ATA | 2112 |
| Val | Gly | Gly | Leu | Val | Gly | Leu | Arg | Ile | Val | Phe | Ala | Val | Leu | Ser | Ile | |
| 660 | | | | | 665 | | | | | 670 | | | | | 675 | |
| GTG | AAT | AGA | GTT | AGG | CAG | GGA | TAT | TCA | CCA | TTA | TCG | TTT | CAG | ACC | CAC | 2160 |
| Val | Asn | Arg | Val | Arg | Gln | Gly | Tyr | Ser | Pro | Leu | Ser | Phe | Gln | Thr | His | |
| | | | | 680 | | | | | 685 | | | | | 690 | | |
| CTC | CCA | ACC | CCG | AGG | GGA | CCC | GAC | AGG | CCC | GAA | GGA | ATA | GAA | GAA | GAA | 2208 |
| Leu | Pro | Thr | Pro | Arg | Gly | Pro | Asp | Arg | Pro | Glu | Gly | Ile | Glu | Glu | Glu | |
| | | | 695 | | | | | 700 | | | | | 705 | | | |

| | | | | | | | | | | | | | | | | |
|---|---|---|---|---|---|---|---|---|---|---|---|---|---|---|---|---|
| GGT | GGA | GAG | AGA | GAC | AGA | GAC | AGA | TCC | ATT | CGA | TTA | GTG | AAC | GGA | TCC | 2256 |
| Gly | Gly | Glu | Arg | Asp | Arg | Asp | Arg | Ser | Ile | Arg | Leu | Val | Asn | Gly | Ser | |
| | | 710 | | | | 715 | | | | | 720 | | | | | |
| TTG | GCA | CTT | ATC | TGG | GAC | GAT | CTG | CGG | AGC | CTG | TGC | CTC | TTC | AGC | TAC | 2304 |
| Leu | Ala | Leu | Ile | Trp | Asp | Asp | Leu | Arg | Ser | Leu | Cys | Leu | Phe | Ser | Tyr | |
| 725 | | | | | 730 | | | | | 735 | | | | | | |
| CAC | CGC | TTG | AGA | GAC | TTA | CTC | TTG | ATT | GTA | ACG | AGG | ATT | GTG | GAA | CTT | 2352 |
| His | Arg | Leu | Arg | Asp | Leu | Leu | Leu | Ile | Val | Thr | Arg | Ile | Val | Glu | Leu | |
| 740 | | | | | 745 | | | | | 750 | | | | | 755 | |
| CTG | GGA | CGC | AGG | GGG | TGG | GAA | GCC | CTC | AAA | TAT | TGG | TGG | AAT | CTC | CTA | 2400 |
| Leu | Gly | Arg | Arg | Gly | Trp | Glu | Ala | Leu | Lys | Tyr | Trp | Trp | Asn | Leu | Leu | |
| | | | | 760 | | | | 765 | | | | | 770 | | | |
| CAG | TAT | TGG | AGT | CAG | GAA | CTA | AAG | AAT | AGT | GCT | GTT | AGC | TTG | CTC | AAT | 2448 |
| Gln | Tyr | Trp | Ser | Gln | Glu | Leu | Lys | Asn | Ser | Ala | Val | Ser | Leu | Leu | Asn | |
| | | | 775 | | | | | 780 | | | | | 785 | | | |
| GCC | ACA | GCC | ATA | GCA | GTA | GCT | GAG | GGG | ACA | GAT | AGG | GTT | ATA | GAA | GTA | 2496 |
| Ala | Thr | Ala | Ile | Ala | Val | Ala | Glu | Gly | Thr | Asp | Arg | Val | Ile | Glu | Val | |
| | | 790 | | | | | 795 | | | | | 800 | | | | |
| GTA | CAA | GGA | GCT | TGT | AGA | GCT | ATT | CGC | CAC | ATA | CCT | AGA | AGA | ATA | AGA | 2544 |
| Val | Gln | Gly | Ala | Cys | Arg | Ala | Ile | Arg | His | Ile | Pro | Arg | Arg | Ile | Arg | |
| | 805 | | | | | 810 | | | | | 815 | | | | | |
| CAG | GGC | TTG | GAA | AGG | ATT | TTG | CTA | TAA | | | | | | | | 2571 |
| Gln | Gly | Leu | Glu | Arg | Ile | Leu | Leu | | | | | | | | | |
| 820 | | | | | 825 | | | | | | | | | | | |

( 2 ) INFORMATION FOR SEQ ID NO:2:

( i ) SEQUENCE CHARACTERISTICS:
        ( A ) LENGTH: 856 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | |
|---|---|---|---|---|---|---|---|---|---|---|---|---|---|
| Met | Arg | Val | Lys | Glu | Lys | Tyr | Gln | His | Leu | Trp | Arg | Trp | Gly | Trp | Arg |
| -29 | | | -25 | | | | | -20 | | | | | -15 | | |
| Trp | Gly | Thr | Met | Leu | Leu | Gly | Met | Leu | Met | Ile | Cys | Ser | Ala | Thr | Glu |
| | | | -10 | | | | -5 | | | | | | 1 | | |
| Lys | Leu | Trp | Val | Thr | Val | Tyr | Tyr | Gly | Val | Pro | Val | Trp | Lys | Glu | Ala |
| | 5 | | | | | 10 | | | | 15 | | | | | |
| Thr | Thr | Thr | Leu | Phe | Cys | Ala | Ser | Asp | Ala | Lys | Ala | Tyr | Asp | Thr | Glu |
| 20 | | | | | 25 | | | | 30 | | | | | | 35 |
| Val | His | Asn | Val | Trp | Ala | Thr | His | Ala | Cys | Val | Pro | Thr | Asp | Pro | Asn |
| | | | | 40 | | | | 45 | | | | | | 50 | |
| Pro | Gln | Glu | Val | Val | Leu | Val | Asn | Val | Thr | Glu | Asn | Phe | Asn | Met | Trp |
| | | | 55 | | | | 60 | | | | | 65 | | | |
| Lys | Asn | Asp | Met | Val | Glu | Gln | Met | His | Glu | Asp | Ile | Ile | Ser | Leu | Trp |
| | | 70 | | | | 75 | | | | 80 | | | | | |
| Asp | Gln | Ser | Leu | Lys | Pro | Cys | Val | Lys | Leu | Thr | Pro | Leu | Cys | Val | Ser |
| | 85 | | | | 90 | | | | 95 | | | | | | |
| Leu | Lys | Cys | Thr | Asp | Leu | Lys | Asn | Asp | Thr | Asn | Thr | Asn | Ser | Ser | Ser |
| 100 | | | | 105 | | | | 110 | | | | | 115 | | |
| Gly | Arg | Met | Ile | Met | Glu | Lys | Gly | Glu | Ile | Lys | Asn | Cys | Ser | Phe | Asn |
| | | | 120 | | | | 125 | | | | 130 | | | | |
| Ile | Ser | Thr | Ser | Ile | Arg | Gly | Lys | Val | Gln | Lys | Glu | Tyr | Ala | Phe | Phe |
| | | 135 | | | | 140 | | | | 145 | | | | | |
| Tyr | Lys | Leu | Asp | Ile | Ile | Pro | Ile | Asp | Asn | Asp | Thr | Thr | Ser | Tyr | Lys |
| | 150 | | | | 155 | | | | 160 | | | | | | |

```
Leu  Thr  Ser  Cys  Asn  Thr  Ser  Val  Ile  Thr  Gln  Ala  Cys  Pro  Lys  Val
     165                 170                 175

Ser  Phe  Glu  Pro  Ile  Pro  Ile  His  Tyr  Cys  Ala  Pro  Ala  Gly  Phe  Ala
180                      185                 190                           195

Ile  Leu  Lys  Cys  Asn  Lys  Thr  Phe  Asn  Gly  Thr  Gly  Pro  Cys  Thr
                    200                 205                      210

Asn  Val  Ser  Thr  Val  Gln  Cys  Thr  His  Gly  Ile  Arg  Pro  Val  Val  Ser
               215                      220                      225

Thr  Gln  Leu  Leu  Leu  Asn  Gly  Ser  Leu  Ala  Glu  Glu  Val  Val  Ile
          230                      235                 240

Arg  Ser  Val  Asn  Phe  Thr  Asp  Asn  Ala  Lys  Thr  Ile  Ile  Val  Gln  Leu
     245                      250                      255

Asn  Thr  Ser  Val  Glu  Ile  Asn  Cys  Thr  Arg  Pro  Asn  Asn  Asn  Thr  Arg
260                      265                      270                           275

Lys  Arg  Ile  Arg  Ile  Gln  Arg  Gly  Pro  Gly  Arg  Ala  Phe  Val  Thr  Ile
                    280                      285                      290

Gly  Lys  Ile  Gly  Asn  Met  Arg  Gln  Ala  His  Cys  Asn  Ile  Ser  Arg  Ala
                    295                      300                 305

Lys  Trp  Asn  Asn  Thr  Leu  Lys  Gln  Ile  Ala  Ser  Lys  Leu  Arg  Glu  Gln
          310                      315                      320

Phe  Gly  Asn  Asn  Lys  Thr  Ile  Ile  Phe  Lys  Gln  Ser  Ser  Gly  Gly  Asp
     325                      330                 335

Pro  Glu  Ile  Val  Thr  His  Ser  Phe  Asn  Cys  Gly  Gly  Glu  Phe  Phe  Tyr
340                      345                      350                           355

Cys  Asn  Ser  Thr  Gln  Leu  Phe  Asn  Ser  Thr  Trp  Phe  Asn  Ser  Thr  Trp
                    360                      365                      370

Ser  Thr  Glu  Gly  Ser  Asn  Asn  Thr  Glu  Gly  Ser  Asp  Thr  Ile  Thr  Leu
               375                      380                      385

Pro  Cys  Arg  Ile  Lys  Gln  Ile  Ile  Asn  Met  Trp  Gln  Lys  Val  Gly  Lys
               390                      395                 400

Ala  Met  Tyr  Ala  Pro  Pro  Ile  Ser  Gly  Gln  Ile  Arg  Cys  Ser  Ser  Asn
     405                      410                      415

Ile  Thr  Gly  Leu  Leu  Leu  Thr  Arg  Asp  Gly  Gly  Asn  Ser  Asn  Asn  Glu
420                      425                      430                           435

Ser  Glu  Ile  Phe  Arg  Pro  Gly  Gly  Gly  Asp  Met  Arg  Asp  Asn  Trp  Arg
                    440                      445                      450

Ser  Glu  Leu  Tyr  Lys  Tyr  Lys  Val  Val  Lys  Ile  Glu  Pro  Leu  Gly  Val
               455                      460                      465

Ala  Pro  Thr  Lys  Ala  Lys  Arg  Arg  Val  Val  Gln  Arg  Glu  Lys  Arg  Ala
          470                      475                 480

Val  Gly  Ile  Gly  Ala  Leu  Phe  Leu  Gly  Phe  Leu  Gly  Ala  Ala  Gly  Ser
     485                      490                 495

Thr  Met  Gly  Ala  Ala  Ser  Met  Thr  Leu  Thr  Val  Gln  Ala  Arg  Gln  Leu
500                      505                      510                           515

Leu  Ser  Gly  Ile  Val  Gln  Gln  Asn  Asn  Leu  Leu  Arg  Ala  Ile  Glu
                    520                      525                      530

Ala  Gln  Gln  His  Leu  Leu  Gln  Leu  Thr  Val  Trp  Gly  Ile  Lys  Gln  Leu
               535                      540                      545

Gln  Ala  Arg  Ile  Leu  Ala  Val  Glu  Arg  Tyr  Leu  Lys  Asp  Gln  Gln  Leu
               550                      555                 560

Leu  Gly  Ile  Trp  Gly  Cys  Ser  Gly  Lys  Leu  Ile  Cys  Thr  Thr  Ala  Val
          565                      570                 575

Pro  Trp  Asn  Ala  Ser  Trp  Ser  Asn  Lys  Ser  Leu  Glu  Gln  Ile  Trp  Asn
580                      585                      590                           595
```

| His | Thr | Thr | Trp | Met 600 | Glu | Trp | Asp | Arg | Ile 605 | Asn | Asn | Tyr | Thr | Ser 610 |
| Leu | Ile | His | Ser 615 | Leu | Ile | Glu | Glu | Ser 620 | Gln | Asn | Gln | Gln | Glu 625 | Lys | Asn |
| Glu | Gln | Glu 630 | Leu | Leu | Glu | Leu | Asp 635 | Lys | Trp | Ala | Ser | Leu 640 | Trp | Asn | Trp |
| Phe | Asn 645 | Ile | Thr | Asn | Trp | Leu 650 | Trp | Tyr | Ile | Lys | Leu 655 | Phe | Ile | Met | Ile |
| Val 660 | Gly | Gly | Leu | Val | Gly 665 | Leu | Arg | Ile | Val | Phe 670 | Ala | Val | Leu | Ser | Ile 675 |
| Val | Asn | Arg | Val | Arg 680 | Gln | Gly | Tyr | Ser | Pro 685 | Leu | Ser | Phe | Gln | Thr 690 | His |
| Leu | Pro | Thr | Pro 695 | Arg | Gly | Pro | Asp | Arg 700 | Pro | Glu | Gly | Ile | Glu 705 | Glu | Glu |
| Gly | Gly | Glu 710 | Arg | Asp | Arg | Asp | Arg 715 | Ser | Ile | Arg | Leu | Val 720 | Asn | Gly | Ser |
| Leu | Ala | Leu 725 | Ile | Trp | Asp | Asp 730 | Leu | Arg | Ser | Leu | Cys 735 | Leu | Phe | Ser | Tyr |
| His 740 | Arg | Leu | Arg | Asp | Leu 745 | Leu | Leu | Ile | Val | Thr 750 | Arg | Ile | Val | Glu | Leu 755 |
| Leu | Gly | Arg | Arg | Gly 760 | Trp | Glu | Ala | Leu | Lys 765 | Tyr | Trp | Trp | Asn | Leu 770 | Leu |
| Gln | Tyr | Trp | Ser 775 | Gln | Glu | Leu | Lys | Asn 780 | Ser | Ala | Val | Ser | Leu 785 | Leu | Asn |
| Ala | Thr | Ala 790 | Ile | Ala | Val | Ala | Glu 795 | Gly | Thr | Asp | Arg | Val 800 | Ile | Glu | Val |
| Val | Gln 805 | Gly | Ala | Cys | Arg | Ala 810 | Ile | Arg | His | Ile | Pro 815 | Arg | Arg | Ile | Arg |
| Gln 820 | Gly | Leu | Glu | Arg | Ile 825 | Leu | Leu | | | | | | | | |

( 2 ) INFORMATION FOR SEQ ID NO:3:

( i ) SEQUENCE CHARACTERISTICS:
        ( A ) LENGTH: 1497 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..1494

( i x ) FEATURE:
        ( A ) NAME/KEY: misc_feature
        ( B ) LOCATION: 1
        ( D ) OTHER INFORMATION: /note= "soluble HIV gp120"

( x i ) SEQUENCE DESCRIPTION: SEQ ID NO:3:

| ATG | GAT | GCA | ATG | AAG | AGA | GGG | CTC | TGC | TGT | GTG | CTG | CTG | CTG | TGT | GGA | 48 |
| Met | Asp | Ala | Met | Lys 5 | Arg | Gly | Leu | Cys | Cys 10 | Val | Leu | Leu | Leu | Cys 15 | Gly | |
| 1 | | | | | | | | | | | | | | | | |

| GCA | GTC | TTC | GTT | TCG | CCC | AGC | CAG | GAA | ATC | CAT | GCC | CGA | TTC | AGA | AGA | 96 |
| Ala | Val | Phe | Val 20 | Ser | Pro | Ser | Gln | Glu 25 | Ile | His | Ala | Arg | Phe 30 | Arg | Arg | |

| | | | | | | | | | | | | | | | | |
|---|---|---|---|---|---|---|---|---|---|---|---|---|---|---|---|---|
| GGA | GCC | AGA | TCC | ATG | GTA | CCT | GTG | TGG | AAG | GAA | GCA | ACC | ACC | ACT | CTA | 144 |
| Gly | Ala | Arg | Ser | Met | Val | Pro | Val | Trp | Lys | Glu | Ala | Thr | Thr | Thr | Leu | |
| | | 35 | | | | 40 | | | | | | 45 | | | | |
| TTT | TGT | GCA | TCA | GAT | GCT | AAA | GCA | TAT | GAT | ACA | GAG | GTA | CAT | AAT | GTT | 192 |
| Phe | Cys | Ala | Ser | Asp | Ala | Lys | Ala | Tyr | Asp | Thr | Glu | Val | His | Asn | Val | |
| | 50 | | | | | 55 | | | | | 60 | | | | | |
| TGG | GCC | ACA | CAT | GCC | TGT | GTA | CCC | ACA | GAC | CCC | AAC | CCA | CAA | GAA | GTA | 240 |
| Trp | Ala | Thr | His | Ala | Cys | Val | Pro | Thr | Asp | Pro | Asn | Pro | Gln | Glu | Val | |
| 65 | | | | | 70 | | | | | 75 | | | | | 80 | |
| GTA | TTG | GTA | AAT | GTG | ACA | GAA | AAT | TTT | AAC | ATG | TGG | AAA | AAT | GAC | ATG | 288 |
| Val | Leu | Val | Asn | Val | Thr | Glu | Asn | Phe | Asn | Met | Trp | Lys | Asn | Asp | Met | |
| | | | | 85 | | | | | 90 | | | | | 95 | | |
| GTA | GAA | CAG | ATG | CAT | GAG | GAT | ATA | ATC | AGT | TTA | TGG | GAT | CAA | AGC | CTA | 336 |
| Val | Glu | Gln | Met | His | Glu | Asp | Ile | Ile | Ser | Leu | Trp | Asp | Gln | Ser | Leu | |
| | | | 100 | | | | | 105 | | | | | 110 | | | |
| AAG | CCA | TGT | GTA | AAA | TTA | ACC | CCA | CTC | TGT | GTT | AGT | TTA | AAG | TGC | ACT | 384 |
| Lys | Pro | Cys | Val | Lys | Leu | Thr | Pro | Leu | Cys | Val | Ser | Leu | Lys | Cys | Thr | |
| | | | 115 | | | | 120 | | | | | 125 | | | | |
| GAT | TTG | AAG | AAT | GAT | ACT | AAT | ACC | AAT | AGT | AGT | AGC | GGG | AGA | ATG | ATA | 432 |
| Asp | Leu | Lys | Asn | Asp | Thr | Asn | Thr | Asn | Ser | Ser | Ser | Gly | Arg | Met | Ile | |
| | 130 | | | | | 135 | | | | | 140 | | | | | |
| ATG | GAG | AAA | GGA | GAG | ATA | AAA | AAC | TGC | TCT | TTC | AAT | ATC | AGC | ACA | AGC | 480 |
| Met | Glu | Lys | Gly | Glu | Ile | Lys | Asn | Cys | Ser | Phe | Asn | Ile | Ser | Thr | Ser | |
| 145 | | | | | 150 | | | | | 155 | | | | | 160 | |
| ATA | AGA | GGT | AAG | GTG | CAG | AAA | GAA | TAT | GCA | TTT | TTT | TAT | AAA | CTT | GAT | 528 |
| Ile | Arg | Gly | Lys | Val | Gln | Lys | Glu | Tyr | Ala | Phe | Phe | Tyr | Lys | Leu | Asp | |
| | | | | 165 | | | | | 170 | | | | | 175 | | |
| ATA | ATA | CCA | ATA | GAT | AAT | GAT | ACT | ACC | AGC | TAT | AAG | TTG | ACA | AGT | TGT | 576 |
| Ile | Ile | Pro | Ile | Asp | Asn | Asp | Thr | Thr | Ser | Tyr | Lys | Leu | Thr | Ser | Cys | |
| | | | 180 | | | | | 185 | | | | | 190 | | | |
| AAC | ACC | TCA | GTC | ATT | ACA | CAG | GCC | TGT | CCA | AAG | GTA | TCC | TTT | GAG | CCA | 624 |
| Asn | Thr | Ser | Val | Ile | Thr | Gln | Ala | Cys | Pro | Lys | Val | Ser | Phe | Glu | Pro | |
| | | 195 | | | | | 200 | | | | | 205 | | | | |
| ATT | CCC | ATA | CAT | TAT | TGT | GCC | CCG | GCT | GGT | TTT | GCG | ATT | CTA | AAA | TGT | 672 |
| Ile | Pro | Ile | His | Tyr | Cys | Ala | Pro | Ala | Gly | Phe | Ala | Ile | Leu | Lys | Cys | |
| | 210 | | | | | 215 | | | | | 220 | | | | | |
| AAT | AAT | AAG | ACG | TTC | AAT | GGA | ACA | GGA | CCA | TGT | ACA | AAT | GTC | AGC | ACA | 720 |
| Asn | Asn | Lys | Thr | Phe | Asn | Gly | Thr | Gly | Pro | Cys | Thr | Asn | Val | Ser | Thr | |
| 225 | | | | | 230 | | | | | 235 | | | | | 240 | |
| GTA | CAA | TGT | ACA | CAT | GGA | ATT | AGG | CCA | GTA | GTA | TCA | ACT | CAA | CTG | CTG | 768 |
| Val | Gln | Cys | Thr | His | Gly | Ile | Arg | Pro | Val | Val | Ser | Thr | Gln | Leu | Leu | |
| | | | | 245 | | | | | 250 | | | | | 255 | | |
| TTA | AAT | GGC | AGT | CTA | GCA | GAA | GAA | GAG | GTA | GTA | ATT | AGA | TCT | GTC | AAT | 816 |
| Leu | Asn | Gly | Ser | Leu | Ala | Glu | Glu | Glu | Val | Val | Ile | Arg | Ser | Val | Asn | |
| | | | 260 | | | | | 265 | | | | | 270 | | | |
| TTC | ACG | GAC | AAT | GCT | AAA | ACC | ATA | ATA | GTA | CAG | CTG | AAC | ACA | TCT | GTA | 864 |
| Phe | Thr | Asp | Asn | Ala | Lys | Thr | Ile | Ile | Val | Gln | Leu | Asn | Thr | Ser | Val | |
| | | 275 | | | | | 280 | | | | | 285 | | | | |
| GAA | ATT | AAT | TGT | ACA | AGA | CCC | AAC | AAC | AAT | ACA | AGA | AAA | AGA | ATC | CGT | 912 |
| Glu | Ile | Asn | Cys | Thr | Arg | Pro | Asn | Asn | Asn | Thr | Arg | Lys | Arg | Ile | Arg | |
| | 290 | | | | | 295 | | | | | 300 | | | | | |
| ATC | CAG | AGA | GGA | CCA | GGG | AGA | GCA | TTT | GTT | ACA | ATA | GGA | AAA | ATA | GGA | 960 |
| Ile | Gln | Arg | Gly | Pro | Gly | Arg | Ala | Phe | Val | Thr | Ile | Gly | Lys | Ile | Gly | |
| 305 | | | | | 310 | | | | | 315 | | | | | 320 | |
| AAT | ATG | AGA | CAA | GCA | CAT | TGT | AAC | ATT | AGT | AGA | GCA | AAA | TGG | AAT | AAC | 1008 |
| Asn | Met | Arg | Gln | Ala | His | Cys | Asn | Ile | Ser | Arg | Ala | Lys | Trp | Asn | Asn | |
| | | | | 325 | | | | | 330 | | | | | 335 | | |
| ACT | TTA | AAA | CAG | ATA | GCT | AGC | AAA | TTA | AGA | GAA | CAA | TTT | GGA | AAT | AAT | 1056 |
| Thr | Leu | Lys | Gln | Ile | Ala | Ser | Lys | Leu | Arg | Glu | Gln | Phe | Gly | Asn | Asn | |
| | | | 340 | | | | | 345 | | | | | 350 | | | |

| | | | | | | | | | | | | | | | |
|---|---|---|---|---|---|---|---|---|---|---|---|---|---|---|---|
| AAA | ACA | ATA | ATC | TTT | AAG | CAA | TCC | TCA | GGA | GGG | GAC | CCA | GAA | ATT | GTA | 1104
| Lys | Thr | Ile | Ile | Phe | Lys | Gln | Ser | Ser | Gly | Gly | Asp | Pro | Glu | Ile | Val |
| | | 355 | | | | 360 | | | | | 365 | | | | |
| ACG | CAC | AGT | TTT | AAT | TGT | GGA | GGG | GAA | TTT | TTC | TAC | TGT | AAT | TCA | ACA | 1152
| Thr | His | Ser | Phe | Asn | Cys | Gly | Gly | Glu | Phe | Phe | Tyr | Cys | Asn | Ser | Thr |
| | 370 | | | | | 375 | | | | | 380 | | | | |
| CAA | CTG | TTT | AAT | AGT | ACT | TGG | TTT | AAT | AGT | ACT | TGG | AGT | ACT | GAA | GGG | 1200
| Gln | Leu | Phe | Asn | Ser | Thr | Trp | Phe | Asn | Ser | Thr | Trp | Ser | Thr | Glu | Gly |
| 385 | | | | | 390 | | | | | 395 | | | | | 400 |
| TCA | AAT | AAC | ACT | GAA | GGA | AGT | GAC | ACA | ATC | ACC | CTC | CCA | TGC | AGA | ATA | 1248
| Ser | Asn | Asn | Thr | Glu | Gly | Ser | Asp | Thr | Ile | Thr | Leu | Pro | Cys | Arg | Ile |
| | | | | 405 | | | | | 410 | | | | | 415 | |
| AAA | CAA | ATT | ATA | AAC | ATG | TGG | CAG | AAA | GTA | GGA | AAA | GCA | ATG | TAT | GCC | 1296
| Lys | Gln | Ile | Ile | Asn | Met | Trp | Gln | Lys | Val | Gly | Lys | Ala | Met | Tyr | Ala |
| | | | 420 | | | | 425 | | | | | 430 | | | |
| CCT | CCC | ATC | AGT | GGA | CAA | ATT | AGA | TGT | TCA | TCA | AAT | ATT | ACA | GGG | CTG | 1344
| Pro | Pro | Ile | Ser | Gly | Gln | Ile | Arg | Cys | Ser | Ser | Asn | Ile | Thr | Gly | Leu |
| | | | 435 | | | | 440 | | | | | 445 | | | |
| CTA | TTA | ACA | AGA | GAT | GGT | GGT | AAT | AGC | AAC | AAT | GAG | TCC | GAG | ATC | TTC | 1392
| Leu | Leu | Thr | Arg | Asp | Gly | Gly | Asn | Ser | Asn | Asn | Glu | Ser | Glu | Ile | Phe |
| | | 450 | | | | | 455 | | | | | 460 | | | |
| AGA | CCT | GGA | GGA | GGA | GAT | ATG | AGG | GAC | AAT | TGG | AGA | AGT | GAA | TTA | TAT | 1440
| Arg | Pro | Gly | Gly | Gly | Asp | Met | Arg | Asp | Asn | Trp | Arg | Ser | Glu | Leu | Tyr |
| 465 | | | | | 470 | | | | | 475 | | | | | 480 |
| AAA | TAT | AAA | GTA | GTA | AAA | ATT | GAA | CCA | TTA | GGA | GTA | GCA | CCC | ACC | AAG | 1488
| Lys | Tyr | Lys | Val | Val | Lys | Ile | Glu | Pro | Leu | Gly | Val | Ala | Pro | Thr | Lys |
| | | | | 485 | | | | | 490 | | | | | 495 | |
| CTT | AGT | TAA | | | | | | | | | | | | | | 1497
| Leu | Ser | | | | | | | | | | | | | | |

( 2 ) INFORMATION FOR SEQ ID NO:4:

( i ) SEQUENCE CHARACTERISTICS:
        ( A ) LENGTH: 498 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Asp | Ala | Met | Lys | Arg | Gly | Leu | Cys | Cys | Val | Leu | Leu | Leu | Cys | Gly |
| 1 | | | | 5 | | | | 10 | | | | | 15 | | |
| Ala | Val | Phe | Val | Ser | Pro | Ser | Gln | Glu | Ile | His | Ala | Arg | Phe | Arg | Arg |
| | | | 20 | | | | 25 | | | | | 30 | | | |
| Gly | Ala | Arg | Ser | Met | Val | Pro | Val | Trp | Lys | Glu | Ala | Thr | Thr | Thr | Leu |
| | | | 35 | | | | 40 | | | | | 45 | | | |
| Phe | Cys | Ala | Ser | Asp | Ala | Lys | Ala | Tyr | Asp | Thr | Glu | Val | His | Asn | Val |
| | 50 | | | | | 55 | | | | | 60 | | | | |
| Trp | Ala | Thr | His | Ala | Cys | Val | Pro | Thr | Asp | Pro | Asn | Pro | Gln | Glu | Val |
| 65 | | | | | 70 | | | | | 75 | | | | | 80 |
| Val | Leu | Val | Asn | Val | Thr | Glu | Asn | Phe | Asn | Met | Trp | Lys | Asn | Asp | Met |
| | | | | 85 | | | | | 90 | | | | | 95 | |
| Val | Glu | Gln | Met | His | Glu | Asp | Ile | Ile | Ser | Leu | Trp | Asp | Gln | Ser | Leu |
| | | | 100 | | | | 105 | | | | | 110 | | | |
| Lys | Pro | Cys | Val | Lys | Leu | Thr | Pro | Leu | Cys | Val | Ser | Leu | Lys | Cys | Thr |
| | | 115 | | | | | 120 | | | | | 125 | | | |
| Asp | Leu | Lys | Asn | Asp | Thr | Asn | Thr | Asn | Ser | Ser | Ser | Gly | Arg | Met | Ile |
| | | 130 | | | | | 135 | | | | | 140 | | | |
| Met | Glu | Lys | Gly | Glu | Ile | Lys | Asn | Cys | Ser | Phe | Asn | Ile | Ser | Thr | Ser |
| 145 | | | | | 150 | | | | | 155 | | | | | 160 |

```
Ile  Arg  Gly  Lys  Val  Gln  Lys  Glu  Tyr  Ala  Phe  Phe  Tyr  Lys  Leu  Asp
               165                 170                      175

Ile  Ile  Pro  Ile  Asp  Asn  Asp  Thr  Thr  Ser  Tyr  Lys  Leu  Thr  Ser  Cys
               180                 185                      190

Asn  Thr  Ser  Val  Ile  Thr  Gln  Ala  Cys  Pro  Lys  Val  Ser  Phe  Glu  Pro
          195                      200                 205

Ile  Pro  Ile  His  Tyr  Cys  Ala  Pro  Ala  Gly  Phe  Ala  Ile  Leu  Lys  Cys
          210                      215                      220

Asn  Asn  Lys  Thr  Phe  Asn  Gly  Thr  Gly  Pro  Cys  Thr  Asn  Val  Ser  Thr
225                      230                      235                      240

Val  Gln  Cys  Thr  His  Gly  Ile  Arg  Pro  Val  Val  Ser  Thr  Gln  Leu  Leu
               245                      250                      255

Leu  Asn  Gly  Ser  Leu  Ala  Glu  Glu  Val  Val  Ile  Arg  Ser  Val  Asn
               260                      265                      270

Phe  Thr  Asp  Asn  Ala  Lys  Thr  Ile  Ile  Val  Gln  Leu  Asn  Thr  Ser  Val
          275                      280                      285

Glu  Ile  Asn  Cys  Thr  Arg  Pro  Asn  Asn  Asn  Thr  Arg  Lys  Arg  Ile  Arg
     290                      295                      300

Ile  Gln  Arg  Gly  Pro  Gly  Arg  Ala  Phe  Val  Thr  Ile  Gly  Lys  Ile  Gly
305                      310                      315                      320

Asn  Met  Arg  Gln  Ala  His  Cys  Asn  Ile  Ser  Arg  Ala  Lys  Trp  Asn  Asn
                    325                      330                      335

Thr  Leu  Lys  Gln  Ile  Ala  Ser  Lys  Leu  Arg  Glu  Gln  Phe  Gly  Asn  Asn
               340                      345                      350

Lys  Thr  Ile  Ile  Phe  Lys  Gln  Ser  Ser  Gly  Gly  Asp  Pro  Glu  Ile  Val
               355                      360                      365

Thr  His  Ser  Phe  Asn  Cys  Gly  Gly  Glu  Phe  Phe  Tyr  Cys  Asn  Ser  Thr
     370                      375                      380

Gln  Leu  Phe  Asn  Ser  Thr  Trp  Phe  Asn  Ser  Thr  Trp  Ser  Thr  Glu  Gly
385                      390                      395                      400

Ser  Asn  Asn  Thr  Glu  Gly  Ser  Asp  Thr  Ile  Thr  Leu  Pro  Cys  Arg  Ile
               405                      410                      415

Lys  Gln  Ile  Ile  Asn  Met  Trp  Gln  Lys  Val  Gly  Lys  Ala  Met  Tyr  Ala
               420                      425                      430

Pro  Pro  Ile  Ser  Gly  Gln  Ile  Arg  Cys  Ser  Ser  Asn  Ile  Thr  Gly  Leu
               435                      440                      445

Leu  Leu  Thr  Arg  Asp  Gly  Gly  Asn  Ser  Asn  Asn  Glu  Ser  Glu  Ile  Phe
     450                      455                      460

Arg  Pro  Gly  Gly  Gly  Asp  Met  Arg  Asp  Asn  Trp  Arg  Ser  Glu  Leu  Tyr
465                      470                      475                      480

Lys  Tyr  Lys  Val  Val  Lys  Ile  Glu  Pro  Leu  Gly  Val  Ala  Pro  Thr  Lys
               485                      490                      495

Leu  Ser
```

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "VH01 PCR primer"

( x i ) SEQUENCE DESCRIPTION: SEQ ID NO:5:

AGGTSMARCT GCAGSAGTCW GG　　　　　　　　　　　　　　　　　　　　　　　　22

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "VH02 PCR primer"

( x i ) SEQUENCE DESCRIPTION: SEQ ID NO:6:

TGAGGAGACG GTGACCGTGG TCCCTTGGCC CC　　　　　　　　　　　　　　　　32

( 2 ) INFORMATION FOR SEQ ID NO:7:

( i ) SEQUENCE CHARACTERISTICS:
        ( A ) LENGTH: 2755 base pairs
        ( B ) TYPE: nucleic acid
        ( C ) STRANDEDNESS: single
        ( D ) TOPOLOGY: circular ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "pNN03"

( x i ) SEQUENCE DESCRIPTION: SEQ ID NO:7:

```
TCGCGCGTTT CGGTGATGAC GGTGAAAACC TCTGACACAT GCAGCTCCCG GAGACGGTCA    60
CAGCTTGTCT GTAAGCGGAT GCCGGGAGCA GACAAGCCCG TCAGGGCGCG TCAGCGGGTG   120
TTGGCGGGTG TCGGGGCTGG CTTAACTATG CGGCATCAGA GCAGATTGTA CTGAGAGTGC   180
ACCATATGCG GTGTGAAATA CCGCACAGAT GCGTAAGGAG AAAATACCGC ATCAGGCGCC   240
ATTCGCCATT CAGGCTGCGC AACTGTTGGG AAGGGCGATC GGTGCGGGCC TCTTCGCTAT   300
TACGCCAGCT GGCGAAAGGG GGATGTGCTG CAAGGCGATT AAGTTGGGTA ACGCCAGGGT   360
TTTCCCAGTC ACGACGTTGT AAAACGACGG CCAGTGCCAA GCTAGCGGCC GCGGTCCAAC   420
CACCAATCTC AAAGCTTGGT ACCCGGGAAT TCAGATCTGC AGCATGCTCG AGCTCTAGAT   480
ATCGATTCCA TGGATCCTCA CATCCCAATC CGCGGCCGCA ATTCGTAATC ATGGTCATAG   540
CTGTTTCCTG TGTGAAATTG TTATCCGCTC ACAATTCCAC ACAACATACG AGCCGGAAGC   600
ATAAAGTGTA AAGCCTGGGG TGCCTAATGA GTGAGCTAAC TCACATTAAT TGCGTTGCGC   660
TCACTGCCCG CTTTCCAGTC GGGAAACCTG TCGTGCCAGC TGCATTAATG AATCGGCCAA   720
```

-continued

| | | | | | | |
|---|---|---|---|---|---|---|
| CGCGCGGGGA | GAGGCGGTTT | GCGTATTGGG | CGCTCTTCCG | CTTCCTCGCT | CACTGACTCG | 780 |
| CTGCGCTCGG | TCGTTCGGCT | GCGGCGAGCG | GTATCAGCTC | ACTCAAAGGC | GGTAATACGG | 840 |
| TTATCCACAG | AATCAGGGGA | TAACGCAGGA | AAGAACATGT | GAGCAAAAGG | CCAGCAAAAG | 900 |
| GCCAGGAACC | GTAAAAAGGC | CGCGTTGCTG | GCGTTTTCC | ATAGGCTCCG | CCCCCCTGAC | 960 |
| GAGCATCACA | AAAATCGACG | CTCAAGTCAG | AGGTGGCGAA | ACCCGACAGG | ACTATAAAGA | 1020 |
| TACCAGGCGT | TTCCCCCTGG | AAGCTCCCTC | GTGCGCTCTC | CTGTTCCGAC | CCTGCCGCTT | 1080 |
| ACCGGATACC | TGTCCGCCTT | TCTCCCTTCG | GGAAGCGTGG | CGCTTTCTCA | TAGCTCACGC | 1140 |
| TGTAGGTATC | TCAGTTCGGT | GTAGGTCGTT | CGCTCCAAGC | TGGGCTGTGT | GCACGAACCC | 1200 |
| CCCGTTCAGC | CCGACCGCTG | CGCCTTATCC | GGTAACTATC | GTCTTGAGTC | CAACCCGGTA | 1260 |
| AGACACGACT | TATCGCCACT | GGCAGCAGCC | ACTGGTAACA | GGATTAGCAG | AGCGAGGTAT | 1320 |
| GTAGGCGGTG | CTACAGAGTT | CTTGAAGTGG | TGGCCTAACT | ACGGCTACAC | TAGAAGAACA | 1380 |
| GTATTTGGTA | TCTGCGCTCT | GCTGAAGCCA | GTTACCTTCG | GAAAAAGAGT | TGGTAGCTCT | 1440 |
| TGATCCGGCA | AACAAACCAC | CGCTGGTAGC | GGTGGTTTTT | TTGTTTGCAA | GCAGCAGATT | 1500 |
| ACGCGCAGAA | AAAAGGATC | TCAAGAAGAT | CCTTTGATCT | TTTCTACGGG | GTCTGACGCT | 1560 |
| CAGTGGAACG | AAAACTCACG | TTAAGGGATT | TTGGTCATGA | GATTATCAAA | AAGGATCTTC | 1620 |
| ACCTAGATCC | TTTTAAATTA | AAAATGAAGT | TTTAAATCAA | TCTAAAGTAT | ATATGAGTAA | 1680 |
| ACTTGGTCTG | ACAGTTACCA | ATGCTTAATC | AGTGAGGCAC | CTATCTCAGC | GATCTGTCTA | 1740 |
| TTTCGTTCAT | CCATAGTTGC | CTGACTCCCC | GTCGTGTAGA | TAACTACGAT | ACGGGAGGGC | 1800 |
| TTACCATCTG | GCCCCAGTGC | TGCAATGATA | CCGCGAGACC | CACGCTCACC | GGCTCCAGAT | 1860 |
| TTATCAGCAA | TAAACCAGCC | AGCCGGAAGG | GCCGAGCGCA | GAAGTGGTCC | TGCAACTTTA | 1920 |
| TCCGCCTCCA | TCCAGTCTAT | TAATTGTTGC | CGGGAAGCTA | GAGTAAGTAG | TTCGCCAGTT | 1980 |
| AATAGTTTGC | GCAACGTTGT | TGCCATTGCT | ACAGGCATCG | TGGTGTCACG | CTCGTCGTTT | 2040 |
| GGTATGGCTT | CATTCAGCTC | CGGTTCCCAA | CGATCAAGGC | GAGTTACATG | ATCCCCCATG | 2100 |
| TTGTGCAAAA | AAGCGGTTAG | CTCCTTCGGT | CCTCCGATCG | TTGTCAGAAG | TAAGTTGGCC | 2160 |
| GCAGTGTTAT | CACTCATGGT | TATGGCAGCA | CTGCATAATT | CTCTTACTGT | CATGCCATCC | 2220 |
| GTAAGATGCT | TTTCTGTGAC | TGGTGAGTAC | TCAACCAAGT | CATTCTGAGA | ATAGTGTATG | 2280 |
| CGGCGACCGA | GTTGCTCTTG | CCCGGCGTCA | ATACGGGATA | ATACCGCGCC | ACATAGCAGA | 2340 |
| ACTTTAAAAG | TGCTCATCAT | TGGAAAACGT | TCTTCGGGGC | GAAAACTCTC | AAGGATCTTA | 2400 |
| CCGCTGTTGA | GATCCAGTTC | GATGTAACCC | ACTCGTGCAC | CCAACTGATC | TTCAGCATCT | 2460 |
| TTTACTTTCA | CCAGCGTTTC | TGGGTGAGCA | AAAACAGGAA | GGCAAAATGC | CGCAAAAAAG | 2520 |
| GGAATAAGGG | CGACACGGAA | ATGTTGAATA | CTCATACTCT | TCCTTTTTCA | ATATTATTGA | 2580 |
| AGCATTTATC | AGGGTTATTG | TCTCATGAGC | GGATACATAT | TTGAATGTAT | TTAGAAAAAT | 2640 |
| AAACAAATAG | GGGTTCCGCG | CACATTTCCC | CGAAAAGTGC | CACCTGACGT | CTAAGAAACC | 2700 |
| ATTATTATCA | TGACATTAAC | CTATAAAAAT | AGGCGTATCA | CGAGGCCCTT | TCGTC | 2755 |

( 2 ) INFORMATION FOR SEQ ID NO:8:

( i ) SEQUENCE CHARACTERISTICS:
        ( A ) LENGTH: 365 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: misc_feature
  ( B ) LOCATION: 1
  ( D ) OTHER INFORMATION: /note= "pMDR904 insert"

( x i ) SEQUENCE DESCRIPTION: SEQ ID NO:8:

| | | | | | |
|---|---|---|---|---|---|
| AGGTGAAGCT | GCAGGAGTCT | GGACCTGAAC | TGGTAAAGCC | TGGGGCTTCA | GTGAAGATGT | 60
| CCTGCAAGGC | TTCTGGATAC | ACATTCACTA | GCTATGTTAT | ACACTGGGTG | AGGCAGAAGC | 120
| CTGGGCAGGG | CCTTGACTGG | ATTGGATATA | TTAATCCTTA | CAATGATGGT | ACTGACTACG | 180
| ATGAGAAGTT | CAAAGGCAAG | GCCACACTGA | CTTCAGACAA | ATCCTCCAGC | ACAGCCTACA | 240
| TGGAGCTCAG | CAGCCTGACC | TCTGAGGACT | CTGCGGTCTA | TTACTGTGCA | AGAGAGAAGG | 300
| ATAACTACGC | GACGGGGGCC | TGGTTTGCTT | ACTGGGGCCA | AGGGACCACG | GTCACCGTCT | 360
| CCTCA | | | | | | 365

( 2 ) INFORMATION FOR SEQ ID NO:9:

( i ) SEQUENCE CHARACTERISTICS:
    ( A ) LENGTH: 366 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 1..366

( i x ) FEATURE:
    ( A ) NAME/KEY: misc_feature
    ( B ) LOCATION: 1
    ( D ) OTHER INFORMATION: /note= "5A8 heavy chain variable region"

( x i ) SEQUENCE DESCRIPTION: SEQ ID NO:9:

```
GAG  GTG  AAG  CTG  CAG  GAG  TCT  GGA  CCT  GAA  CTG  GTA  AAG  CCT  GGG  GCT        48
Glu  Val  Lys  Leu  Gln  Glu  Ser  Gly  Pro  Glu  Leu  Val  Lys  Pro  Gly  Ala
 1                   5                        10                       15

TCA  GTG  AAG  ATG  TCC  TGC  AAG  GCT  TCT  GGA  TAC  ACA  TTC  ACT  AGC  TAT        96
Ser  Val  Lys  Met  Ser  Cys  Lys  Ala  Ser  Gly  Tyr  Thr  Phe  Thr  Ser  Tyr
                    20                        25                       30

GTT  ATA  CAC  TGG  GTG  AGG  CAG  AAG  CCT  GGG  CAG  GGC  CTT  GAC  TGG  ATT       144
Val  Ile  His  Trp  Val  Arg  Gln  Lys  Pro  Gly  Gln  Gly  Leu  Asp  Trp  Ile
          35                        40                        45

GGA  TAT  ATT  AAT  CCT  TAC  AAT  GAT  GGT  ACT  GAC  TAC  GAT  GAG  AAG  TTC       192
Gly  Tyr  Ile  Asn  Pro  Tyr  Asn  Asp  Gly  Thr  Asp  Tyr  Asp  Glu  Lys  Phe
     50                        55                        60

AAA  GGC  AAG  GCC  ACA  CTG  ACT  TCA  GAC  AAA  TCC  TCC  AGC  ACA  GCC  TAC       240
Lys  Gly  Lys  Ala  Thr  Leu  Thr  Ser  Asp  Lys  Ser  Ser  Ser  Thr  Ala  Tyr
 65                       70                        75                       80

ATG  GAG  CTC  AGC  AGC  CTG  ACC  TCT  GAG  GAC  TCT  GCG  GTC  TAT  TAC  TGT       288
Met  Glu  Leu  Ser  Ser  Leu  Thr  Ser  Glu  Asp  Ser  Ala  Val  Tyr  Tyr  Cys
                    85                        90                       95

GCA  AGA  GAG  AAG  GAT  AAC  TAC  GCG  ACG  GGG  GCC  TGG  TTT  GCT  TAC  TGG       336
Ala  Arg  Glu  Lys  Asp  Asn  Tyr  Ala  Thr  Gly  Ala  Trp  Phe  Ala  Tyr  Trp
               100                      105                      110

GGC  CAA  GGG  ACC  ACG  GTC  ACC  GTC  TCC  TCA                                     366
```

Gly Gln Gly Thr Thr Val Thr Val Ser Ser
         115                 120

(2) INFORMATION FOR SEQ ID NO:10:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO:10:

Glu Val Lys Leu Gln Glu Ser Gly Pro Glu Leu Val Lys Pro Gly Ala
 1               5                  10                 15

Ser Val Lys Met Ser Cys Lys Ala Ser Gly Tyr Thr Phe Thr Ser Tyr
             20                  25                 30

Val Ile His Trp Val Arg Gln Lys Pro Gly Gln Gly Leu Asp Trp Ile
         35                  40                 45

Gly Tyr Ile Asn Pro Tyr Asn Asp Gly Thr Asp Tyr Asp Glu Lys Phe
     50                  55                 60

Lys Gly Lys Ala Thr Leu Thr Ser Asp Lys Ser Ser Thr Ala Tyr
 65                 70                  75                     80

Met Glu Leu Ser Ser Leu Thr Ser Glu Asp Ser Ala Val Tyr Tyr Cys
                 85                  90                 95

Ala Arg Glu Lys Asp Asn Tyr Ala Thr Gly Ala Trp Phe Ala Tyr Trp
         100                 105                110

Gly Gln Gly Thr Thr Val Thr Val Ser Ser
         115                 120

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "ACE149 PCR primer"

(xi) SEQUENCE DESCRIPTION: SEQ ID NO:11:

CTGGATATCG TAATGACCCA GTCTCCA        27

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature -continued ( B ) LOCATION: 1
    ( D ) OTHER INFORMATION: /note= "ACE150 PCR primer"

( x i ) SEQUENCE DESCRIPTION: SEQ ID NO:12:

GTTAGATCTC CAGCTTGGTC CC                                                22

( 2 ) INFORMATION FOR SEQ ID NO:13:

( i ) SEQUENCE CHARACTERISTICS:
    ( A ) LENGTH: 340 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "pMDR927 insert"

( x i ) SEQUENCE DESCRIPTION: SEQ ID NO:13:

CTGGATATCG TAATGACCCA GTCTCCATCC TCCCTAGCTG TGTCAGTTGG AGAGAAGGTT    60

ACTATGATCT GCAAGTCCAG TCAGAGCCTT TTATATAGTA CCAATCAAAA GAACTACTTG   120

GCCTGGTACC AGCAGAAACC AGGGCAGTCT CCTAAACTGC TGATTTACTG GGCATCCACT   180

AGGGAATCTG GGGTCCCTGA TCGCTTCACA GGCAGTGGAT CTGGGACAGA TTTCACTCTC   240

ACCATCAGCA GTGTGAAGGC TGAAGACCTG GCAGTTTATT ACTGTCAGCA ATATTATAGC   300

TATCGGACGT TCGGTGGAGG GACCAAGCTG GAGATCTAAC                     340

( 2 ) INFORMATION FOR SEQ ID NO:14:

( i ) SEQUENCE CHARACTERISTICS:
    ( A ) LENGTH: 336 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 1..336

( i x ) FEATURE:
    ( A ) NAME/KEY: misc_feature
    ( B ) LOCATION: 1
    ( D ) OTHER INFORMATION: /note= "5A8 light chain variable
      region"

( x i ) SEQUENCE DESCRIPTION: SEQ ID NO:14:

```
GAT  ATC  GTA  ATG  ACC  CAG  TCT  CCA  TCC  TCC  CTA  GCT  GTG  TCA  GTT  GGA       48
Asp  Ile  Val  Met  Thr  Gln  Ser  Pro  Ser  Ser  Leu  Ala  Val  Ser  Val  Gly
 1                  5                   10                      15

GAG  AAG  GTT  ACT  ATG  ATC  TGC  AAG  TCC  AGT  CAG  AGC  CTT  TTA  TAT  AGT       96
Glu  Lys  Val  Thr  Met  Ile  Cys  Lys  Ser  Ser  Gln  Ser  Leu  Leu  Tyr  Ser
             20                      25                      30

ACC  AAT  CAA  AAG  AAC  TAC  TTG  GCC  TGG  TAC  CAG  CAG  AAA  CCA  GGG  CAG      144
Thr  Asn  Gln  Lys  Asn  Tyr  Leu  Ala  Trp  Tyr  Gln  Gln  Lys  Pro  Gly  Gln
         35                      40                      45
```

| | | | | | | | | | | | | | | | | |
|---|---|---|---|---|---|---|---|---|---|---|---|---|---|---|---|---|
|TCT|CCT|AAA|CTG|CTG|ATT|TAC|TGG|GCA|TCC|ACT|AGG|GAA|TCT|GGG|GTC|192|
|Ser|Pro|Lys|Leu|Leu|Ile|Tyr|Trp|Ala|Ser|Thr|Arg|Glu|Ser|Gly|Val| |
| |50| | | |55| | | | |60| | | | | | |

| | | | | | | | | | | | | | | | | |
|---|---|---|---|---|---|---|---|---|---|---|---|---|---|---|---|---|
|CCT|GAT|CGC|TTC|ACA|GGC|AGT|GGA|TCT|GGG|ACA|GAT|TTC|ACT|CTC|ACC|240|
|Pro|Asp|Arg|Phe|Thr|Gly|Ser|Gly|Ser|Gly|Thr|Asp|Phe|Thr|Leu|Thr| |
|65| | | | |70| | | | |75| | | | |80| |

| | | | | | | | | | | | | | | | | |
|---|---|---|---|---|---|---|---|---|---|---|---|---|---|---|---|---|
|ATC|AGC|AGT|GTG|AAG|GCT|GAA|GAC|CTG|GCA|GTT|TAT|TAC|TGT|CAG|CAA|288|
|Ile|Ser|Ser|Val|Lys|Ala|Glu|Asp|Leu|Ala|Val|Tyr|Tyr|Cys|Gln|Gln| |
| | | | |85| | | | |90| | | | |95| | |

| | | | | | | | | | | | | | | | | |
|---|---|---|---|---|---|---|---|---|---|---|---|---|---|---|---|---|
|TAT|TAT|AGC|TAT|CGG|ACG|TTC|GGT|GGA|GGG|ACC|AAG|CTG|GAG|ATC|AAA|336|
|Tyr|Tyr|Ser|Tyr|Arg|Thr|Phe|Gly|Gly|Gly|Thr|Lys|Leu|Glu|Ile|Lys| |
| | | |100| | | | | |105| | | |110| | | |

(2) INFORMATION FOR SEQ ID NO:15:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:15:

| | | | | | | | | | | | | | | | |
|---|---|---|---|---|---|---|---|---|---|---|---|---|---|---|---|
|Asp|Ile|Val|Met|Thr|Gln|Ser|Pro|Ser|Ser|Leu|Ala|Val|Ser|Val|Gly|
|1| | | |5| | | | |10| | | | |15| |

| | | | | | | | | | | | | | | | |
|---|---|---|---|---|---|---|---|---|---|---|---|---|---|---|---|
|Glu|Lys|Val|Thr|Met|Ile|Cys|Lys|Ser|Ser|Gln|Ser|Leu|Leu|Tyr|Ser|
| | | |20| | | | |25| | | | |30| | |

| | | | | | | | | | | | | | | | |
|---|---|---|---|---|---|---|---|---|---|---|---|---|---|---|---|
|Thr|Asn|Gln|Lys|Asn|Tyr|Leu|Ala|Trp|Tyr|Gln|Gln|Lys|Pro|Gly|Gln|
| | |35| | | | |40| | | | |45| | | |

| | | | | | | | | | | | | | | | |
|---|---|---|---|---|---|---|---|---|---|---|---|---|---|---|---|
|Ser|Pro|Lys|Leu|Leu|Ile|Tyr|Trp|Ala|Ser|Thr|Arg|Glu|Ser|Gly|Val|
| |50| | | |55| | | | |60| | | | | |

| | | | | | | | | | | | | | | | |
|---|---|---|---|---|---|---|---|---|---|---|---|---|---|---|---|
|Pro|Asp|Arg|Phe|Thr|Gly|Ser|Gly|Ser|Gly|Thr|Asp|Phe|Thr|Leu|Thr|
|65| | | | |70| | | | |75| | | | |80|

| | | | | | | | | | | | | | | | |
|---|---|---|---|---|---|---|---|---|---|---|---|---|---|---|---|
|Ile|Ser|Ser|Val|Lys|Ala|Glu|Asp|Leu|Ala|Val|Tyr|Tyr|Cys|Gln|Gln|
| | | | |85| | | | |90| | | | |95| |

| | | | | | | | | | | | | | | | |
|---|---|---|---|---|---|---|---|---|---|---|---|---|---|---|---|
|Tyr|Tyr|Ser|Tyr|Arg|Thr|Phe|Gly|Gly|Gly|Thr|Lys|Leu|Glu|Ile|Lys|
| | | |100| | | | | |105| | | |110| | |

(2) INFORMATION FOR SEQ ID NO:16:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "312-56 PCR primer"

(xi) SEQUENCE DESCRIPTION: SEQ ID NO:16:

GTGCAGCTGC AGGAGTCTGG AGCTGAAGTG AAAAAGCCTG GGGCTTCAGT GAAGGTGT    58

(2) INFORMATION FOR SEQ ID NO:17:

(i) SEQUENCE CHARACTERISTICS:
        (A) LENGTH: 49 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (ix) FEATURE:
(A) NAME/KEY: misc_feature
(B) LOCATION: 1
(D) OTHER INFORMATION: /note= "312-57 PCR primer"

(xi) SEQUENCE DESCRIPTION: SEQ ID NO:17:

AGGATTAATA TATCCAATCC ACTCAAGGCC CTGCCCAGGC GCCTGCCTC    49

(2) INFORMATION FOR SEQ ID NO:18:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: misc_feature
(B) LOCATION: 1
(D) OTHER INFORMATION: /note= "312-58 PCR primer"

(xi) SEQUENCE DESCRIPTION: SEQ ID NO:18:

TGGGTGAGGC AGGCGCCTGG GCAGGGCCTT GAGTGGATTG GATATAT    47

(2) INFORMATION FOR SEQ ID NO:19:

(i) SEQUENCE CHARACTERISTICS:
(A) LENGTH: 75 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: misc_feature
(B) LOCATION: 1
(D) OTHER INFORMATION: /note= "312-59 PCR primer"

(xi) SEQUENCE DESCRIPTION: SEQ ID NO:19:

GACCGCAGTG TCCTCAGACC TCAGGCTGCT GAGCTCCATG TAGGCTGTGT TGGTGGATGG    60

GTCTAAAGTC ACTGT    75

(2) INFORMATION FOR SEQ ID NO:20:

(i) SEQUENCE CHARACTERISTICS:
(A) LENGTH: 75 base pairs
(B) TYPE: nucleic acid
(C) STRANDEDNESS: single
(D) TOPOLOGY: linear (ii) MOLECULE TYPE: cDNA (iii) HYPOTHETICAL: NO ( i v ) ANTI-SENSE: NO ( i x ) FEATURE:
- ( A ) NAME/KEY: misc_feature
- ( B ) LOCATION: 1
- ( D ) OTHER INFORMATION: /note= "312-60 PCR primer"

( x i ) SEQUENCE DESCRIPTION: SEQ ID NO:20:

```
AGGCCACAGT GACTTTAGAC CCATCCACCA ACACAGCCTA CATGGAGCTC AGCAGCCTGA      60
GGTCTGAGGA CACTG                                                       75
```

( 2 ) INFORMATION FOR SEQ ID NO:21:

( i ) SEQUENCE CHARACTERISTICS:
- ( A ) LENGTH: 55 base pairs
- ( B ) TYPE: nucleic acid
- ( C ) STRANDEDNESS: single
- ( D ) TOPOLOGY: linear ( i i ) MOLECULE TYPE: cDNA ( i i i ) HYPOTHETICAL: NO ( i v ) ANTI-SENSE: NO ( i x ) FEATURE:
- ( A ) NAME/KEY: misc_feature
- ( B ) LOCATION: 1
- ( D ) OTHER INFORMATION: /note= "312-61 PCR primer"

( x i ) SEQUENCE DESCRIPTION: SEQ ID NO:21:

```
AGACGGTGAC CAGGGTCCCT TGGCCCCAGT AAGCAAACCA GGCCCCCGTC GCGTA           55
```

( 2 ) INFORMATION FOR SEQ ID NO:22:

( i ) SEQUENCE CHARACTERISTICS:
- ( A ) LENGTH: 331 base pairs
- ( B ) TYPE: nucleic acid
- ( C ) STRANDEDNESS: single
- ( D ) TOPOLOGY: linear ( i i ) MOLECULE TYPE: cDNA ( i i i ) HYPOTHETICAL: NO ( i v ) ANTI-SENSE: NO ( i x ) FEATURE:
- ( A ) NAME/KEY: misc_feature
- ( B ) LOCATION: 1
- ( D ) OTHER INFORMATION: /note= "pMDR989-15 insert"

( x i ) SEQUENCE DESCRIPTION: SEQ ID NO:22:

```
AAGTGAAAAA GCCTGGGGCT TCAGTGAAGG TGTCCTGCAA GGCTTCTGGA TACACATTCA      60
CTAGCTATGT TATACACTGG GTGAGGCAGA AGCCTGGGCA GGGCCTTGAC TGGATTGGAT     120
ATATTAATCC TTACAATGAT GGTACTGACT ACGATGAGAA GTTCAAAGGC AAGGCCACAC     180
TGACTTCAGA CAAATCCTCC AGCACAGCCT ACATGGAGCT CAGCAGCCTG ACCTCTGAGG     240
ACTCTGCGGT CTATTACTGT GCAAGAGAGA AGGATAACTA CGCGACGGGG GCCTGGTTTG     300
CTTACTGGGG CCAAGGGACT GGTCACCGTC T                                    331
```

( 2 ) INFORMATION FOR SEQ ID NO:23:

( i ) SEQUENCE CHARACTERISTICS:
- ( A ) LENGTH: 358 base pairs
- ( B ) TYPE: nucleic acid
- ( C ) STRANDEDNESS: single
- ( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: misc_feature
  ( B ) LOCATION: 1
  ( D ) OTHER INFORMATION: /note= "pMDR991 insert"

( x i ) SEQUENCE DESCRIPTION: SEQ ID NO:23:

| | | | | | | |
|---|---|---|---|---|---|---|
| GTGCAGCTGC | AGGAGTCTGG | AGCTGAAGTG | AAAAAGCCTG | GGGCTTCAGT | GAAGGTGTCC | 60 |
| TGCAAGGCTT | CTGGATACAC | ATTCACTAGC | TATGTTATAC | ACTGGGTGAG | GCAGGCGCCT | 120 |
| GGGCAGGGCC | TTGAGTGGAT | TGGATATATT | AATCCTTACA | ATGATGGTAC | TGACTACGAT | 180 |
| GAGAAGTTCA | AAGGCAAGGC | CACAGTGACT | TTAGACCCAT | CCACCAACAC | AGCCTACATG | 240 |
| GAGCTCAGCA | GCCTGAGGTC | TGAGGACACT | GCGGTCTATT | ACTGTGCAAG | AGAGAAGGAT | 300 |
| AACTACGCGA | CGGGGGCCTG | GTTTGCTTAC | TGGGGCCAAG | GGACCCTGGT | CACCGTCT | 358 |

( 2 ) INFORMATION FOR SEQ ID NO:24:

( i ) SEQUENCE CHARACTERISTICS:
    ( A ) LENGTH: 66 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "312-62 oligonucleotide"

( x i ) SEQUENCE DESCRIPTION: SEQ ID NO:24:

| | | | | | | |
|---|---|---|---|---|---|---|
| GTACCCCTGG | ATATCGTAAT | GACCCAGTCT | CCAGACTCCC | TAGCTGTGTC | ACTTGGAGAG | 60 |
| AGGGCT | | | | | | 66 |

( 2 ) INFORMATION FOR SEQ ID NO:25:

( i ) SEQUENCE CHARACTERISTICS:
    ( A ) LENGTH: 62 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "312-63 oligonucleotide"

( x i ) SEQUENCE DESCRIPTION: SEQ ID NO:25:

| | | | | | | |
|---|---|---|---|---|---|---|
| ACTATAAACT | GCAAGTCCAG | TGGGAGCCTT | TTATATAGTA | CCAATCCAAA | GAACTACTTG | 60 |
| GC | | | | | | 62 |

( 2 ) INFORMATION FOR SEQ ID NO:26:

( i ) SEQUENCE CHARACTERISTICS:
    ( A ) LENGTH: 69 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "312-64 oligonucleotide"

( x i ) SEQUENCE DESCRIPTION: SEQ ID NO:26:

CTGGTACCAG CAGAAACCAG GGCAGCCTCC TAAACTGCTG ATTTACTGGG CATCCACTAG        60

GGAATCTGG                                                                69

( 2 ) INFORMATION FOR SEQ ID NO:27:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "312-65 oligonucleotide"

( x i ) SEQUENCE DESCRIPTION: SEQ ID NO:27:

GGTCCCTGAT CGCTTCTCAG GCAGTGGATC TGGGACAGAT TTCACTCTCA CCATCAGCAG        60

TTTGCAGGCT GA                                                            72

( 2 ) INFORMATION FOR SEQ ID NO:28:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "312-66 oligonucleotide"

( x i ) SEQUENCE DESCRIPTION: SEQ ID NO:28:

AGACGTGGCA GTTTATTACT GTCAGCAATA TTATAGCTAT CGGACGTTCG GTCAAGGGAC        60

CAAGCTGGA                                                                69

( 2 ) INFORMATION FOR SEQ ID NO:29:

( i ) SEQUENCE CHARACTERISTICS:
        ( A ) LENGTH: 67 base pairs (B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: misc_feature
(B) LOCATION: 1
(D) OTHER INFORMATION: /note= "312-67 oligonucleotide"

(xi) SEQUENCE DESCRIPTION: SEQ ID NO:29:

```
GATCTCCAGC TTGGTCCCTT GACCGAACGT CCGATAGCTA TAATATTGCT GACAGTAATA      60
AACTGCC                                                                67
```

(2) INFORMATION FOR SEQ ID NO:30:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: misc_feature
(B) LOCATION: 1
(D) OTHER INFORMATION: /note= "312-68 oligonucleotide"

(xi) SEQUENCE DESCRIPTION: SEQ ID NO:30:

```
ACGTCTTCAG CCTGCAAACT GCTGATGGTG AGAGTGAAAT CTGTCCCAGA TCCACTGCCT      60
GAGAAGCGAT C                                                           71
```

(2) INFORMATION FOR SEQ ID NO:31:

(i) SEQUENCE CHARACTERISTICS:
(A) LENGTH: 69 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: misc_feature
(B) LOCATION: 1
(D) OTHER INFORMATION: /note= "312-69 oligonucleotide"

(xi) SEQUENCE DESCRIPTION: SEQ ID NO:31:

```
AGGGACCCCA GATTCCCTAG TGGATGCCCA GTAAATCAGC AGTTTAGGAG GCTGCCCTGG      60
TTTCTGCTG                                                              69
```

(2) INFORMATION FOR SEQ ID NO:32:

(i) SEQUENCE CHARACTERISTICS:
(A) LENGTH: 63 base pairs
(B) TYPE: nucleic acid
(C) STRANDEDNESS: single ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "312-70 oligonucleotide"

( x i ) SEQUENCE DESCRIPTION: SEQ ID NO:32:

```
GTACCAGGCC AAGTAGTTCT TTTGATTGGT ACTATATAAA AGGCTCCCAC TGGACTTGCA    60

GTT                                                                  63
```

( 2 ) INFORMATION FOR SEQ ID NO:33:

( i ) SEQUENCE CHARACTERISTICS:
    ( A ) LENGTH: 68 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "312-71 oligonucleotide"

( x i ) SEQUENCE DESCRIPTION: SEQ ID NO:33:

```
TATAGTAGCC CTCTCTCCAA GTGACACAGC TAGGGAGTCT GGAGACTGGG TCATTACGAT    60

ATCCAGGG                                                             68
```

( 2 ) INFORMATION FOR SEQ ID NO:34:

( i ) SEQUENCE CHARACTERISTICS:
    ( A ) LENGTH: 344 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "pMDR1003 insert"

( x i ) SEQUENCE DESCRIPTION: SEQ ID NO:34:

```
GGTACCCCTG GATATCGTAA TGACCCAGTC TCCAGACTCC CTAGCTGTGT CACTTGGAGA    60

GAGGGCTACT ATAAACTGCA AGTCCAGTGG GAGCCTTTTA TATAGTACCA ATCAAAAGAA   120

CTACTTGGCC TGGTACCAGC AGAAACCAGG GCAGCCTCCT AAACTGCTGA TTTACTGGGC   180

ATCCACTAGG GAATCTGGGG TCCCTGATCG CTTCTCAGGC AGTGGATCTG GGACAGATTT   240

CACTCTCACC ATCAGCAGTT TGCAGGCTGA AGACGTGGCA GTTTATTACT GTCAGCAATA   300

TTATAGCTAT CGGACGTTCG GTCGAGGGAC CAAGCTGGAG ATCT                    344
```

( 2 ) INFORMATION FOR SEQ ID NO:35:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "312-45 oligonucleotide"

( x i ) SEQUENCE DESCRIPTION: SEQ ID NO:35:

```
GTACCGCGGC CGCACCATGG ACTGGACCTG GAGGGTCTTC TGCTTGCTGG C          51
```

( 2 ) INFORMATION FOR SEQ ID NO:36:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "312-50 oligonucleotide"

( x i ) SEQUENCE DESCRIPTION: SEQ ID NO:36:

```
GATCCAAGCT TAGGACTCAC CTGAGGAGAC GGTGACCCTC GAGG                  44
```

( 2 ) INFORMATION FOR SEQ ID NO:37:

( i ) SEQUENCE CHARACTERISTICS:
    ( A ) LENGTH: 144 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "pLCB6 insert"

( x i ) SEQUENCE DESCRIPTION: SEQ ID NO:37:

```
GTACCGCGGC CGCACCATGG ACTGGACCTG GAGGGTCTTC TGCTTGCTGG CTGTAGCACC  60
AGGTGCCCAC TCCCAGGTCC AACTGCAGTC TAGAGTCGAC CTCGAGGGTC ACCGTCTCCT 120
CAGGTGAGTC CTAAGCTTGG ATCC                                       144
```

( 2 ) INFORMATION FOR SEQ ID NO:38:

( i ) SEQUENCE CHARACTERISTICS:
    ( A ) LENGTH: 461 base pairs (B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: misc_feature
(B) LOCATION: 1
(D) OTHER INFORMATION: /note= "pLCB7 insert"

(xi) SEQUENCE DESCRIPTION: SEQ ID NO:38:

| | | | | | | |
|---|---|---|---|---|---|---|
| GTACCGCGGC | CGCACCATGG | ACTGGACCTG | GAGGGTCTTC | TGCTTGCTGG | CTGTAGCACC | 60 |
| AGGTGCCCAC | TCCCAGGTCC | AACTGCAGGA | GTCTGGACCT | GAACTGGTAA | AGCCTGGGGC | 120 |
| TTCAGTGAAG | ATGTCCTGCA | AGGCTTCTGG | ATACACATTC | ACTAGCTATG | TTATACACTG | 180 |
| GGTGAGGCAG | AAGCCTGGGC | AGGGCCTTGA | CTGGATTGGA | TATATTAATC | CTTACAATGA | 240 |
| TGGTACTGAC | TACGATGAGA | AGTTCAAAGG | CAAGGCCACA | CTGACTTCAG | ACAAATCCTC | 300 |
| CAGCACAGCC | TACATGGAGC | TCAGCAGCCT | GACCTCTGAG | GACTCTGCGG | TCTATTACTG | 360 |
| TGCAAGAGAG | AAGGATAACT | ACGCGACGGG | GGCCTGGTTT | GCTTACTGGG | GCCAAGGGAC | 420 |
| CACGGTCACC | GTCTCCTCAG | GTGAGTCCTA | AGCTTGGATC | C | | 461 |

(2) INFORMATION FOR SEQ ID NO:39:

(i) SEQUENCE CHARACTERISTICS:
(A) LENGTH: 461 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: misc_feature
(B) LOCATION: 1
(D) OTHER INFORMATION: /note= "pMDR1001 insert"

(xi) SEQUENCE DESCRIPTION: SEQ ID NO:39:

| | | | | | | |
|---|---|---|---|---|---|---|
| GTACCGCGGC | CGCACCATGG | ACTGGACCTG | GAGGGTCTTC | TGCTTGCTGG | CTGTAGCACC | 60 |
| AGGTGCCCAC | TCCCAGGTCC | AACTGCAGGA | GTCTGGAGCT | GAAGTGAAAA | AGCCTGGGGC | 120 |
| TTCAGTGAAG | GTGTCCTGCA | AGGCTTCTGG | ATACACATTC | ACTAGCTATG | TTATACACTG | 180 |
| GGTGAGGCAG | GCGCCTGGGC | AGGGCCTTGA | GTGGATTGGA | TATATTAATC | CTTACAATGA | 240 |
| TGGTACTGAC | TACGATGAGA | AGTTCAAAGG | CAAGGCCACA | GTGACTTTAG | ACCCATCCAC | 300 |
| CAACACAGCC | TACATGGAGC | TCAGCAGCCT | GAGGTCTGAG | GACACTGCGG | TCTATTACTG | 360 |
| TGCAAGAGAG | AAGGATAACT | ACGCGACGGG | GGCCTGGTTT | GCTTACTGGG | GCCAAGGGAC | 420 |
| CCTGGTCACC | GTCTCCTCAG | GTGAGTCCTA | AGCTTGGATC | C | | 461 |

(2) INFORMATION FOR SEQ ID NO:40:

(i) SEQUENCE CHARACTERISTICS:
(A) LENGTH: 7892 base pairs
(B) TYPE: nucleic acid
(C) STRANDEDNESS: single
(D) TOPOLOGY: circular (ii) MOLECULE TYPE: cDNA (iii) HYPOTHETICAL: NO (iv) ANTI-SENSE: NO (ix) FEATURE:
    (A) NAME/KEY: misc_feature
    (B) LOCATION: 1
    (D) OTHER INFORMATION: /note= "pSAB132"

(xi) SEQUENCE DESCRIPTION: SEQ ID NO:40:

| | | | | | | |
|---|---|---|---|---|---|---|
| GAATTCGAGC | TTGCATGCCT | GCAGGTCGTT | ACATAACTTA | CGGTAAATGG | CCCGCCTGGC | 60 |
| TGACCGCCCA | ACGACCCCCG | CCCATTGACG | TCAATAATGA | CGTATGTTCC | CATAGTAACG | 120 |
| CCAATAGGGA | CTTTCCATTG | ACGTCAATGG | GTGGAGTATT | TACGGTAAAC | TGCCCACTTG | 180 |
| GCAGTACATC | AAGTGTATCA | TATGCCAAGT | ACGCCCCTA | TTGACGTCAA | TGACGGTAAA | 240 |
| TGGCCCGCCT | GGCATTATGC | CCAGTACATG | ACCTTATGGG | ACTTTCCTAC | TTGGCAGTAC | 300 |
| ATCTACGTAT | TAGTCATCGC | TATTACCATG | GTGATGCGGT | TTTGGCAGTA | CATCAATGGG | 360 |
| CGTGGATAGC | GGTTTGACTC | ACGGGGATTT | CCAAGTCTCC | ACCCCATTGA | CGTCAATGGG | 420 |
| AGTTTGTTTT | GGCACCAAAA | TCAACGGGAC | TTTCCAAAAT | GTCGTAACAA | CTCCGCCCCA | 480 |
| TTGACGCAAA | TGGGCGGTAG | GCGTGTACGG | TGGGAGGTCT | ATATAAGCAG | AGCTCGTTTA | 540 |
| GTGAACCGTC | AGATCGCCTG | GAGACGCCAT | CCACGCTGTT | TTGACCTCCA | TAGAAGACAC | 600 |
| CGGGACCGAT | CCAGCCTCCG | GACTCTAGAG | GATCCGGTAC | TCGAGGAACT | GAAAAACCAG | 660 |
| AAAGTTAACT | GGTAAGTTTA | GTCTTTTTGT | CTTTTATTTC | AGGTCCCGGA | TCCGGTGGTG | 720 |
| GTGCAAATCA | AGAACTGCT | CCTCAGTGGA | TGTTGCCTTT | ACTTCTAGGC | CTGTACGAA | 780 |
| GTGTTACTTC | TGCTCTAAAA | GCTGCGGAAT | TGTACCCGCG | GCCGCGTCGA | CCGTGACCCC | 840 |
| TGCGCCGCGC | GGACTCCTGC | CCCGAGGGTC | CGGACGCGCC | CCAGCTCGCG | CCCCTTCCCA | 900 |
| TATTTATTCG | GACCCCAAGC | ATCGCCCCAA | TAAAGACCAG | CAAGCAACCG | GCTGGGGTGT | 960 |
| CCGTGCGTGT | TAGGGGGCCC | GTGGGACCTC | CCTTGCCGTC | TCTCCTCGCG | CACGGCCCGG | 1020 |
| GTCCGCCCTG | TAGCGCTCGC | TGTCTCTCCC | CTGCCTGAAG | CGCCCCACCA | CCGTCTTTCA | 1080 |
| GGCCCCGGAC | TTGGTGCCGG | GTCCAGGCGT | AAAGGAGCAG | GTGACTCTGC | AGCACTCGCT | 1140 |
| TTATTTCGCC | AGAGTCGCGG | GGCGTCCAGA | AGGGGCCCCT | GGACTCCGGC | GCGGGGCCGG | 1200 |
| CTCAGTCCCG | CCCCTTGCCT | GCGCGGAGCT | TCTGGCGACT | CCCAGGCCGC | TGCTCCTCGT | 1260 |
| CGGGACGCCT | CGGGGACACC | CAGGCCTGCT | TCTTCCTGGG | CTCGGCGTCC | CTGGAGTCCC | 1320 |
| GTGCCCACGG | CCGGTGGCCC | CCTTCGCGTG | ACTCCCAGCG | CTGGGGTAGG | GCTTCCCGGG | 1380 |
| GCTCCCTGGC | GGCCCGTGGC | CTCTCCTCTT | TCCGCGGCCT | CTCTTTCTTA | GGTCTCTCCT | 1440 |
| CCTTCCGCGG | CTTCTCCTTC | CGCGGCTTCC | CCTCTCTCCG | AGGCCTCTCC | TTGGGTCCCC | 1500 |
| GGTCTGCGAG | GGTCACACGG | TCCTCCCGGA | CGGCCTCTCC | GGTGGCCTCG | CCGGGCTCCT | 1560 |
| CTTCGTCGTT | CTCTGCAGCC | TCCCGACTCC | CGGGAATCTT | GGGTCTGACC | TCTGCCTCGG | 1620 |
| CCCGGGGCGC | AGGCGGCGCT | GATGGAGGCG | CCTGGGCCTC | GAACTTAGGC | TGCAAGACAG | 1680 |
| AGTGGGGTCC | TGGGGTAAGC | GCCCACCTTC | CCCCGGCCC | GGGCTCCTTC | TTTCCTTGGG | 1740 |
| GATGAAGGTC | CCAATGCCCG | CGGTCAGTGG | AAGGAAGCTC | TTACCAGGGG | CGACGATGGC | 1800 |
| TCCCTCGGGG | CTGAGCTTGG | CGGGACCCAG | GGCTCGGGCA | CACGTGCTTG | GAGTGCTGCC | 1860 |
| TCCGCAGGGA | CGGCGTCTGC | AGCGACAGGG | TCGGGACCCG | AGTCAGCTGG | GCCGAGGCAC | 1920 |
| GGTCCACACT | GTCCATCCCT | CCCTCACCCC | TAGAGCCCCC | CTCCCTGGAC | AGTTGGAGTG | 1980 |
| GGGCTCCCCC | GGTACGGCTG | AGACTAAGGA | TGCCCCCGAG | CCGTGGGAAG | GGACTCCGGG | 2040 |

```
ACTCCGCTGC CGCGGCGCCC CTTCTCCGAA CCTCGCTCTT TCAATTGGTC ATTCTTCCCC    2100
CCGACCACGG GCTGTAGGAG GCCCCTAGCA AGGGAGGGGT CGCAGGAGTG CCCCCGGGGG    2160
GCGCTCACGA GCTGAGCGGT CCCCAGAGAG GGCGCAGGGG AAAGGCGGCA GAACGCTACG    2220
AGGCAGGAGG GGTTGCACAA GGTTCATCCG GAAGCCAGAA CCTACTCGCG GCGAGGGGAA    2280
TGGGCCCCGC AAAAGGTCCA CACCGGGTGA GAGGGCGCG CAAGGCCCGT CACTTAAGGG     2340
ACATATGACG TGAGCTCAGA TCTTTGTGAA GGAACCTTAC TTCTGTGGTG TGACATAATT    2400
GGACAAACTA CCTACAGAGA TTTAAAGCTC TAAGGTAAAT ATAAAATTTT TAAGTGTATA    2460
ATGTGTTAAA CTACTGATTC TAATTGTTTG TGTATTTTAG ATTCCAACCT ATGGAACTGA    2520
TGAATGGGAG CAGTGGTGGA ATGCCTTTAA TGAGGAAAAC CTGTTTGCT CAGAAGAAAT     2580
GCCATCTAGT GATGATGAGG CTACTGCTGA CTCTCAACAT TCTACTCCTC CAAAAAGAA    2640
GAGAAAGGTA GAAGACCCCA AGGACTTTCC TTCAGAATTG CTAAGTTTTT TGAGTCATGC    2700
TGTGTTTAGT AATAGAACTC TTGCTTGCTT TGCTATTTAC ACCACAAAGG AAAAAGCTGC    2760
ACTGCTATAC AAGAAAATTA TGGAAAAATA TTCTGTAACC TTTATAAGTA GGCATAACAG    2820
TTATAATCAT AACATACTGT TTTTTCTTAC TCCACACAGG CATAGAGTGT CTGCTATTAA    2880
TAACTATGCT CAAAAATTGT GTACCTTTAG CTTTTTAATT TGTAAAGGGG TTAATAAGGA    2940
ATATTTGATG TATAGTGCCT TGACTAGAGA TCATAATCAG CCATACCACA TTTGTAGAGG    3000
TTTTACTTGC TTTAAAAAAC CTCCCACACC TCCCCCTGAA CCTGAAACAT AAAATGAATG    3060
CAATTGTTGT TGTTAACTTG TTTATTGCAG CTTATAATGG TTACAAATAA AGCAATAGCA    3120
TCACAAATTT CACAAATAAA GCATTTTTTT CACTGCATTC TAGTTGTGGT TTGTCCAAAC    3180
TCATCAATGT ATCTTATCAT GTCTGGATCC TCTACGCCGG ACGCATCGTG GCCGGCATCA    3240
CCGGCGCCAC AGGTGCGGTT GCTGGCGCCT ATATCGCCGA CATCACCGAT GGGGAAGATC    3300
GGGCTCGCCA CTTCGGGCTC ATGAGCGCTT GTTTCGGCGT GGGTATGGTG CAGGCCCCG    3360
TGGCCGGGGG ACTGTTGGGC GCCATCTCCT TGCATGCACC ATTCCTTGCG GCGGCGGTGC    3420
TCAACGGCCT CAACCTACTA CTGGGCTGCT TCCTAATGCA GGAGTCGCAT AAGGGAGAGC    3480
GTCGAGACTC CATCTCAAAA ATAAATAAA ATAAAATTA AAAAAAAGG GCCCTTGTGC       3540
AAAGCTGACA GCTTGTATGT TTCTGCTGTT GACATTTGTG GGCTGTTTAC CAACACTTCT    3600
GGAACACAGC AGTGGAAGGG ACTTCCCAGA TATTTTAAAA TTACCCTTAG AAAGCGGTCT    3660
GTGAAAAACC CCTACCCAAT TTCCTTTTTG TTAAGTGACC TAATTAACAG GAGGACACAG    3720
AGGGTGGATG GGCAGCCTAT GATTGGAATG TCCTCTCAAG TAGAGGAGGT TAGGGTTTAT    3780
GAGGACACAG AGGAGCTTCC TGGGGATCCA GACATGATAA GATACATTGA TGAGTTTGGA    3840
CAAACCACAA CTAGAATGCA GTGAAAAAAA TGCTTTATTT GTGAAATTTG TGATGCTATT    3900
GCTTTATTTG TAACCATTAT AAGCTGCAAT AAACAAGTTA ACAACAACAA TTGCATTCAT    3960
TTTATGTTTC AGGTTCAGGG GGAGGTGTGG GAGGTTTTTT AAAGCAAGTA AAACCTCTAC    4020
AAATGTGGTA TGGCTGATTA TGATCTCTAG TCAAGGCACT ATACATCAAA TATTCCTTAT    4080
TAACCCCTTT ACAAATTAAA AAGCTAAAGG TACACAATTT TTGAGCATAG TTATTAATAG    4140
CAGACACTCT ATGCCTGTGT GGAGTAAGAA AAAACAGTAT GTTATGATTA TAACTGTTAT    4200
GCCTACTTAT AAAGGTTACA GAATATTTTT CCATAATTTT CTTGTATAGC AGTGCAGCTT    4260
TTTCCTTTGT GGTGTAAATA GCAAAGCAAG CAAGAGTTCT ATTACTAAAC ACAGCATGAC    4320
TCAAAAAACT TAGCAATTCT GAAGGAAAGT CCTTGGGGTC TTCTACCTTT CTCTTCTTTT    4380
TTGGAGGAGT AGAATGTTGA GAGTCAGCAG TAGCCTCATC ATCACTAGAT GGCATTTCTT    4440
```

```
CTGAGCAAAA CAGGTTTTCC TCATTAAAGG CATTCCACCA CTGCTCCCAT TCATCAGTTC    4500

CATAGGTTGG AATCTAAAAT ACACAAACAA TTAGAATCAG TAGTTTAACA CATTATACAC    4560

TTAAAAATTT TATATTTACC TTAGAGCTTT AAATCTCTGT AGGTAGTTTG TCCAATTATG    4620

TCACACCACA GAAGTAAGGT TCCTTCACAA AGATCTAAAG CCAGCAAAAG TCCCATGGTC    4680

TTATAAAAAT GCATAGCTTT AGGAGGGGAG CAGAGAACTT GAAAGCATCT TCCTGTTAGT    4740

CTTTCTTCTC GTAGACTTCA AACTTATACT TGATGCCTTT TTCCTCCTGG ACCTCAGAGA    4800

GGACGCCTGG GTATTCTGGG AGAAGTTTAT ATTTCCCCAA ATCAATTTCT GGGAAAAACG    4860

TGTCACTTTC AAATTCCTGC ATGATCCTTG TCACAAAGAG TCTGAGGTGG CCTGGTTGAT    4920

TCATGGCTTC CTGGTAAACA GAACTGCCTC CGACTATCCA AACCATGTCT ACTTTACTTG    4980

CCAATTCCGG TTGTTCAATA AGTCTTAAGG CATCATCCAA ACTTTTGGCA AGAAAATGAG    5040

CTCCTCGTGG TGGTTCTTTG AGTTCTCTAC TGAGAACTAT ATTAATTCTG TCCTTTAAAG    5100

GTCGATTCTT CTCAGGAATG GAGAACCAGG TTTTCCTACC CATAATCACC AGATTCTGTT    5160

TACCTTCCAC TGAAGAGGTT GTGGTCATTC TTTGGAAGTA CTTGAACTCG TTCCTGAGCG    5220

GAGGCCAGGG TAGGTCTCCG TTCTTGCCAA TCCCCATATT TTGGGACACG GCGACGATGC    5280

AGTTCAATGG TCGAACCATG ATGGCAGCGG GGATAAAATC CTACCAGCCT TCACGCTAGG    5340

ATTGCCGTCA AGTTTGGCGC GAAATCGCAG CCCTGAGCTG TCCCCCCCCC CAAGCTTTTT    5400

GCAAAGCCT AGGCCTCCAA AAAAGCCTCC TCACTACTTC TGGAATAGCT CAGAGGCCGA    5460

GGCGGCCTCG GCCTCTGCAT AAATAAAAAA AATTAGTCAG CCATGGGGCG GAGAATGGGC    5520

GGAACTGGGC GGAGTTAGGG GCGGGATGGG CGGAGTTAGG GGCGGGACTA TGGTTGCTGA    5580

CTAATTGAGA TGCTGCCTCG CGCGTTTCGG TGATGACGGT GAAAACCTCT GACACATGCA    5640

GCTCCCGGAG ACGGTCACAG CTTGTCTGTA AGCGGATGCC GGGAGCAGAC AAGCCCGTCA    5700

GGGCGCGTCA GCGGGTGTTG GCGGGTGTCG GGGCGCAGCC ATGACCCAGT CACGTAGCGA    5760

TAGCGGAGTG TATACTGGCT TAACTATGCG GCATCAGAGC AGATTGTACT GAGAGTGCAC    5820

CATATGCGGT GTGAAATACC GCACAGATGC GTAAGGAGAA AATACCGCAT CAGGCGCTCT    5880

TCCGCTTCCT CGCTCACTGA CTCGCTGCGC TCGGTCGTTC GGCTGCGGCG AGCGGTATCA    5940

GCTCACTCAA AGGCGGTAAT ACGGTTATCC ACAGAATCAG GGGATAACGC AGGAAAGAAC    6000

ATGTGAGCAA AAGGCCAGCA AAAGGCCAGG AACCGTAAAA AGGCCGCGTT GCTGGCGTTT    6060

TTCCATAGGC TCCGCCCCCC TGACGAGCAT CACAAAAATC GACGCTCAAG TCAGAGGTGG    6120

CGAAACCCGA CAGGACTATA AAGATACCAG GCGTTTCCCC CTGGAAGCTC CCTCGTGCGC    6180

TCTCCTGTTC CGACCCTGCC GCTTACCGGA TACCTGTCCG CCTTTCTCCC TTCGGGAAGC    6240

GTGGCGCTTT CTCATAGCTC ACGCTGTAGG TATCTCAGTT CGGTGTAGGT CGTTCGCTCC    6300

AAGCTGGGCT GTGTGCACGA ACCCCCCGTT CAGCCCGACC GCTGCGCCTT ATCCGGTAAC    6360

TATCGTCTTG AGTCCAACCC GGTAAGACAC GACTTATCGC CACTGGCAGC AGCCACTGGT    6420

AACAGGATTA GCAGAGCGAG GTATGTAGGC GGTGCTACAG AGTTCTTGAA GTGGTGGCCT    6480

AACTACGGCT ACACTAGAAG GACAGTATTT GGTATCTGCG CTCTGCTGAA GCCAGTTACC    6540

TTCGGAAAAA GAGTTGGTAG CTCTTGATCC GGCAAACAAA CCACCGCTGG TAGCGGTGGT    6600

TTTTTTGTTT GCAAGCAGCA GATTACGCGC AGAAAAAAAG GATCTCAAGA AGATCCTTTG    6660

ATCTTTTCTA CGGGGTCTGA CGCTCAGTGG AACGAAAACT CACGTTAAGG GATTTTGGTC    6720

ATGAGATTAT CAAAAAGGAT CTTCACCTAG ATCCTTTTAA ATTAAAAATG AAGTTTTAAA    6780

TCAATCTAAA GTATATATGA GTAAACTTGG TCTGACAGTT ACCAATGCTT AATCAGTGAG    6840
```

```
GCACCTATCT CAGCGATCTG TCTATTTCGT TCATCCATAG TTGCCTGACT CCCCGTCGTG    6900

TAGATAACTA CGATACGGGA GGGCTTACCA TCTGGCCCCA GTGCTGCAAT GATACCGCGA    6960

GACCCACGCT CACCGGCTCC AGATTTATCA GCAATAAACC AGCCAGCCGG AAGGGCCGAG    7020

CGCAGAAGTG GTCCTGCAAC TTTATCCGCC TCCATCCAGT CTATTAATTG TTGCCGGGAA    7080

GCTAGAGTAA GTAGTTCGCC AGTTAATAGT TTGCGCAACG TTGTTGCCAT TGCTGCAGGC    7140

ATCGTGGTGT CACGCTCGTC GTTTGGTATG GCTTCATTCA GCTCCGGTTC CCAACGATCA    7200

AGGCGAGTTA CATGATCCCC CATGTTGTGC AAAAAAGCGG TTAGCTCCTT CGGTCCTCCG    7260

ATCGTTGTCA GAAGTAAGTT GGCCGCAGTG TTATCACTCA TGGTTATGGC AGCACTGCAT    7320

AATTCTCTTA CTGTCATGCC ATCCGTAAGA TGCTTTTCTG TGACTGGTGA GTACTCAACC    7380

AAGTCATTCT GAGAATAGTG TATGCGGCGA CCGAGTTGCT CTTGCCCGGC GTCAACACGG    7440

GATAATACCG CGCCACATAG CAGAACTTTA AAAGTGCTCA TCATTGGAAA ACGTTCTTCG    7500

GGGCGAAAAC TCTCAAGGAT CTTACCGCTG TTGAGATCCA GTTCGATGTA ACCCACTCGT    7560

GCACCCAACT GATCTTCAGC ATCTTTTACT TTCACCAGCG TTTCTGGGTG AGCAAAAACA    7620

GGAAGGCAAA ATGCCGCAAA AAAGGGAATA AGGGCGACAC GGAAATGTTG AATACTCATA    7680

CTCTTCCTTT TTCAATATTA TTGAAGCATT TATCAGGGTT ATTGTCTCAT GAGCGGATAC    7740

ATATTTGAAT GTATTTAGAA AAATAAACAA ATAGGGGTTC CGCGCACATT TCCCCGAAAA    7800

GTGCCACCTG ACGTCTAAGA AACCATTATT ATCATGACAT TAACCTATAA AAATAGGCGT    7860

ATCACGAGGC CCTTTCGTCT TCAAGAATTC CG                                 7892
```

( 2 ) INFORMATION FOR SEQ ID NO:41:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "370-38 PCR primer"

( x i ) SEQUENCE DESCRIPTION: SEQ ID NO:41:

```
TGAGCTTTCT GGGGCAGGCC AGGCCTGACC TTG                                  33
```

( 2 ) INFORMATION FOR SEQ ID NO:42:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "370-40 PCR primer"

( x i ) SEQUENCE DESCRIPTION: SEQ ID NO:42:

| | | | |
|---|---|---|---|
| AGTGTGGGGA CAGTGGGACC CGCTCTGCCT | | | 30 |

( 2 ) INFORMATION FOR SEQ ID NO:43:

( i ) SEQUENCE CHARACTERISTICS:
    ( A ) LENGTH: 2029 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "pBAG101 insert"

( x i ) SEQUENCE DESCRIPTION: SEQ ID NO:43:

| | | | | | | |
|---|---|---|---|---|---|---|
| TGAGCTTTCT | GGGGCAGGCC | AGGCCTGACC | TTGGCTGGGG | GCAGGGAGGG | GGCTAAGGTG | 60 |
| ACGCAGGTGG | CGCCAGCCAG | GTGCACACCC | AATGCCCATG | AGCCCAGACA | CTGGACCCTG | 120 |
| CATGGACCAT | CGCGGATAGA | CAAGAACCGA | GGGGCCTCTG | CGCCCTGGGC | CCAGCTCTGT | 180 |
| CCCACACCGC | GGTCACATGG | CACCACCTCT | CTTGCAGCTT | CCACCAAGGG | CCCATCCGTC | 240 |
| TTCCCCCTGG | CGCCCTGCTC | CAGGAGCACC | TCCGAGAGCA | CAGCCGCCCT | GGGCTGCCTG | 300 |
| GTCAAGGACT | ACTTCCCCGA | ACCGGTGACG | GTGTCGTGGA | ACTCAGGCGC | CCTGACCAGC | 360 |
| GGCGTGCACA | CCTTCCCGGC | TGTCCTACAG | TCCTCAGGAC | TCTACTCCCT | CAGCAGCGTG | 420 |
| GTGACCGTGC | CCTCCAGCAG | CTTGGGCACG | AAGACCTACA | CCTGCAACGT | AGATCACAAG | 480 |
| CCCAGCAACA | CCAAGGTGGA | CAAGAGAGTT | GGTGAGAGGC | CAGCACAGGG | AGGGAGGGTG | 540 |
| TCTGCTGGAA | GCCAGGCTCA | GCCCTCCTGC | CTGGACGCAC | CCCGGCTGTG | CAGCCCCAGC | 600 |
| CCAGGGCAGC | AAGGCATGCC | CCATCTGTCT | CCTCACCCGG | AGGCCTCTGA | CCACCCCACT | 660 |
| CATGCTCAGG | GAGAGGGTCT | TCTGGATTTT | TCCACCAGGC | TCCCGGCACC | ACAGGCTGGA | 720 |
| TGCCCCTACC | CCAGGCCCTG | CGCATACAGG | GCAGGTGCTG | CGCTCAGACC | TGCCAAGAGC | 780 |
| CATATCCGGG | AGGACCCTGC | CCCTGACCTA | AGCCCACCCC | AAAGGCCAAA | CTCTCCACTC | 840 |
| CCTCAGCTCA | GACACCTTCT | CTCCTCCCAG | ATCTGAGTAA | CTCCCAATCT | TCTCTCTGCA | 900 |
| GAGTCCAAAT | ATGGTCCCCC | ATGCCCATCA | TGCCCAGGTA | AGCCAACCCA | GGCCTCGCCC | 960 |
| TCCAGCTCAA | GGCGGGACAG | GTGCCCTAGA | GTAGCCTGCA | TCCAGGACA | GGCCCCAGCC | 1020 |
| GGGTGCTGAC | GCATCCACCT | CCATCTCTTC | CTCAGCACCT | GAGTTCCTGG | GGGGACCATC | 1080 |
| AGTCTTCCTG | TTCCCCCCAA | AACCCAAGGA | CACTCTCATG | ATCTCCCGGA | CCCCTGAGGT | 1140 |
| CACGTGCGTG | GTGGTGGACG | TGAGCCAGGA | AGACCCCGAG | GTCCAGTTCA | ACTGGTACGT | 1200 |
| GGATGGCGTG | GAGGTGCATA | ATGCCAAGAC | AAAGCCGCGG | GAGGAGCAGT | TCAACAGCAC | 1260 |
| GTACCGTGTG | GTCAGCGTCC | TCACCGTCCT | GCACCAGGAC | TGGCTGAACG | GCAAGGAGTA | 1320 |
| CAAGTGCAAG | GTCTCCAACA | AAGGCCTCCC | GTCCTCCATC | GAGAAAACCA | TCTCCAAAGC | 1380 |
| CAAAGGTGGG | ACCCACGGGG | TGCGAGGGCC | ACACGGACAG | AGGCCAGCTC | GGCCCACCCT | 1440 |
| CTGCCCTGGG | AGTGACCGCT | GTGCCAACCT | CTGTCCCTAC | AGGGCAGCCC | CGAGAGCCAC | 1500 |
| AGGTGTACAC | CCTGCCCCCA | TCCCAGGAGG | AGATGACCAA | GAACCAGGTC | AGCCTGACCT | 1560 |
| GCCTGGTCAA | AGGCTTCTAC | CCCAGCGACA | TCGCCGTGGA | GTGGGAGAGC | AATGGGCAGC | 1620 |

| | | | | | |
|---|---|---|---|---|---|
|CGGAGAACAA|CTACAAGACC|ACGCCTCCCG|TGCTGGACTC|CGACGGCTCC|TTCTTCCTCT 1680|
|ACAGCAGGCT|AACCGTGGAC|AAGAGCAGGT|GGCAGGAGGG|GAATGTCTTC|TCATGCTCCG 1740|
|TGATGCATGA|GGCTCTGCAC|AACCACTACA|CACAGAAGAG|CCTCTCCCTG|TCTCTGGGTA 1800|
|AATGAGTGCC|AGGGCCGGCA|AGCCCCCGCT|CCCCGGGCTC|TCGGGGTCGC|GCGAGGATGC 1860|
|TTGGCACGTA|CCCCGTCTAC|ATACTTCCCA|GGCACCCAGC|ATGGAAATAA|AGCACCCACC 1920|
|ACTGCCCTGG|GCCCCTGTGA|GACTGTGATG|GTTCTTTCCA|CGGGTCAGGC|CGAGTCTGAG 1980|
|GCCTGAGTGA|CATGAGGGAG|GCAGAGCGGG|TCCCACTGTC|CCCACACTA|2029|

( 2 ) INFORMATION FOR SEQ ID NO:44:

( i ) SEQUENCE CHARACTERISTICS:
        ( A ) LENGTH: 2560 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: sig_peptide
        ( B ) LOCATION: 12..68

( i x ) FEATURE:
        ( A ) NAME/KEY: mat_peptide
        ( B ) LOCATION: join(69..435, 712..1005, 1396..1431, 1550..1879,
                      1977..2296)

( i x ) FEATURE:
        ( A ) NAME/KEY: intron
        ( B ) LOCATION: 436..711

( i x ) FEATURE:
        ( A ) NAME/KEY: intron
        ( B ) LOCATION: 1006..1395

( i x ) FEATURE:
        ( A ) NAME/KEY: intron
        ( B ) LOCATION: 1432..1549

( i x ) FEATURE:
        ( A ) NAME/KEY: intron
        ( B ) LOCATION: 1880..1976

( i x ) FEATURE:
        ( A ) NAME/KEY: misc_feature
        ( B ) LOCATION: 1
        ( D ) OTHER INFORMATION: /note= "pMDR1002 insert: pre-5A8
                humanized heavy chain"

( i x ) FEATURE:
        ( A ) NAME/KEY: exon
        ( B ) LOCATION: 12..435

( i x ) FEATURE:
        ( A ) NAME/KEY: exon
        ( B ) LOCATION: 712..1005

( i x ) FEATURE:
        ( A ) NAME/KEY: exon
        ( B ) LOCATION: 1396..1431

( i x ) FEATURE:
        ( A ) NAME/KEY: exon
        ( B ) LOCATION: 1550..1879

( i x ) FEATURE:
        ( A ) NAME/KEY: exon
        ( B ) LOCATION: 1977..2296

( i x ) FEATURE:
  ( A ) NAME/KEY: CDS
  ( B ) LOCATION: join(12..435, 712..1005, 1396..1431, 1550..1879, 1977..2296)

( x i ) SEQUENCE DESCRIPTION: SEQ ID NO:44:

```
GCGGCCGCAC C ATG GAC TGG ACC TGG AGG GTC TTC TGC TTG CTG GCT GTA           50
             Met Asp Trp Thr Trp Arg Val Phe Cys Leu Leu Ala Val
             -19             -15                     -10

GCA CCA GGT GCC CAC TCC CAG GTC CAA CTG CAG GAG TCT GGA GCT GAA            98
Ala Pro Gly Ala His Ser Gln Val Gln Leu Gln Glu Ser Gly Ala Glu
    -5                   1                5                    10

GTG AAA AAG CCT GGG GCT TCA GTG AAG GTG TCC TGC AAG GCT TCT GGA            146
Val Lys Lys Pro Gly Ala Ser Val Lys Val Ser Cys Lys Ala Ser Gly
                15                   20                   25

TAC ACA TTC ACT AGC TAT GTT ATA CAC TGG GTG AGG CAG GCG CCT GGG            194
Tyr Thr Phe Thr Ser Tyr Val Ile His Trp Val Arg Gln Ala Pro Gly
            30                  35                      40

CAG GGC CTT GAG TGG ATT GGA TAT ATT AAT CCT TAC AAT GAT GGT ACT            242
Gln Gly Leu Glu Trp Ile Gly Tyr Ile Asn Pro Tyr Asn Asp Gly Thr
            45                  50                      55

GAC TAC GAT GAG AAG TTC AAA GGC AAG GCC ACA GTG ACT TTA GAC CCA            290
Asp Tyr Asp Glu Lys Phe Lys Gly Lys Ala Thr Val Thr Leu Asp Pro
    60                  65                  70

TCC ACC AAC ACA GCC TAC ATG GAG CTC AGC AGC CTG AGG TCT GAG GAC            338
Ser Thr Asn Thr Ala Tyr Met Glu Leu Ser Ser Leu Arg Ser Glu Asp
75                  80                  85                   90

ACT GCG GTC TAT TAC TGT GCA AGA GAG AAG GAT AAC TAC GCG ACG GGG            386
Thr Ala Val Tyr Tyr Cys Ala Arg Glu Lys Asp Asn Tyr Ala Thr Gly
                95                  100                  105

GCC TGG TTT GCT TAC TGG GGC CAA GGG ACC CTG GTC ACC GTC TCC TCA G          435
Ala Trp Phe Ala Tyr Trp Gly Gln Gly Thr Leu Val Thr Val Ser Ser
            110                 115                  120

GTGAGTCCTA AGCTTGGTAC CCGGGAATTC AGATCTGCAG CATGCTCGAG CTCTAGATAT          495

CAGCTTTCTG GGGCAGGCCG GGCCTGACTT TGGCTGGGGG CAGGGAGGGG GCTAAGGTGA          555

CGCAGGTGGC GCCAGCCAGG TGCACACCCA ATGCCCATGA GCCCAGACAC TGGACCCTGC          615

ATGGACCATC GCGGATAGAC AAGAACCGAG GGGCCTCTGC GCCCTGGGCC CAGCTCTGTC          675

CCACACCGCG GTCACATGGC ACCACCTCTC TTGCAG    CT TCC ACC AAG GGC CCA          728
                                            Ala Ser Thr Lys Gly Pro
                                                        125

TCC GTC TTC CCC CTG GCG CCC TGC TCC AGG AGC ACC TCC GAG AGC ACA            776
Ser Val Phe Pro Leu Ala Pro Cys Ser Arg Ser Thr Ser Glu Ser Thr
    130                 135                 140

GCC GCC CTG GGC TGC CTG GTC AAG GAC TAC TTC CCC GAA CCG GTG ACG            824
Ala Ala Leu Gly Cys Leu Val Lys Asp Tyr Phe Pro Glu Pro Val Thr
145                 150                 155                  160

GTG TCG TGG AAC TCA GGC GCC CTG ACC AGC GGC GTG CAC ACC TTC CCG            872
Val Ser Trp Asn Ser Gly Ala Leu Thr Ser Gly Val His Thr Phe Pro
                165                 170                  175

GCT GTC CTA CAG TCC TCA GGA CTC TAC TCC CTC AGC AGC GTG GTG ACC            920
Ala Val Leu Gln Ser Ser Gly Leu Tyr Ser Leu Ser Ser Val Val Thr
            180                 185                  190

GTG CCC TCC AGC AGC TTG GGC ACG AAG ACC TAC ACC TGC AAC GTA GAT            968
Val Pro Ser Ser Ser Leu Gly Thr Lys Thr Tyr Thr Cys Asn Val Asp
            195                 200                  205

CAC AAG CCC AGC AAC ACC AAG GTG GAC AAG AGA GTT    G GTGAGAGGCC           1015
His Lys Pro Ser Asn Thr Lys Val Asp Lys Arg Val
        210                 215                  220
```

| | |
|---|---:|
| AGCACAGGGA GGGAGGGTGT CTGCTGGAAG CCAGGCTCAG CCCTCCTGCC TGGACGCACC | 1075 |
| CCGGCTGTGC AGCCCCAGCC CAGGGCAGCA AGGCATGCCC CATCTGTCTC CTCACCCGGA | 1135 |
| GGCCTCTGAC CACCCCACTC ATGCTCAGGG AGAGGGTCTT CTGGATTTTT CCACCAGGCT | 1195 |
| CCCGGCACCA CAGGCTGGAT GCCCCTACCC CAGGCCCTGC GCATACAGGG CAGGTGCTGC | 1255 |
| GCTCAGACCT GCCAAGAGCC ATATCCGGGA GGACCCTGCC CCTGACCTAA GCCCACCCCA | 1315 |
| AAGGCCAAAC TCTCCACTCC CTCAGCTCAG ACACCTTCTC TCCTCCCAGA TCTGAGTAAC | 1375 |

```
TCCCAATCTT CTCTCTGCAG  AG TCC AAA TAT GGT CCC CCA TGC CCA TCA            1424
                         Glu Ser Lys Tyr Gly Pro Pro Cys Pro Ser
                                     225                 230

TGC CCA    G GTAAGCCAAC CCAGGCCTCG CCCTCCAGCT CAAGGCGGGA CAGGTGCCCT     1481
Cys Pro
```

| | |
|---|---:|
| AGAGTAGCCT GCATCCAGGG ACAGGCCCCA GCCGGGTGCT GACGCATCCA CCTCCATCTC | 1541 |

```
TTCCTCAG   CA CCT GAG TTC CTG GGG GGA CCA TCA GTC TTC CTG TTC CCC       1590
              Ala Pro Glu Phe Leu Gly Gly Pro Ser Val Phe Leu Phe Pro
                  235                 240                 245

CCA AAA CCC AAG GAC ACT CTC ATG ATC TCC CGG ACC CCT GAG GTC ACG        1638
Pro Lys Pro Lys Asp Thr Leu Met Ile Ser Arg Thr Pro Glu Val Thr
            250                 255                 260

TGC GTG GTG GTG GAC GTG AGC CAG GAA GAC CCC GAG GTC CAG TTC AAC        1686
Cys Val Val Val Asp Val Ser Gln Glu Asp Pro Glu Val Gln Phe Asn
        265                 270                 275

TGG TAC GTG GAT GGC GTG GAG GTG CAT AAT GCC AAG ACA AAG CCG CGG        1734
Trp Tyr Val Asp Gly Val Glu Val His Asn Ala Lys Thr Lys Pro Arg
    280                 285                 290

GAG GAG CAG TTC AAC AGC ACG TAC CGT GTG GTC AGC GTC CTC ACC GTC        1782
Glu Glu Gln Phe Asn Ser Thr Tyr Arg Val Val Ser Val Leu Thr Val
295                 300                 305                 310

CTG CAC CAG GAC TGG CTG AAC GGC AAG GAG TAC AAG TGC AAG GTC TCC        1830
Leu His Gln Asp Trp Leu Asn Gly Lys Glu Tyr Lys Cys Lys Val Ser
                315                 320                 325

AAC AAA GGC CTC CCG TCC TCC ATC GAG AAA ACC ATC TCC AAA GCC AAA  G     1879
Asn Lys Gly Leu Pro Ser Ser Ile Glu Lys Thr Ile Ser Lys Ala Lys
            330                 335                 340
```

| | |
|---|---:|
| GTGGGACCCA CGGGGTGCGA GGGCCACACG GACAGAGGCC AGCTCGGCCC ACCCTCTGCC | 1939 |
| CTGGGAGTGA CCGCTGTGCC AACCTCTGTC CCTACAG  GG CAG CCC CGA GAG CCA | 1993 |

```
                                           Gly Gln Pro Arg Glu Pro
                                                       345

CAG GTG TAC ACC CTG CCC CCA TCC CAG GAG GAG ATG ACC AAG AAC CAG        2041
Gln Val Tyr Thr Leu Pro Pro Ser Gln Glu Glu Met Thr Lys Asn Gln
    350                 355                 360

GTC AGC CTG ACC TGC CTG GTC AAA GGC TTC TAC CCC AGC GAC ATC GCC        2089
Val Ser Leu Thr Cys Leu Val Lys Gly Phe Tyr Pro Ser Asp Ile Ala
365                 370                 375                 380

GTG GAG TGG GAG AGC AAT GGG CAG CCG GAG AAC AAC TAC AAG ACC ACG        2137
Val Glu Trp Glu Ser Asn Gly Gln Pro Glu Asn Asn Tyr Lys Thr Thr
                385                 390                 395

CCT CCC GTG CTG GAC TCC GAC GGC TCC TTC TTC CTC TAC AGC AGG CTA        2185
Pro Pro Val Leu Asp Ser Asp Gly Ser Phe Phe Leu Tyr Ser Arg Leu
            400                 405                 410

ACC GTG GAC AAG AGC AGG TGG CAG GAG GGG AAT GTC TTC TCA TGC TCC        2233
Thr Val Asp Lys Ser Arg Trp Gln Glu Gly Asn Val Phe Ser Cys Ser
        415                 420                 425

GTG ATG CAT GAG GCT CTG CAC AAC CAC TAC ACA CAG AAG AGC CTC TCC        2281
Val Met His Glu Ala Leu His Asn His Tyr Thr Gln Lys Ser Leu Ser
    430                 435                 440

CTG TCT CTG GGT AAA TGAGTGCCAG GGCCGGCAAG CCCCCGCTCC CCGGGCTCTC        2336
Leu Ser Leu Gly Lys
```

```
Leu  Ser  Leu  Gly  Lys
445
```

```
GGGGTCGCGC  GAGGATGCTT  GGCACGTACC  CCGTCTACAT  ACTTCCCAGG  CACCCAGCAT    2396

GGAAATAAAG  CACCCACCAC  TGCCCTGGGC  CCCTGTGAGA  CTGTGATGGT  TCTTTCCACG    2456

GGTCAGGCCG  AGTCTGAGGC  CTGAGTGACA  TGAGGGAGGC  AGAGCGGGTC  CCACTGTCCC    2516

CACACTGGGA  TTCCATGGAT  CCTCACATCC  CAATCCGCGG  CCGC                      2560
```

( 2 ) INFORMATION FOR SEQ ID NO:45:

( i ) SEQUENCE CHARACTERISTICS:
        ( A ) LENGTH: 467 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

```
Met  Asp  Trp  Thr  Trp  Arg  Val  Phe  Cys  Leu  Leu  Ala  Val  Ala  Pro  Gly
-19            -15                 -10                           -5

Ala  His  Ser  Gln  Val  Gln  Leu  Gln  Glu  Ser  Gly  Ala  Glu  Val  Lys  Lys
               1                   5                           10

Pro  Gly  Ala  Ser  Val  Lys  Val  Ser  Cys  Lys  Ala  Ser  Gly  Tyr  Thr  Phe
          15                 20                      25

Thr  Ser  Tyr  Val  Ile  His  Trp  Val  Arg  Gln  Ala  Pro  Gly  Gln  Gly  Leu
30                      35                      40                           45

Glu  Trp  Ile  Gly  Tyr  Ile  Asn  Pro  Tyr  Asn  Asp  Gly  Thr  Asp  Tyr  Asp
               50                      55                           60

Glu  Lys  Phe  Lys  Gly  Lys  Ala  Thr  Val  Thr  Leu  Asp  Pro  Ser  Thr  Asn
               65                      70                           75

Thr  Ala  Tyr  Met  Glu  Leu  Ser  Ser  Leu  Arg  Ser  Glu  Asp  Thr  Ala  Val
               80                      85                      90

Tyr  Tyr  Cys  Ala  Arg  Glu  Lys  Asp  Asn  Tyr  Ala  Thr  Gly  Ala  Trp  Phe
     95                      100                     105

Ala  Tyr  Trp  Gly  Gln  Gly  Thr  Leu  Val  Thr  Val  Ser  Ser  Ala  Ser  Thr
110                     115                     120                          125

Lys  Gly  Pro  Ser  Val  Phe  Pro  Leu  Ala  Pro  Cys  Ser  Arg  Ser  Thr  Ser
               130                     135                     140

Glu  Ser  Thr  Ala  Ala  Leu  Gly  Cys  Leu  Val  Lys  Asp  Tyr  Phe  Pro  Glu
          145                     150                     155

Pro  Val  Thr  Val  Ser  Trp  Asn  Ser  Gly  Ala  Leu  Thr  Ser  Gly  Val  His
          160                     165                     170

Thr  Phe  Pro  Ala  Val  Leu  Gln  Ser  Ser  Gly  Leu  Tyr  Ser  Leu  Ser  Ser
     175                     180                     185

Val  Val  Thr  Val  Pro  Ser  Ser  Ser  Leu  Gly  Thr  Lys  Thr  Tyr  Thr  Cys
190                     195                     200                          205

Asn  Val  Asp  His  Lys  Pro  Ser  Asn  Thr  Lys  Val  Asp  Lys  Arg  Val  Glu
               210                     215                     220

Ser  Lys  Tyr  Gly  Pro  Pro  Cys  Pro  Ser  Cys  Pro  Ala  Pro  Glu  Phe  Leu
               225                     230                     235

Gly  Gly  Pro  Ser  Val  Phe  Leu  Phe  Pro  Pro  Lys  Pro  Lys  Asp  Thr  Leu
          240                     245                     250

Met  Ile  Ser  Arg  Thr  Pro  Glu  Val  Thr  Cys  Val  Val  Val  Asp  Val  Ser
     255                     260                     265

Gln  Glu  Asp  Pro  Glu  Val  Gln  Phe  Asn  Trp  Tyr  Val  Asp  Gly  Val  Glu
270                     275                     280                          285
```

| | | | | | | | | | | | | | | |
|---|---|---|---|---|---|---|---|---|---|---|---|---|---|---|
|Val|His|Asn|Ala|Lys 290|Thr|Lys|Pro|Arg|Glu 295|Glu|Phe|Asn|Ser|Thr 300|
|Tyr|Arg|Val|Val 305|Ser|Val|Leu|Thr|Val 310|Leu|His|Gln|Asp|Trp 315|Leu|Asn|
|Gly|Lys|Glu 320|Tyr|Lys|Cys|Lys|Val 325|Ser|Asn|Lys|Gly|Leu 330|Pro|Ser|Ser|
|Ile|Glu 335|Lys|Thr|Ile|Ser|Lys 340|Ala|Lys|Gln|Pro|Arg 345|Glu|Pro|Gln|Val|
|Tyr 350|Thr|Leu|Pro|Pro|Ser 355|Gln|Glu|Glu|Met|Thr 360|Lys|Asn|Gln|Val|Ser 365|
|Leu|Thr|Cys|Leu|Val 370|Lys|Gly|Phe|Tyr|Pro 375|Ser|Asp|Ile|Ala|Val 380|Glu|
|Trp|Glu|Ser|Asn 385|Gly|Gln|Pro|Glu|Asn 390|Asn|Tyr|Lys|Thr|Thr 395|Pro|Pro|
|Val|Leu|Asp 400|Ser|Asp|Gly|Ser|Phe 405|Phe|Leu|Tyr|Ser|Arg 410|Leu|Thr|Val|
|Asp|Lys 415|Ser|Arg|Trp|Gln|Glu 420|Gly|Asn|Val|Phe|Ser 425|Cys|Ser|Val|Met|
|His 430|Glu|Ala|Leu|His|Asn 435|His|Tyr|Thr|Gln|Lys 440|Ser|Leu|Ser|Leu|Ser 445|
|Leu|Gly|Lys| | | | | | | | | | | | | |

( 2 ) INFORMATION FOR SEQ ID NO:46:

( i ) SEQUENCE CHARACTERISTICS:
  ( A ) LENGTH: 77 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: misc_feature
  ( B ) LOCATION: 1
  ( D ) OTHER INFORMATION: /note= "360-81 oligonucleotide"

( x i ) SEQUENCE DESCRIPTION: SEQ ID NO:46:

AGCTTACCAT GGACATGAGG GTCCCCGCTC AGCTCCTGGG GCTCCTGCTG CTCTGGCTGC  60

CAGGTGCCAG AGGTGAT  77

( 2 ) INFORMATION FOR SEQ ID NO:47:

( i ) SEQUENCE CHARACTERISTICS:
  ( A ) LENGTH: 73 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: misc_feature
  ( B ) LOCATION: 1
  ( D ) OTHER INFORMATION: /note= "360-82 oligonucleotide"

( x i ) SEQUENCE DESCRIPTION: SEQ ID NO:47:

ATCACCTCTG GCACCTGGCA GCCAGAGCAG CAGGAGCCCC AGGAGCTGAG CGGGGACCCT 60

CATGTCCATG GTA 73

(2) INFORMATION FOR SEQ ID NO:48:

(i) SEQUENCE CHARACTERISTICS:
  (A) LENGTH: 77 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (ix) FEATURE:
  (A) NAME/KEY: misc_feature
  (B) LOCATION: 1
  (D) OTHER INFORMATION: /note= "pMDR985 insert"

(xi) SEQUENCE DESCRIPTION: SEQ ID NO:48:

AGCTTACCAT GGACATGAGG GTCCCCGCTC AGCTCCTGGG GCTCCTGCTG CTCTGGCTGC 60

CAGGTGCCAG AGGTGAT 77

(2) INFORMATION FOR SEQ ID NO:49:

(i) SEQUENCE CHARACTERISTICS:
  (A) LENGTH: 45 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (ix) FEATURE:
  (A) NAME/KEY: misc_feature
  (B) LOCATION: 1
  (D) OTHER INFORMATION: /note= "370-54 PCR primer"

(xi) SEQUENCE DESCRIPTION: SEQ ID NO:49:

TCCGTCGACA AACGTAAGTG CACTTTCTAA ACTCTGAGGG GGTCG 45

(2) INFORMATION FOR SEQ ID NO:50:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (ix) FEATURE:
  (A) NAME/KEY: misc_feature
  (B) LOCATION: 1
  (D) OTHER INFORMATION: /note= "370-55 PCR primer"

(xi) SEQUENCE DESCRIPTION: SEQ ID NO:50:

TTGGCGGCCG CAGGTTTCTT CTTTTGAAAA 30

(2) INFORMATION FOR SEQ ID NO:51:

( i ) SEQUENCE CHARACTERISTICS:
    ( A ) LENGTH: 1241 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: misc_feature
    ( B ) LOCATION: 1
    ( D ) OTHER INFORMATION: /note= "pSAB153 insert"

( x i ) SEQUENCE DESCRIPTION: SEQ ID NO:51:

```
TCGTCGACAA  ACGTAAGTGC  ACTTTCTAAA  CTCTGAGGGG  GTCGGATGAC  GTGGCCATTC    60
TTTGCCTAAA  GCATTGAGTT  TACTGCAAGG  TCAGAAAAGC  ATGCAAAGCC  CTCAGAATGG   120
CTGCAAAGAG  CTCCAACAAA  ACAATTTAGA  ACTTTATTAA  GGATAGGGG   GAAGCTAGGA   180
AGAAACTCAA  AACATCAAGA  TTTTAAATAC  GCTTCTTGGT  CTCCTTGCTA  TAATTATCTG   240
GGATAAGCAT  GCTGTTTTCT  GTCTGTCCCT  AACATGCCCT  GTGATTATCC  GCAAACAACA   300
CACCCAAGGG  CAGAACTTTG  TTACTAAAC   ACCATCCTGT  TTGCTTCTTT  CCTCAGGAAC   360
TGTGGCTGCA  CCATCTGTCT  TCATCTTCCC  GCCATCTGAT  GAGCAGTTGA  AATCTGGAAC   420
TGCCTCTGTT  GTGTGCCTGC  TGAATAACTT  CTATCCAGA   GAGGCCAAAG  TACAGTGGAA   480
GGTGGATAAC  GCCCTCCAAT  CGGGTAACTC  CCAGGAGAGT  GTCACAGAGC  AGGACAGCAA   540
GGACAGCACC  TACAGCCTCA  GCAGCACCCT  GACGCTGAGC  AAAGCAGACT  ACGAGAAACA   600
CAAAGTCTAC  GCCTGCGAAG  TCACCCATCA  GGGCCTGAGC  TCGCCCGTCA  CAAAGAGCTT   660
CAACAGGGGA  GAGTGTTAGA  GGGAGAAGTG  CCCCCACCTG  CTCCTCAGTT  CCAGCCTGAC   720
CCCCTCCCAT  CCTTTGGCCT  CTGACCCTTT  TTCCACAGGG  GACCTACCCC  TATTGCGGTC   780
CTCCAGCTCA  TCTTTCACCT  CACCCCCCTC  CTCCTCCTTG  GCTTAATTA   TGCTAATGTT   840
GGAGGAGAAT  GAATAAATAA  AGTGAATCTT  TGCACCTGTG  GTTTCTCTCT  TTCCTCAATT   900
TAATAATTAT  TATCTGTTGT  TTACCAACTA  CTCAATTTCT  CTTATAAGGG  ACTAAATATG   960
TAGTCATCCT  AAGGCGCATA  ACCATTTATA  AAAATCATCC  TTCATTCTAT  TTTACCCTAT  1020
CATCCTCTGC  AAGACAGTCC  TCCCTCAAAC  CCACAAGCCT  TCTGTCCTCA  CAGTCCCCTG  1080
GGCCGTGGTA  GGAGAGACTT  GCTTCCTTGT  TTTCCCCTCC  TCAGCAAGCC  CTCATAGTCC  1140
TTTTTAAGGG  TGACAGGTCT  TACGGTCATA  TATCCTTTGA  TTCAATTCCC  TGGGAATCAA  1200
CCAAGGCAAA  TTTTTCAAAA  GAAGAAACCT  GCGGCCGCCA  A                       1241
```

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1

(D) OTHER INFORMATION: /note= "360-83 PCR primer"

(x i) SEQUENCE DESCRIPTION: SEQ ID NO:52:

TCATGATCAA ACGTAAGTGC                                                            20

(2) INFORMATION FOR SEQ ID NO:53:

(i) SEQUENCE CHARACTERISTICS:
        (A) LENGTH: 1276 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: misc_feature
        (B) LOCATION: 1
        (D) OTHER INFORMATION: /note= "pMDR986 insert"

(x i) SEQUENCE DESCRIPTION: SEQ ID NO:53:

TCATGATCAA ACGTAAGTGC ACTTTCTAAA CTCTGAGGGG GTCGGATGAC GTGGCCATTC        60

TTTGCCTAAA GCATTGAGTT TACTGCAAGG TCAGAAAAGC ATGCAAAGCC CTCAGAATGG       120

CTGCAAAGAG CTCCAACAAA ACAATTTAGA ACTTTATTAA GGAATAGGGG GAAGCTAGGA       180

AGAAACTCAA AACATCAAGA TTTTAAATAC GCTTCTTGGT CTCCTTGCTA TAATTATCTG       240

GGATAAGCAT GCTGTTTTCT GTCTGTCCCT AACATGCCCT GTGATTATCC GCAAACAACA       300

CACCCAAGGG CAGAACTTTG TTACTAAAC ACCATCCTGT TTGCTTCTTT CCTCAGGAAC        360

TGTGGCTGCA CCATCTGTCT TCATCTTCCC GCCATCTGAT GAGCAGTTGA AATCTGGAAC       420

TGCCTCTGTT GTGTGCCTGC TGAATAACTT CTATCCAGA GAGGCCAAAG TACAGTGGAA        480

GGTGGATAAC GCCCTCCAAT CGGGTAACTC CAGGAGAGT GTCACAGAGC AGGACAGCAA        540

GGACAGCACC TACAGCCTCA GCAGCACCCT GACGCTGAGC AAAGCAGACT ACGAGAAACA      600

CAAAGTCTAC GCCTGCGAAG TCACCCATCA GGGCCTGAGC TCGCCCGTCA CAAAGAGCTT       660

CAACAGGGGA GAGTGTTAGA GGGAGAAGTG CCCCCACCTG CTCCTCAGTT CCAGCCTGAC      720

CCCCTCCCAT CCTTTGGCCT CTGACCCTTT TTCCACAGGG GACCTACCCC TATTGCGGTC       780

CTCCAGCTCA TCTTTCACCT CACCCCCCTC CTCCTCCTTG GCTTAATTA TGCTAATGTT        840

GGAGGAGAAT GAATAAATAA AGTGAATCTT TGCACCTGTG GTTTCTCTCT TTCCTCAATT       900

TAATAATTAT TATCTGTTGT TTACCAACT ACTCAATTTC TCTTATAAGG GACTAAATAT        960

GTAGTACTCC TAAGGCGATA ACCATTTATA AAAATCATCC TTCATTCTAT TTACCCTAT      1020

CATCCTCTGC AAGACAGTCC TCCCTCAAAC CCACAAGCCT TCTGTCCTCA CAGTCCCCTG     1080

GGCCATGGTA GGAGAGACTT GCTTCCTTGT TTTCCCCTCC TCAGCAAGCC CTCATAGTCC    1140

TTTTTAAGGG TGACAGGTCT TACAGTCATA TATCCTTTGA TTCAATTCCC TGAGAATCAA    1200

CCAAAGCAAA TTTTTCAAAA GAAGAAACCT GCGGCCGATC GATTCCATGG ATCCTCACAT    1260

CCCAATCCGC GGCCGC                                                         1276

(2) INFORMATION FOR SEQ ID NO:54:

(i) SEQUENCE CHARACTERISTICS:
        (A) LENGTH: 1701 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
    (A) NAME/KEY: misc_feature
    (B) LOCATION: 1
    (D) OTHER INFORMATION: /note= "pMDR1006 insert"

(x i) SEQUENCE DESCRIPTION: SEQ ID NO:54:

| | | | | | |
|---|---|---|---|---|---|
| GCGGCCGCGG | TCCAACCACC | AATCTCAGCT | TACCATGGAC | ATGAGGGTCC | CCGCTCAGCT | 60 |
| CCTGGGGCTC | CTGCTGCTCT | GGCTGCCAGG | TGCCAGAGGT | GATATCGTAA | TGACCCAGTC | 120 |
| TCCAGACTCC | CTAGCTGTGT | CACTTGGAGA | GAGGGCTACT | ATAAACTGCA | AGTCCAGTGG | 180 |
| GAGCCTTTTA | TATAGTACCA | ATCAAAAGAA | CTACTTGGCC | TGGTACCAGC | AGAAACCAGG | 240 |
| GCAGCCTCCT | AAACTGCTGA | TTTACTGGGC | ATCCACTAGG | GAATCTGGGG | TCCCTGATCG | 300 |
| CTTCTCAGGC | AGTGGATCTG | GGACAGATTT | CACTCTCACC | ATCAGCAGTT | TGCAGGCTGA | 360 |
| AGACGTGGCA | GTTTATTACT | GTCAGCAATA | TTATAGCTAT | CGGACGTTCG | GTCGAGGGAC | 420 |
| CAAGCTGGAG | ATCAAACGTA | AGTGCACTTT | CTAAACTCTG | AGGGGGTCGG | ATGACGTGGC | 480 |
| CATTCTTTGC | CTAAAGCATT | GAGTTACTG | CAAGGTCAGA | AAAGCATGCA | AAGCCCTCAG | 540 |
| AATGGCTGCA | AAGAGCTCCA | ACAAAACAAT | TTAGAACTTT | ATTAAGGAAT | AGGGGAAGC | 600 |
| TAGGAAGAAA | CTCAAAACAT | CAAGATTTTA | AATACGCTTC | TTGGTCTCCT | TGCTATAATT | 660 |
| ATCTGGGATA | AGCATGCTGT | TTTCTGTCTG | TCCCTAACAT | GCCCTGTGAT | TATCCGCAAA | 720 |
| CAACACACCC | AAGGGCAGAA | CTTTGTTACT | TAAACACCAT | CCTGTTTGCT | TCTTTCCTCA | 780 |
| GGAACTGTGG | CTGCACCATC | TGTCTTCATC | TTCCCGCCAT | CTGATGAGCA | GTTGAAATCT | 840 |
| GGAACTGCCT | CTGTTGTGTG | CCTGCTGAAT | AACTTCTATC | CCAGAGAGGC | CAAAGTACAG | 900 |
| TGGAAGGTGG | ATAACGCCCT | CCAATCGGGT | AACTCCCAGG | AGAGTGTCAC | AGAGCAGGAC | 960 |
| AGCAAGGACA | GCACCTACAG | CCTCAGCAGC | ACCCTGACGC | TGAGCAAAGC | AGACTACGAG | 1020 |
| AAACACAAAG | TCTACGCCTG | CGAAGTCACC | CATCAGGGCC | TGAGCTCGCC | CGTCACAAAG | 1080 |
| AGCTTCAACA | GGGGAGAGTG | TTAGAGGGAG | AAGTGCCCCC | ACCTGCTCCT | CAGTTCCAGC | 1140 |
| CTGACCCCCT | CCCATCCTTT | GGCCTCTGAC | CCTTTTCCA | CAGGGGACCT | ACCCCTATTG | 1200 |
| CGGTCCTCCA | GCTCATCTTT | CACCTCACCC | CCCTCCTCCT | CCTTGGCTTT | AATTATGCTA | 1260 |
| ATGTTGGAGG | AGAATGAATA | AATAAAGTGA | ATCTTTGCAC | CTGTGGTTTC | TCTCTTTCCT | 1320 |
| CAATTTAATA | ATTATTATCT | GTTGTTTACC | AACTACTCAA | TTTCTCTTAT | AAGGGACTAA | 1380 |
| ATATGTAGTC | ATCCTAAGGC | GCATAACCAT | TTATAAAAAT | CATCCTTCAT | TCTATTTTAC | 1440 |
| CCTATCATCC | TCTGCAAGAC | AGTCCTCCCT | CAAACCCACA | AGCCTTCTGT | CCTCACAGTC | 1500 |
| CCCTGGGCCG | TGGTAGGAGA | GACTTGCTTC | CTTGTTTTCC | CCTCCTCAGC | AAGCCCTCAT | 1560 |
| AGTCCTTTTT | AAGGGTGACA | GGTCTTACGG | TCATATATCC | TTTGATTCAA | TTCCCTGGGA | 1620 |
| ATCAACCAAG | GCAAATTTTT | CAAAAGAAGA | AACCTGCGGC | CGATCGATTC | CATGGATCCT | 1680 |
| CACATCCCAA | TCCGCGGCCG | C | | | | 1701 |

(2) INFORMATION FOR SEQ ID NO:55:

(i) SEQUENCE CHARACTERISTICS:
        (A) LENGTH: 1701 base pairs
        (B) TYPE: nucleic acid
        (C) STRANDEDNESS: single
        (D) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: sig_peptide
    ( B ) LOCATION: 35..100

( i x ) FEATURE:
    ( A ) NAME/KEY: mat_peptide
    ( B ) LOCATION: join(101..437, 782..1101)

( i x ) FEATURE:
    ( A ) NAME/KEY: intron
    ( B ) LOCATION: 438..781

( i x ) FEATURE:
    ( A ) NAME/KEY: misc_feature
    ( B ) LOCATION: 1
    ( D ) OTHER INFORMATION: /note= "pMDR1007 insert: pre-5A8 humanized light chain"

( i x ) FEATURE:
    ( A ) NAME/KEY: exon
    ( B ) LOCATION: 35..436

( i x ) FEATURE:
    ( A ) NAME/KEY: exon
    ( B ) LOCATION: 782..1101

( i x ) FEATURE:
    ( A ) NAME/KEY: CDS
    ( B ) LOCATION: join(35..437, 782..1101)

( x i ) SEQUENCE DESCRIPTION: SEQ ID NO:55:

```
GCGGCCGCGG  TCCAACCACC  AATCTCAGCT  TACC ATG GAC ATG AGG GTC CCC           52
                                         Met Asp Met Arg Val Pro
                                         -22         -20

GCT CAG CTC CTG GGG CTC CTG CTG CTC TGG CTG CCA GGT GCC AGA GGT           100
Ala Gln Leu Leu Gly Leu Leu Leu Leu Trp Leu Pro Gly Ala Arg Gly
    -15             -10                  -5

GAT ATC GTA ATG ACC CAG TCT CCA GAC TCC CTA GCT GTG TCA CTT GGA           148
Asp Ile Val Met Thr Gln Ser Pro Asp Ser Leu Ala Val Ser Leu Gly
 1           5                  10                  15

GAG AGG GCT ACT ATA AAC TGC AAG TCC AGT GGG AGC CTT TTA TAT AGT           196
Glu Arg Ala Thr Ile Asn Cys Lys Ser Ser Gly Ser Leu Leu Tyr Ser
             20                  25                  30

ACC AAT CAA AAG AAC TAC TTG GCC TGG TAC CAG CAG AAA CCA GGG CAG           244
Thr Asn Gln Lys Asn Tyr Leu Ala Trp Tyr Gln Gln Lys Pro Gly Gln
             35                  40                  45

CCT CCT AAA CTG CTG ATT TAC TGG GCA TCC ACT AGG GAA TCT GGG GTC           292
Pro Pro Lys Leu Leu Ile Tyr Trp Ala Ser Thr Arg Glu Ser Gly Val
     50                  55                  60

CCT GAT CGC TTC TCA GGC AGT GGA TCT GGG ACA GAT TTC ACT CTC ACC           340
Pro Asp Arg Phe Ser Gly Ser Gly Ser Gly Thr Asp Phe Thr Leu Thr
 65              70                  75                  80

ATC AGC AGT TTG CAG GCT GAA GAC GTG GCA GTT TAT TAC TGT CAG CAA           388
Ile Ser Ser Leu Gln Ala Glu Asp Val Ala Val Tyr Tyr Cys Gln Gln
                 85                  90                  95

TAT TAT AGC TAT CGG ACG TTC GGT CGA GGG ACC AAG CTG GAG ATC AAA   C       437
Tyr Tyr Ser Tyr Arg Thr Phe Gly Arg Gly Thr Lys Leu Glu Ile Lys
                 100                 105                 110

GTAAGTGCAC  TTTCTAAACT  CTGAGGGGGT  CGGATGACGT  GGCCATTCTT  TGCCTAAAGC    497

ATTGAGTTTA  CTGCAAGGTC  AGAAAAGCAT  GCAAAGCCCT  CAGAATGGCT  GCAAAGAGCT    557

CCAACAAAAC  AATTTAGAAC  TTTATTAAGG  AATAGGGGGA  AGCTAGGAAG  AAACTCAAAA    617
```

```
CATCAAGATT TTAAATACGC TTCTTGGTCT CCTTGCTATA ATTATCTGGG ATAAGCATGC      677

TGTTTTCTGT CTGTCCCTAA CATGCCCTGT GATTATCCGC AAACAACACA CCCAAGGGCA      737

GAACTTTGTT ACTTAAACAC CATCCTGTTT GCTTCTTTCC TCAG GA ACT GTG GCT       792
                                                  Arg Thr Val Ala
                                                          115

GCA CCA TCT GTC TTC ATC TTC CCG CCA TCT GAT GAG CAG TTG AAA TCT       840
Ala Pro Ser Val Phe Ile Phe Pro Pro Ser Asp Glu Gln Leu Lys Ser
        120                 125                 130

GGA ACT GCC TCT GTT GTG TGC CTG CTG AAT AAC TTC TAT CCC AGA GAG       888
Gly Thr Ala Ser Val Val Cys Leu Leu Asn Asn Phe Tyr Pro Arg Glu
        135                 140                 145

GCC AAA GTA CAG TGG AAG GTG GAT AAC GCC CTC CAA TCG GGT AAC TCC       936
Ala Lys Val Gln Trp Lys Val Asp Asn Ala Leu Gln Ser Gly Asn Ser
        150                 155                 160

CAG GAG AGT GTC ACA GAG CAG GAC AGC AAG GAC AGC ACC TAC AGC CTC       984
Gln Glu Ser Val Thr Glu Gln Asp Ser Lys Asp Ser Thr Tyr Ser Leu
165                 170                 175                 180

AGC AGC ACC CTG ACG CTG AGC AAA GCA GAC TAC GAG AAA CAC AAA GTC      1032
Ser Ser Thr Leu Thr Leu Ser Lys Ala Asp Tyr Glu Lys His Lys Val
                185                 190                 195

TAC GCC TGC GAA GTC ACC CAT CAG GGC CTG AGC TCG CCC GTC ACA AAG      1080
Tyr Ala Cys Glu Val Thr His Gln Gly Leu Ser Ser Pro Val Thr Lys
            200                 205                 210

AGC TTC AAC AGG GGA GAG TGT TAGAGGGAGA AGTGCCCCCA CCTGCTCCTC          1131
Ser Phe Asn Arg Gly Glu Cys
                215

AGTTCCAGCC TGACCCCCTC CCATCCTTTG GCCTCTGACC CTTTTTCCAC AGGGGACCTA    1191

CCCCTATTGC GGTCCTCCAG CTCATCTTTC ACCTCACCCC CCTCCTCCTC CTTGGCTTTA    1251

ATTATGCTAA TGTTGGAGGA GAATGAATAA ATAAAGTGAA TCTTTGCACC TGTGGTTTCT    1311

CTCTTTCCTC AATTTAATAA TTATTATCTG TTGTTACCA ACTACTCAAT TTCTCTTATA     1371

AGGGACTAAA TATGTAGTCA TCCTAAGGCG CATAACCATT TATAAAAATC ATCCTTCATT    1431

CTATTTTACC CTATCATCCT CTGCAAGACA GTCCTCCCTC AAACCCACAA GCCTTCTGTC    1491

CTCACAGTCC CCTGGGCCGT GGTAGGAGAG ACTTGCTTCC TTGTTTTCCC CTCCTCAGCA    1551

AGCCCTCATA GTCCTTTTTA AGGGTGACAG GTCTTACGGT CATATATCCT TGATTCAAT    1611

TCCCTGGGAA TCAACCAAGG CAAATTTTTC AAAAGAAGAA ACCTGCGGCC GATCGATTCC    1671

ATGGATCCTC ACATCCCAAT CCGCGGCCGC                                     1701
```

( 2 ) INFORMATION FOR SEQ ID NO:56:

( i ) SEQUENCE CHARACTERISTICS:
        ( A ) LENGTH: 241 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

```
Met Asp Met Arg Val Pro Ala Gln Leu Leu Gly Leu Leu Leu Leu Trp
-22         -20                 -15                 -10

Leu Pro Gly Ala Arg Gly Asp Ile Val Met Thr Gln Ser Pro Asp Ser
        -5                   1                   5                10

Leu Ala Val Ser Leu Gly Glu Arg Ala Thr Ile Asn Cys Lys Ser Ser
                    15                  20                  25

Gly Ser Leu Leu Tyr Ser Thr Asn Gln Lys Asn Tyr Leu Ala Trp Tyr
            30                  35                  40
```

```
Gln  Gln  Lys  Pro  Gly  Gln  Pro  Pro  Lys  Leu  Leu  Ile  Tyr  Trp  Ala  Ser
          45                       50                      55

Thr  Arg  Glu  Ser  Gly  Val  Pro  Asp  Arg  Phe  Ser  Gly  Ser  Gly  Ser  Gly
     60                       65                      70

Thr  Asp  Phe  Thr  Leu  Thr  Ile  Ser  Ser  Leu  Gln  Ala  Glu  Asp  Val  Ala
75                       80                      85                           90

Val  Tyr  Tyr  Cys  Gln  Gln  Tyr  Tyr  Ser  Tyr  Arg  Thr  Phe  Gly  Arg  Gly
                    95                      100                     105

Thr  Lys  Leu  Glu  Ile  Lys  Arg  Thr  Val  Ala  Ala  Pro  Ser  Val  Phe  Ile
               110                      115                     120

Phe  Pro  Pro  Ser  Asp  Glu  Gln  Leu  Lys  Ser  Gly  Thr  Ala  Ser  Val  Val
          125                      130                     135

Cys  Leu  Leu  Asn  Asn  Phe  Tyr  Pro  Arg  Glu  Ala  Lys  Val  Gln  Trp  Lys
     140                      145                     150

Val  Asp  Asn  Ala  Leu  Gln  Ser  Gly  Asn  Ser  Gln  Glu  Ser  Val  Thr  Glu
155                      160                     165                          170

Gln  Asp  Ser  Lys  Asp  Ser  Thr  Tyr  Ser  Leu  Ser  Ser  Thr  Leu  Thr  Leu
               175                      180                     185

Ser  Lys  Ala  Asp  Tyr  Glu  Lys  His  Lys  Val  Tyr  Ala  Cys  Glu  Val  Thr
               190                      195                     200

His  Gln  Gly  Leu  Ser  Ser  Pro  Val  Thr  Lys  Ser  Phe  Asn  Arg  Gly  Glu
          205                      210                     215

Cys
```

( 2 ) INFORMATION FOR SEQ ID NO:57:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "pNN03 synthetic polylinker"

( x i ) SEQUENCE DESCRIPTION: SEQ ID NO:57:

```
GCGGCCGCGG  TCCAACCACC  AATCTCAAAG  CTTGGTACCC  GGGAATTCAG  ATCTGCAGCA      60
TGCTCGAGCT  CTAGATATCG  ATTCCATGGA  TCCTCACATC  CCAATCCGCG  GCCGC          115
```

( 2 ) INFORMATION FOR SEQ ID NO:58:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1

( D ) OTHER INFORMATION: /note= "312-46 oligonucleotide"

( x i ) SEQUENCE DESCRIPTION: SEQ ID NO:58:

TGTAGCACCA GGTGCCCACT CCCAGGTCCA ACTGCAGTCT AGAG 44

( 2 ) INFORMATION FOR SEQ ID NO:59:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "312-47 oligonucleotide"

( x i ) SEQUENCE DESCRIPTION: SEQ ID NO:59:

TCGACCTCGA GGGTCACCGT CTCCTCAGGT GAGTCCTAAG CTTG 44

( 2 ) INFORMATION FOR SEQ ID NO:60:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "312-48 oligonucleotide"

( x i ) SEQUENCE DESCRIPTION: SEQ ID NO:60:

GCAAGCAGAA GACCCTCCAG GTCCAGTCCA TGGTGCGGCC GCGGTA 46

( 2 ) INFORMATION FOR SEQ ID NO:61:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note= "312-49 oligonucleotide"

( x i ) SEQUENCE DESCRIPTION: SEQ ID NO:61:

TCGACTCTAG ACTGCAGTTG GACCTGGGAG TGGGCACCTG GTGCTACAGC CA 52